(12) United States Patent
Zhu et al.

(10) Patent No.: US 12,324,927 B2
(45) Date of Patent: Jun. 10, 2025

(54) METHODS AND SYSTEMS FOR PHOTODYNAMIC THERAPY CALCULATIONS

(71) Applicant: THE TRUSTEES OF THE UNIVERSITY OF PENNSYLVANIA, Philadelphia, PA (US)

(72) Inventors: Timothy C. Zhu, Glen Mills, PA (US); Arjun G. Yodh, Merion, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 971 days.

(21) Appl. No.: 17/291,703

(22) PCT Filed: Nov. 6, 2019

(86) PCT No.: PCT/US2019/060043
§ 371 (c)(1),
(2) Date: May 6, 2021

(87) PCT Pub. No.: WO2020/097186
PCT Pub. Date: May 14, 2020

(65) Prior Publication Data
US 2022/0001193 A1    Jan. 6, 2022

Related U.S. Application Data

(60) Provisional application No. 62/756,380, filed on Nov. 6, 2018.

(51) Int. Cl.
*A61B 5/026* (2006.01)
*A61B 5/00* (2006.01)
(Continued)

(52) U.S. Cl.
CPC ............ *A61N 5/062* (2013.01); *A61B 5/0261* (2013.01); *A61B 5/1459* (2013.01);
(Continued)

(58) Field of Classification Search
CPC .................. A61N 5/062; A61N 5/0603; A61N 2005/0628; A61N 2005/063;
(Continued)

(56) References Cited

U.S. PATENT DOCUMENTS 4,576,173 A    3/1986  Parker et al.
6,146,410 A *  11/2000 Nagypal .............. A61N 5/0601
                                                      606/12

(Continued)

OTHER PUBLICATIONS

Penjweini, R., Loew, H-G., Breit, P., Kratky, K. W., "Optimizing the anti tumor selectivity of PVP-Hypericin re A549 cancer cells and HLF normal cells through pulsed blue light," Photodiagnosis and photodynamic therapy 10(4), 591-599 (2013).
(Continued)

*Primary Examiner* — Ankit D Tejani
*Assistant Examiner* — Joshua Brendon Solomon
(74) *Attorney, Agent, or Firm* — BakerHostetler

(57) ABSTRACT

Methods and systems are described for implementing a photodynamic therapy. An example method may comprise determining, during photodynamic therapy and using a plurality of optical probes spatially distributed within a patient, data indicative of one or more of a photodynamic therapy dosage, a fluence rate of a photodynamic therapy treatment light, or a reactive oxygen species concentration associated with corresponding locations of the plurality of optical probes. The example method may comprise changing, based on the data, one or more treatment parameters associated with providing a photodynamic therapy.

25 Claims, 31 Drawing Sheets

(51) Int. Cl.
*A61B 5/1459* (2006.01)
*A61N 5/06* (2006.01)

(52) U.S. Cl.
CPC .......... *A61B 5/4836* (2013.01); *A61B 5/6852* (2013.01); *A61N 5/0603* (2013.01); *A61B 2562/0233* (2013.01); *A61B 2562/228* (2013.01); *A61N 2005/0628* (2013.01); *A61N 2005/063* (2013.01)

(58) Field of Classification Search
CPC .......... A61N 2005/0626; A61B 5/0261; A61B 5/1459; A61B 5/4836; A61B 5/6852; A61B 5/0075; A61B 5/14552; A61B 5/0059; A61B 5/0071; A61B 2562/0233; A61B 2562/228; G01N 21/64; G01N 21/76

See application file for complete search history.

(56) References Cited

U.S. PATENT DOCUMENTS

| | | | | |
|---|---|---|---|---|
| 6,166,806 | A * | 12/2000 | Tjin | G01S 7/4818 356/336 |
| 6,416,531 | B2 | 7/2002 | Chen | |
| 2007/0135874 | A1 * | 6/2007 | Bala | A61N 5/0603 607/94 |
| 2010/0069824 | A1 * | 3/2010 | Okamoto | A61N 5/062 604/21 |
| 2010/0329524 | A1 | 12/2010 | Swartling | |
| 2012/0209125 | A1 | 8/2012 | Davis et al. | |
| 2018/0070831 | A1 * | 3/2018 | Sutin | A61B 5/369 |
| 2018/0207442 | A1 * | 7/2018 | Shafirstein | A61N 5/062 |

OTHER PUBLICATIONS

Prahl S A, Keijzer M, Jacques S L and Welch A J A Monte Carlo model of light propagation in tissue Proc. SPIE IS5 102-11.1989.
Qiu, H., Kim, M. M., Penjweini, R., Zhu, T. C., "Macroscopic singlet oxygen modeling for dosimetry of Photofrinmediated photodynamic therapy: an in-vivo study," Journal of biomedical optics 21(8), 88002 (2016).
Qui, H., et al., "Dosimetry study of Photofrin-mediated photodynamic therapy in a mouse tumor model," Proc. SPIE 9694, Optical Methods for Tumor Treatment and Detection: Mechanisms and Techniques in Photodynamic Therapy XXV, 96940T (Mar. 1, 2016).
R. C. Mesquita et al., "Tumor blood flow differs between mouse strains: consequences for vasoresponse to photodynamic therapy," PLoS One 7(5), e37322 (2012).
Rozhin Penjweini, Michele M. Kim, Yi Hong Ong, Timothy C. Zhu Singlet oxygen explicit dosimetry to predict long-term local tumor control for Photofrin-mediated photodynamic therapy. Proc SPIE 10047: 1004711.2017.
Sandell J L and Zhu T C A review of in vivo optical properties of human tissues and its impact on PDT J. Biophoton. 4 773-87.2011.
Sharikova A V, Finlay J C, Liang X and Zhu T C PDT dose dosimetry for pleural photodynamic therapy Proc. SPIE 8568 856817. 2013.
Sheng, T., et al., "Reactive oxygen species explicit dosimetry to predict local tumor control for Photofrin-mediated photodynamic therapy," Biomedical Optics Express, vol. 11, Issue 8, Jul. 2020, pp. 4586-4601.
Simone C B and Cengel K A Photodynamic therapy for lung cancer and malignant pleural mesothelioma Semin. Oncol. 41 820-30. 2014.
Solonenko M, Cheung R, Busch T M, Kachur A, Griffin G M, Vulcan T, Zhu T C, Wang H W, Hahn S M and Yodh A G In vivo reflectance measurement of optical properties, blood oxygenation and motexafin lutetium uptake in canine large bowels, kidneys and prostates Phys. Med. Biol. 47 857-73.2002.

T. C. Zhu et al., "Comparison of singlet oxygen threshold dose for PDT," Proc. SPIE 8931, 89310! (2014).
T. M. Busch et al., "Fluence rate-dependent intratumor heterogeneity in physiologic and cytotoxic responses to photofrin photodynamic therapy," Photochem. Photobiol. Sci. 8(12), 1683-1693 (2009).
Triesscheijn M, Baas P, Schellens J H M and Stewart F A Photodynamic therapy in oncology Oncologist 11 1034-44.2006.
Wang H W et al Broadband reflectance measurements of light penetration, blood oxygenation, hemoglobin concentration, and drug concentration in human intraperitoneal tissues before and after photodynamic therapy J. Biomed. Opt. 10 14004.2005.
Weersink R A, Bogaards A, Gertner M, Davidson S R, Zhang K, Netchev G, Trachtenberg J and Wilson B C Techniques for delivery and monitoring of TOOKAD (WST09)-mediated photodynamic therapy of the prostate: clinical experience and practicalities J. Photochem. Photobiol. B 79 211-22 Phys. Med. Biol. 63 (2018) 015031 (14pp) 14.2005.
Wei, Y., "In vivo monitoring of singlet oxygen using delayed chemiluminescence during photodynamic therapy," Journal of Biomedical Optics, vol. 12, No. 1, Jan. 2007, pp. 014002-1-014002-7.
Whiteley, J.P., et al., "Mathematical modelling of oxygen transport to tissue," Journal of Mathematical Biology, vol. 44, No. 6, Jul. 2002, pp. 503-522.
Wilson B C and Patterson M S The physics, biophysics and technology of photodynamic therapy Phys. Med. Biol. 53 R61-109. 2008.
Yamamoto, J., et al., "Monitoring of Singlet Oxygen Is Useful for Predicting the Photodynamic Effects in the Treatment for Experimental Glioma," Clinical Cancer Research, vol. 12, Issue 23, Dec. 2006, pp. 7132-7139.
Yu, G., et al., "Noninvasive monitoring of murine tumor blood flow during and after photodynamic therapy provides early assessment of therapeutic efficacy," Clinical Cancer Research, vol. 11, No. 9, May 2005, pp. 3543-3552.
Zhou X, Pogue B W, Chen B, Demidenko E, Joshi R, Hoopes J and Hasan T Pretreatment photosensitizer dosimetry reduces variation in tumor response Int. J. Radiat. Oncol. Biol. Phys. 64 1211-20. 2006.
Zhu et al., The role of photodynamic therapy (PDT) physics, Medical physics 35.7Part1 (2008): 3127-3136.
Zhu T C and Finlay J C Prostate PDT dosimetry Photodiag. Photodyn. Ther. 3 234-46.2006.
Zhu T C, Dimofte A, Hahn S M and Lustig R A Light dosimetry at tissue surfaces for small circular fields Proc. SPIE 4952 56-67.2003.
Zhu, T.C., "In-vivo singlet oxygen threshold doses for PDT," Photonics and Lasers in Medicine, vol. 4, No. 1, Feb. 2015, pp. 59-71.
Zhu, T.C., et al., "Macroscopic Modeling of the singlet oxygen production during PDT," Proc. SPIE 6427, Optical Methods for Tumor Treatment and Detection: Mechanisms and Techniques in Photodynamic Therapy XVI, 642708 (Mar. 6, 2007).
Zhu., T.C., et al., "Study of tissue oxygen supply rate in a macroscopic photodynamic therapy singlet oxygen model," Journal of Biomedical Optics, vol. 20, No. 3, Mar. 2015, 038001-1-038001-13.
Agostinis P., Berg K., Cengel K. A., et al., "Photodynamic therapy of cancer: an update," CA: a cancer journal for clinicians 61(4), 250-81 (2011).
Allison, R.R., et al., "Photodynamic Therapy (PDT): PDT Mechanisms," Clinical Endoscopy, vol. 46, No. 1, Jan. 2013, pp. 24-29.
Attix, F.H., "Exponential Attenuation," Introduction to Radiological Physics and Radiation Dosimetry, Chapter 3, Wiley, Nov. 19, 1986, pp. 38-60.
B. Liu et al., "Comparison of PDT parameters for RIF and H460 tumor models during HPPH-mediated PDT," Proc. SPIE 8931 8931 IC (2014).
Busch T M et al Hypoxia and photofrin uptake in the intraperitoneal carcinomatosis and sarcomatosis of photodynamic therapy patients Clin. Cancer Res. 10 4630-8. 2004.
Castano A. P., Demidova T. N., Hamblin M. R., "Mechanisms in photodynamic therapy: part one-photosensitizers, photochemistry and cellular localization," Photodiagnosis and photodynamic therapy 1(4), 279-93 (2004).

(56) References Cited

OTHER PUBLICATIONS

Chen, B., et al., "Tumor Vascular Permeabilization by Vascular-Targeting Photosensitization: Effects, Mechanism, and Therapeutic Implications," Clinical Cancer Research, vol. 12, Issue 3, Feb. 2006, pp. 917-923.
Diamond K R, Patterson M S and Farrell T J Quantification of fluorophore concentration in tissue-simulating media by fluorescence measurements with a single optical fiber Appl. Opt. 42 2436-42. 2003.
Dougherty, T.J., "Photodynamic therapy," Journal of the National Cancer Institute, vol. 90, Issue 12, Jun. 17, 1998, pp. 889-905.
Du, K.L., et al., "Extrapleural pneumonectomy, photodynamic therapy and intensity modulated radiation therapy for the treatment of malignant pleural mesothelioma," Cancer Biology & Therapy, vol. 10, No. 5, Sep. 1, 2010, pp. 425-429.
Durduran et al, "Diffuse optics for tissue monitoring and tomography", Rep. Prag. Phys., Jun. 2, 2010, 73, 076701.
Finlay J C and Foster T H Recovery of hemoglobin oxygen saturation and intrinsic fluorescence with a forward-adjoint model Appl. Opt. 44 1917-33.2005.
Finlay J C, Conover D L, Hull E L and Foster T H Porphyrin bleaching and PDT-induced spectral changes are irradiance dependent in ALA-sensitized normal rat skin in vivo J. Photochem. Photobiol. 73 54-63.2001.
Finlay J C, Zhu T C, Dimofte A, Friedberg J S and Hahn S M a Diffuse reflectance spectra measured in vivo in human tissues during Photofrin-mediated pleural photodynamic therapy Proc. SPIE 6139 61390.2006.
Finlay J C, Zhu T C, Dimofte A, Stripp D, Malkowicz S B, Busch T M and Hahn S M b Interstitial fluorescence spectroscopy in the human prostate during motexafin lutetium-mediated photodynamic therapy J. Photochem. Photobiol. 82 1270-8.2006.
Friedberg J S et al Extended pleurectomy-decortication-based treatment for advanced stage epithelial mesothelioma yielding a median survival of nearly three years Ann. Thoracic Surg. 103 912-9.2017.
Friedberg, J.S., "Photodynamic therapy and the evolution of a lung-sparing surgical treatment for mesothelioma," The Annals of Thoracic Surgery, vol. 91, No. 6, Jun. 2011, pp. 1738-1745.
Friedberg., J.S., et al., "Radical Pleurectomy and Intraoperative Photodynamic Therapy for Malignant Pleural Mesothelioma," The Annals of Thoracic Surgery, vol. 93, No. 5, May 2012, pp. 1658-1665.
Gardner C M, Jacques S L and Welch A J Fluorescence spectroscopy of tissue: recovery of intrinsic fluorescence from measured fluorescence Appl. Opt. 35 1780-92.1996.
Gross S A and Wolfsen H C The role of photodynamic therapy in the esophagus Gastrointest. Endosc. Clin. North Am. 20 35-53. 2010.
H Qiu, MM. Kim, R Penjweini, JC. Finlay, TM. Busch, T Wang, W Guo, KA Cengel, C B. Simone II, E Glatstein and T C. Zhu."A Comparison of Dose Metrics to Predict Local Tumor Control for Photofrin-mediated Photodynamic Therapy". Photochemistry and Photobiology, 2017, 93: 1115-1122.
H. W. Wang et al., "Effect of photosensitizer dose on fluence rate responses to photodynamic therapy," Photochem. Photobiol. 83(5), 1040-1048 (2007).
Hahn S M, Putt M E, Metz J, Shin D B, Rickter E, Menon C, Smith D, Glatstein E, Fraker D L and Busch T M Photofrin uptake in the tumor and normal tissue of patients receiving intraperitoneal photodynamic therapy Clin. Cancer Res. 12 5464-70.2006.
Hu X. H., Feng Y., Lu J. Q., et al., "Modeling of a type II photofrinmediated photodynamic therapy process in a heterogeneous tissue phantom," Photochemistry and photobiology 81(6), 1460-8 (2005).
Huang Z A review of progress in clinical photodynamic therapy Technol. Cancer Res. Treat. 4 283-93.2005.
Irwin, D., et al., "Influences of tissue absorption and scattering on diffuse correlation spectroscopy blood flow measurements," Biomedical Optics Express, vol. 2, Issue 7, Jul. 1, 2011, pp. 1969-1985.

Jarvi M T, Patterson M S and Wilson B C Insights into photodynamic therapy dosimetry: simultaneous singlet oxygen luminescence and photosensitizer photobleaching measurements Biophys. J. 102 661-71.2012.
Jarvi, M. T., "Singlet oxygen luminescence dosimetry (SOLD) for photodynamic therapy: current status, challenges and future prospects," Photochemistry and Photobiology, vol. 82, No. 5, Sep. 2006, pp. 1198-1210.
K. K. Wang et al., "Explicit dosimetry for photodynamic therapy: macroscopic singlet oxygen modeling," J. Biophoton. 3(5-6), 304-318 (2010).
Kim M M, Darafsheh A, Ahmad M, Finlay J C and Zhu T C PDT dose dosimeter for pleural photodynamic therapy Proc. SPIE 9694 96940.2016.
Kim M M, Penjweini R, Liang X and Zhu T C Explicit macroscopic singlet oxygen modeling for benzoporphyrin derivative monoacid ring a (BPD)-mediated photodynamic therapy J. Photochem. Photobiol. B 164 314-22.2016.
Kim, M., et al., "Singlet oxygen explicit dosimetry to predict long-term local tumor control for BPD-mediated photodynamic therapy," Proc. SPIE 10047, Optical Methods for Tumor Treatment and Detection: Mechanisms and Techniques in Photodynamic Therapy XXVI, 100470X, Feb. 13, 2017.
Lambson K, Liang X, Sharikova A V, Zhu T C and Finlay J C theorectical and experimental examination of fluorescence in enclosed cavities Proc. SPIE 8568 85680.2013.
Liang, X., et al., "Singlet oxygen dosimetry modeling for photodynamic therapy," Proceedings of SPIE—The International Society for Optical Engineering, vol. 8, No. 2, Feb. 2012, 82100T.
M. M. Kim A A Ghogare, A Greer and T. C. Zhu, "On the in vivo photochemical rate parameters for PDT reactive oxygen species modeling". Phys. Med. Biol. 00(2016) 1-48.
M. M. Kim, R. Penjweini, and T. C. Zhu, "Evaluation of singlet oxygen explicit dosimetry (SOED) for predicting treatment outcomes of benzoporphyrin derivative monoacid ring A (BPD-MA)-mediated photodynamic therapy," J Biomed. Opt. 22(2): 028002 Feb. 10, 2017.
McMillan, D.D., et al., "Parameter determination for singlet oxygen modeling of BPD-mediated PDT," Proc. SPIE 8568, Optical Methods for Tumor Treatment and Detection: Mechanisms and Techniques in Photodynamic Therapy XXII, 856810 (Mar. 13, 2013).
Mesquita et al., Direct measurement of tissue blood flow and metabolism with diffuse optics, Philos Trans A Math Phys Eng Sci. Nov. 28, 2011; 369(1955): 4390-4406.
Middelburg T A, Hoy C L, Neumann H A M, Amelink A and Robinson D J Correction for tissue optical properties enables quantitative skin fluorescence measurements using multi-diameter single fiber reflectance spectroscopy J. Dermatol. Sci. 79 64-73. 2015.
Muller M G, Georgakoudi I, Zhang Q, Wu J and Feld M S Intrinsic fluorescence spectroscopy in turbid media: disentangling effects of scattering and absorption Appl. Opt. 40 4633-46.2001.
Ong Y H and Zhu T C Analytic function for predicting light fluence rate of circular fields on a semi-infinite turbid medium Opt. Exp. 24 26261-81.2016.
Ong Y H, Kim M M, Finlay J C, Dimofte A, Cengel K A and Zhu T C Four-channel PDT dose dosimetry for pleural photodynamic therapy Proc. SPIE 10047 1004717.2017.
Ong, Y., et al., "Photodynamic Therapy Explicit Dosimetry," In book: Recent Advancements and Applications in Dosimetry, Chapter 3, May 2018, pp. 45-72.
Ong, Y.H., et al., "Monitoring and assessment of tumor hemodynamics during pleural PDT," Proc. SPIE 10047, Optical Methods for Tumor Treatment and Detection: Mechanisms and Techniques in Photodynamic Therapy XXVI, Feb. 16, 2017, 100470C-1-100470C-7.
Ong, Y.H., et al., "PDT dose dosimetry for Photofrin-mediated pleural photodynamic therapy (pPDT)," Physics in Medicine & Biology, vol. 63, No. 1, Dec. 29, 2017, 015031.
Ong, Y.H., et al., "Reactive Oxygen Species Explicit Dosimetry (ROSED) of a Type 1 Photosensitizer," Proc. SPIE 10476, Optical

(56) References Cited

OTHER PUBLICATIONS

Methods for Tumor Treatment and Detection: Mechanisms and Techniques in Photodynamic Therapy XXVII, 104760V (Feb. 12, 2018).
Patterson, M. S., B. C. Wilson and R. Graff (1990) In vivo tests of the concept of photodynamic threshold dose in normal rat liver photosensitized by aluminum chlorosulphonated phthalocyanine. Photochem. Photobiol. 51, 343-349.(1990).
Penjweini, R., et al., "Singlet oxygen explicit dosimetry to predict local tumor control for HPPH-mediated photodynamic therapy," Proc. SPIE 10047, Optical Methods for Tumor Treatment and Detection: Mechanisms and Techniques in Photodynamic Therapy XXVI, 1004710, Feb. 8, 2017.
Penjweini, R., Kim, M. M., Liu, B., Zhu, T. C., "Evaluation of the 2-(1-Hexyloxyethyl)-2-devinyl pyropheophorbide (HPPH) mediated photodynamic therapy by macroscopic singlet oxygen modeling," Journal ofBiophotonics 9(11-12), 1344-1354 (2016).
Penjweini, R., Liu, B., Kim, M. M., Zhu, T. C., "Explicit dosimetry for 2-(1-hexyloxyethyl)-2-devinyl pyropheophorbide-a-mediated photodynamic therapy: macroscopic singlet oxygen modeling," Journal of biomedical optics 20(12), 128003 (2015).

\* cited by examiner

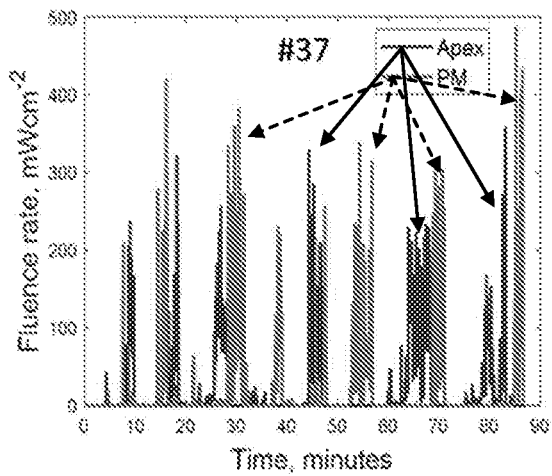 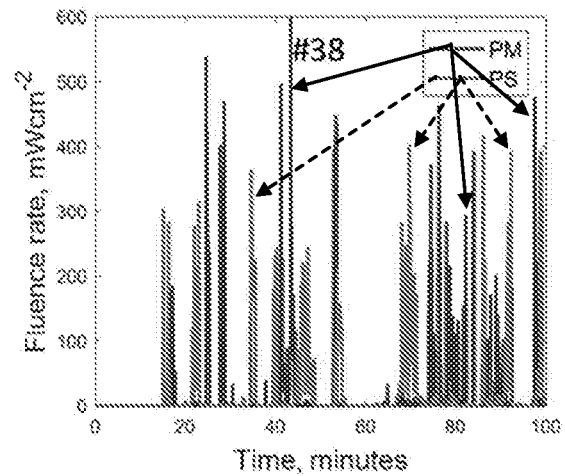
FIG. 17A  FIG. 17B
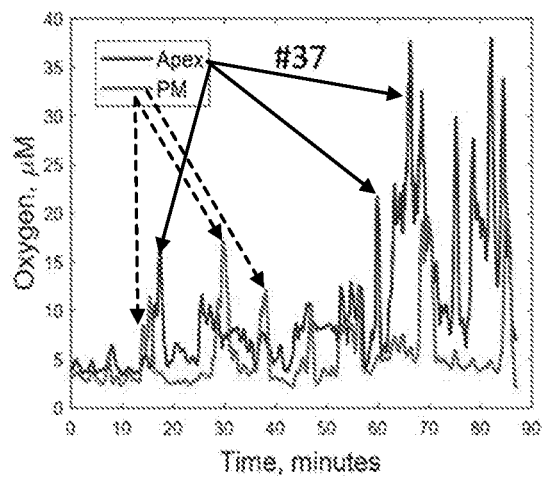 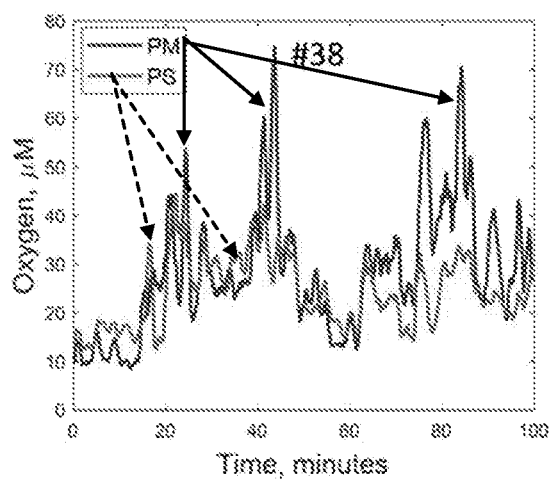
FIG. 17C  FIG. 17D

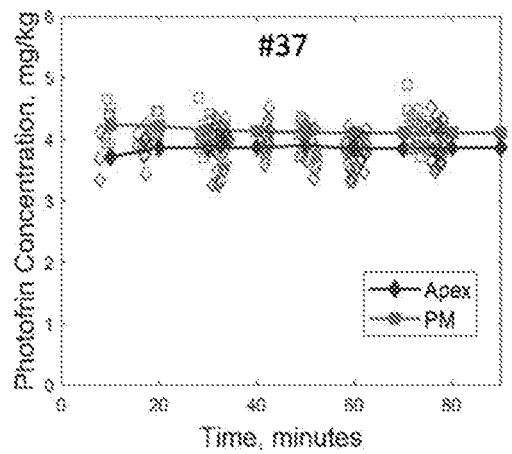 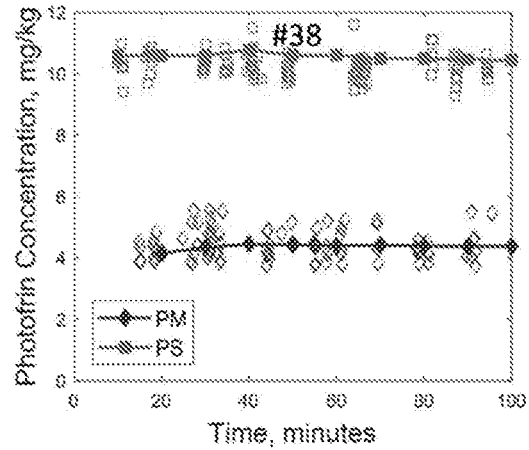
FIG. 17E　　　　　　　　FIG. 17F
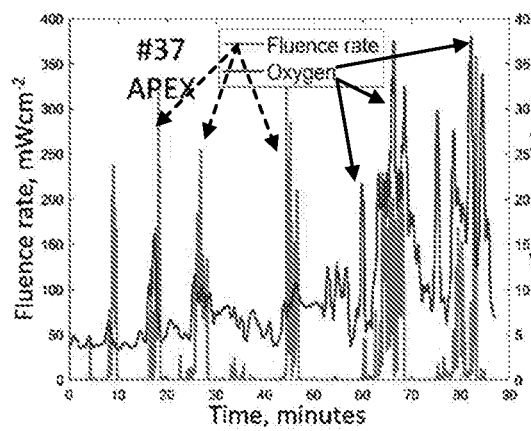 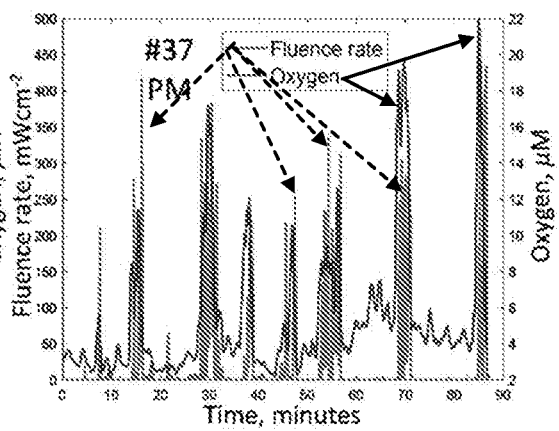
FIG. 17G　　　　　　　　FIG. 17H

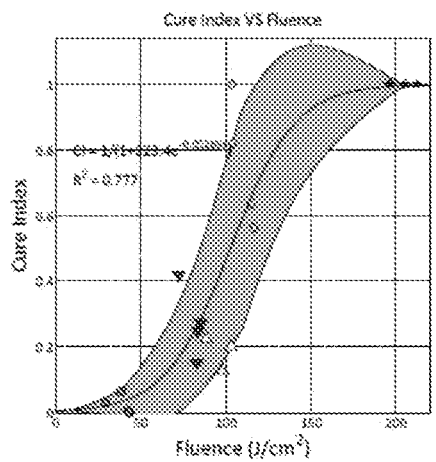 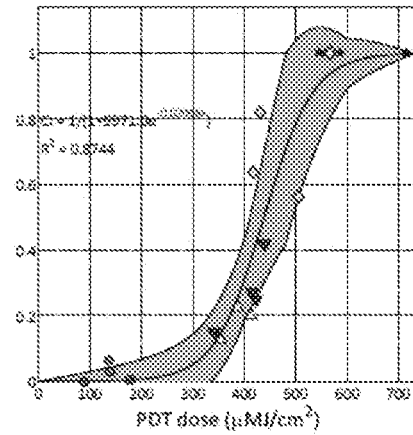
FIG. 23A  FIG. 23B
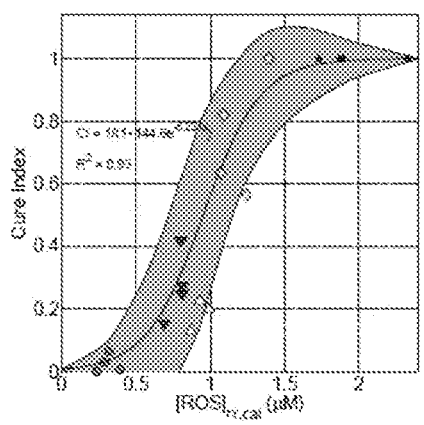 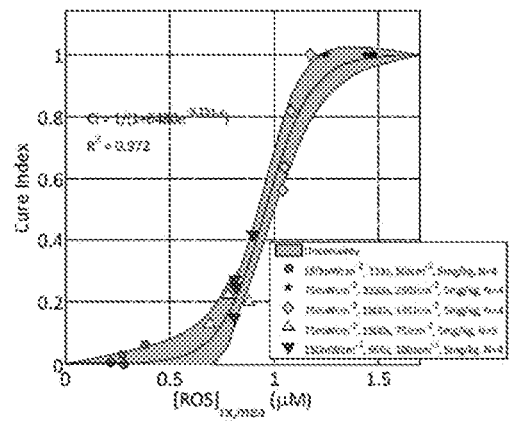
FIG. 23C  FIG. 23D

METHODS AND SYSTEMS FOR PHOTODYNAMIC THERAPY CALCULATIONS

CROSS-REFERENCE TO RELATED APPLICATIONS

This application is the National Stage Application of International Patent Application No. PCT/US2019/060043, filed Nov. 6, 2019, which claims priority to and the benefit of U.S. Patent Application No. 62/756,380 filed Nov. 6, 2018, each of which is hereby incorporated by reference in its entirety for any and all purposes.

GOVERNMENT SUPPORT CLAUSE

This invention was made with government support under CA087971, and CA154562 awarded by the National Institutes of Health. The government has certain rights in the invention.

BACKGROUND

Photosensitizer fluorescence excited by photodynamic therapy (PDT) treatment light can be used to monitor the in vivo concentration of the photosensitizer and its photobleaching. The temporal integral of the product of in vivo photosensitizer concentration and light fluence is called PDT dose, which is an important dosimetry quantity for PDT. However, the detected photosensitizer fluorescence may be distorted by variations in the absorption and scattering of both excitation and fluorescence light in tissue. Therefore, correction of the measured fluorescence for distortion due to variable optical properties is important for absolute quantification of photosensitizer concentration.

SUMMARY

Methods and systems for implementing a photodynamic therapy are disclosed. An example system may comprise a plurality of optical probes configured to be disposed at one or more locations of a patient, the plurality of optical probes each comprising a first optical fiber that is bifurcated into a second optical fiber and a third optical fiber. The system may comprise one or more spectrometers optically coupled to the plurality of optical probes via corresponding second optical fibers, wherein each of the plurality of optical probes is coupled to a different channel of the one or more spectrometers, wherein the one or more spectrometers are configured to generate spectral data based on optical signals from the plurality of optical probes. The system may comprise at least one processor configured to: determine, based on the spectral data, data indicative of a photodynamic therapy dosage associated with a corresponding location; determine, based on optical signals from one or more of the second optical fibers, data indicative of a fluence rate of a photodynamic therapy treatment light associated with a corresponding location; and output, during a photodynamic therapy treatment, one or more of the data indicative of the photodynamic therapy dosage or the data indicative of the fluence rate for a corresponding location.

An example method may comprise determining, during photodynamic therapy and using a plurality of optical probes spatially distributed within a patient, data indicative of one or more of a photodynamic therapy dosage, a fluence rate of a photodynamic therapy treatment light, or a reactive oxygen species concentration associated with corresponding locations of the plurality of optical probes. The method may comprise changing, based on the data, one or more treatment parameters associated with providing a photodynamic therapy.

An example integrated probe may comprise a photodynamic therapy dosage sensor comprising a first optical fiber that is bifurcated into a second optical fiber and a third optical fiber and a blood flow sensor comprising a fourth optical fiber configured to emit a light and one or more fifth optical fibers configured to receive a reflection of the emitted light.

Additional advantages will be set forth in part in the description which follows or may be learned by practice. It is to be understood that both the foregoing general description and the following detailed description are exemplary and explanatory only and are not restrictive.

BRIEF DESCRIPTION OF THE DRAWINGS

The accompanying drawings, which are incorporated in and constitute a part of this specification, illustrate embodiments and together with the description, serve to explain the principles of the methods and systems.

FIG. 17A shows temporal changes in light fluence rate detected on the tissue surface of apex and posterior mediastinum in the pleural cavity of patient #37 during the time course of PDT treatment.

FIG. 17B shows the treatment light fluence rate detected on the tissue surface of posterior mediastinum and posterior sulcus for patient #38.

FIG. 17C show the temporal changes in tumor oxygen measured at the same pleural sites as in FIG. 17A for patient #37.

FIG. 17D show the temporal changes in tumor oxygen measured at the same pleural sites as in FIG. 17B for patient #38.

FIG. 17E shows temporal changes in local Photofrin concentration measured at two pleural sites for patient #37.

FIG. 17F shows temporal changes in local Photofrin concentration measured at two pleural sites for patient #38.

FIG. 17G shows an overlay plot of fluence rate and tumor oxygen taken from the apex location in patient #37.

FIG. 17H shows an overlay plot of fluence rate and tumor oxygen taken from the PM location in patient #37.

FIG. 23A shows cure index plotted as a function of fluence at a 3 mm tumor depth.

FIG. 23B shows cure index plotted as a function of calculated PDT dose at 3 mm tumor depth.

FIG. 23C shows cure index plotted as a function of calculation ROS at 3 mm tumor depth.

FIG. 23D shows cure index plotted as a function of mean reacted singlet oxygen at 3 mm depth ($[ROS]_{rx}$).

DETAILED DESCRIPTION OF ILLUSTRATIVE EMBODIMENTS

Figure 1A:
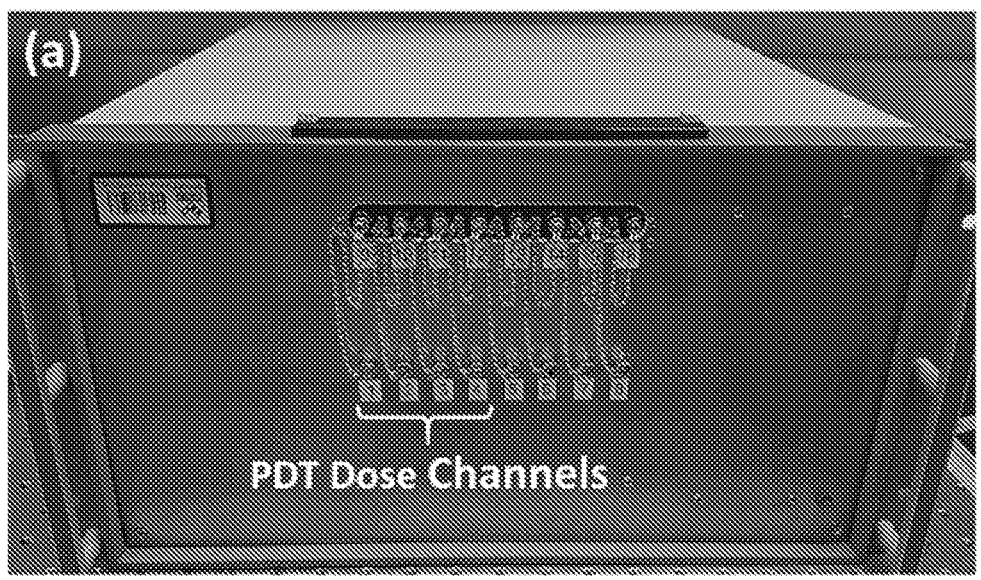
FIG. 1A shows a front view of an example PDT dose dosimetry system.

Disclosed herein is a four-channel PDT dose dosimetry system to simultaneously acquire light dosimetry and photosensitizer fluorescence data. We measured PDT dose at four sites in the pleural cavity during pleural PDT. We have determined an empirical optical property correction function using Monte Carlo simulations of fluorescence for a range of physiologically relevant tissue optical properties. Parameters of the optical property correction function for Photofrin fluorescence were determined experimentally using tissue-simulating phantoms. In vivo measurements of photosensitizer fluorescence showed negligible photobleaching of Photofrin during the PDT treatment, but large intra- and inter-patient heterogeneities of in vivo Photofrin concentration are observed. PDT doses delivered to 22 sites in the pleural cavity of 8 patients were different by 2.9 times intra-patient and 8.3 times inter-patient.

1. Introduction

Type II photodynamic therapy (PDT) is a treatment based on the generation of highly reactive singlet oxygen (1O2) through the interactions of light, photosensitizer (PS), and oxygen (3O2). PDT has been approved by the U.S. Food and Drug Administration to treat patients with a variety of cancers and precancers including esophageal cancer and non-small cell lung cancer as well as Barrett's esophagus, a precancerous lesion that can lead to esophageal cancer (Huang 2005, Triesscheijn et al 2006, Zhu and Finlay 2006). Although PDT has emerged as a viable minimally-invasive treatment modality for a variety of malignant and premalignant conditions, many clinical PDT treatment outcomes are suboptimal due to the lack of a reliable dose metric which will effectively predict treatment outcomes (Weersink et al 2005, Gross and Wolfsen 2010, Penjweini et al 2016, Qiu et al 2017, Kim et al 2017a). Tremendous amounts of research have been done over the past three decades to understand the underlying biophysical mechanism of PDT in the effort to establish a robust dosimetry method (Kim et al 2017a).

Future use of PDT depends on the development of improved dosimetry methods. Defining a PDT treatment dose can be complex since it involves a combination of local light fluence, local PS concentration, and local tissue oxygenation, which are highly interdependent and dynamic. Inadequate treatment doses may lead to insufficient treatment with residual dysplasia or carcinoma, while excessive doses may result in severe damage to the surrounding healthy tissues. Currently, most PDT treatments have been performed based on administered PS dosage and delivered light fluence (Wilson and Patterson 2008, Zhu and Finlay 2008, Jarvi et al 2012). Zhou et al (2006) reported animal-to-animal variation in PDT treatment response due to large intra- and inter-animal variations in PS uptake for benzoporphyrin derivative monoacid ring A (BPD-MA)-mediated PDT. The variation in treatment response was reduced when PDT dose, defined as the product of PS concentration and light fluence, was kept constant among animals. These results for BPD are consistent with our recent studies (Kim et al 2016b, 2017b).

When PDT treatment is delivered with fixed incident light dose, the PDT dose delivered between sites can vary markedly due to the large inter- and intra-patient variability in the PS pharmacokinetics and tissue optical properties (Finlay et al 2006b, Ong et al 2017). Our previous work has shown PDT dose to be a better dosimetry quantity than light fluence or PS dose alone for Photofrin-mediated (Qiu et al 2017) and 2-(1-Hexyloxyethyl)-2-devinyl pyropheophorbide-a (HPPH)-mediated (Penjweini et al 2016) PDT treatment. Under well-oxygenated conditions, PDT dose is a good predictor of PDT treatment outcome as it accounts for the variations in local PS concentration and light fluence.

In conjunction with an ongoing Phase II clinical trial of Photofrin-mediated PDT5 (Friedberg et al 2017) for pleural mesothelioma (Simone and Cengel 2014), we have developed an instrument capable of measuring light fluence rate and PS concentration simultaneously during PDT. The goal of pleural PDT is to target the residual microscopic disease on or near the surface of the pleural cavity after surgical resection of the gross disease. PDT is chosen because it kills tumor cells directly through apoptosis and necrosis and by damaging tumor vasculature within a limited depth within target surface, and it also induces an inflammatory reaction capable of stimulating antitumor immune response which contribute to better treatment outcome. Simone and Cengel (2014) Light fluence and Photofrin fluorescence measured at tissue surface are used to calculate the PDT dose delivered to superficial tissue of the pleural cavity. Spatial heterogeneities in delivered PDT dose are observed within and among patients.

Quantifying measurement of fluorescence emission in vivo is difficult due to the influence of the background tissue optical properties. The interplay of absorption and scattering of both excitation and emission light within the tissue can severely alter the measured fluorescence. Variations in tissue optical properties may be mistaken for different PS concentration. However, in our current implementation, the excitation light (630 nm) and emission light (650-700 nm) are close enough that same optical properties at the excitation wavelength (630 nm) can be used to represent the tissue optical properties at both emission and excitation wavelengths. There are several methods in the literature to reduce the effects of tissue optical properties on measured fluorescence, such as specially design optical probes (Diamond et al 2003, Middelburg et al 2015) or by applying a correction to the measured fluorescence based on independent measurements of tissue optical properties (Gardner et al 1996, Muller et al 2001, Finlay and Foster 2005, Finlay et al 2006b, Lambson et al 2013, Sharikova et al 2013, Kim et al 2016a, 2017b, Qiu et al 2016, Penjweini et al 2016). Here, we report an empirical method to eliminate the effects of tissue optical properties on measured fluorescence spectra based on Monte Carlo (MC) modeling of excitation and fluorescence light propagation in tissue. An empirical optical properties correction function is determined such that it corrects the measured fluorescence at any tissue optical properties to the one measured at the reference tissue optical properties. The validity of this optical properties correction approach was tested experimentally using tissue simulating phantoms for a wide range of clinically relevant optical properties. We have determined the parameters in this model experimentally for Photofrin fluorescence detected on the surface with broad beam irradiation similar to the excitation and detection geometries of our Photofrin fluorescence measurement during PDT treatments.

2. Materials and Methods 2.1. Monte Carlo (MC) simulation Monte Carlo (MC) modeling is used to simulate the fluorescence signal collected by an isotropic detector placed on the tissue surface. The range of tissue optical properties simulated (absorption coefficient ($\mu_a$) between 0.1 and 1 cm$^{-1}$ and reduced scattering coefficient ($\mu_s'$) between 5 and 40 cm$^{-1}$) was based on a review of previously published in vivo tissue optical properties (Sandell and Zhu 2011). The MC algorithm used here was written in Matlab (The Mathworks Inc., Natick, MA, USA) as described previously (Lambson et al 2013). This code uses the implicit capture method (Prahl et al 1989) to improve the efficiency of the MC simulation. In the code, we model the tissue in the cavity as a semi-infinite medium with uniform optical properties ($\mu_a$ and $\mu_s'$), scattering anisotropy (g=0.9) and refraction index mismatch (n/n$_2$=1.4). Photons are launched normal to the air-tissue interface along the z direction with initial weight of 1. Specular reflection at the surface, resulting from the refraction index mismatch, is calculated by the Fresnel reflectance for unpolarized light. The code traces each photon step by step from launch through multiple scattering events until it either escapes the medium or falls below a threshold weight, triggering a random 'roulette' process in which a photon has a one in ten chance of surviving with ten times its initial weight and a nine in ten chance of being terminated. At the end of each step, the weight of the photon is reduced by a factor of 1−a', where a'=$\mu_s'/(\mu_a+\mu_s')$. The photon's new direction is determined based on the Henyey-Greenstein phase function with anisotropy g=0.9.

To model fluorescence, assuming homogeneous fluorophore distribution in the medium, a new fluorescence photon with a weight 1/100 the weight of the incoming photon is generated at each step and is followed by the same algorithm until it escapes the medium or is terminated. The MC code records the distribution of light fluence rate in the medium ($\varphi$), the diffuse components of the reflected light (Rd) and the fluorescence light at the surface ($F_{MC}$) in a cylindrical geometry comprising (e.g., or consisting of) rings of thickness dz and width dr. Reciprocity theorem is used to calculate the $\varphi$, $R_d$, and $F_{MC}$ on the central axis of a circular field as a function of radius R as described elsewhere (Attix 1986, Zhu et al 2003, Ong and Zhu 2016). The magnitude of $\varphi$, $R_d$, and $F_{MC}$ are normalized to the light fluence rate in-air ($\varphi_{air}$), which is proportional to the total number of incident photons.

2.2. Patient Treatment and PDT Dose Detection

Figure 1B:
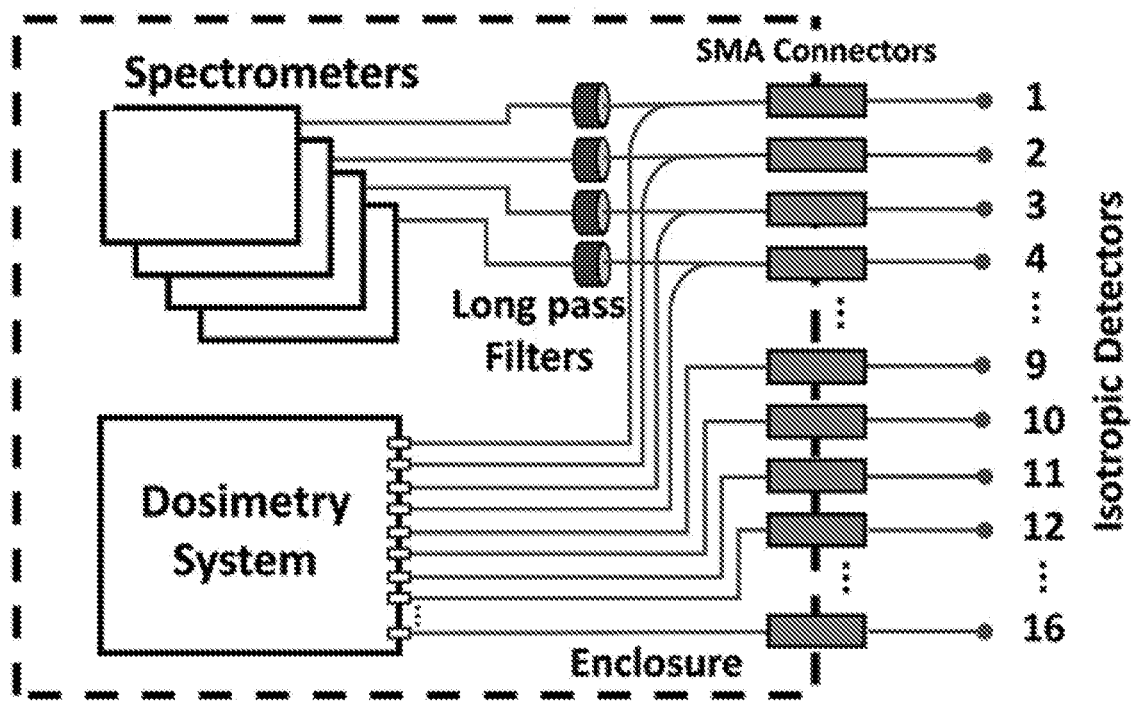
FIG. 1B shows an example schematic diagram of a system setup.

The patients in this study were enrolled in a Phase II randomized clinical trial of Photofrin-mediated PDT for pleural mesothelioma treatment. Having given informed consent, they were administered Photofrin (Pinnacle Biologics, Chicago, IL, USA) at 2 mg kg$^{-1}$ of body weight as an intravenous infusion 24 h prior to intra-operative PDT. PDT was performed in the operating room, immediately following radical pleurectomy and debulking of tumor. PDT treatment was performed with 632 nm light provided by a KTP-pumped dye laser (model 630 XP, Laserscope, Inc., San Jose, CA, USA) to a total fluence of 60 J cm$^{-2}$. Light was delivered to the pleural cavity via an optical fiber inserted into modified endotracheal tube filled with 0.1% intralipid to produce an extended isotropic light source. The pleural cavity was filled with 0.01% intralipid solution during PDT treatment. As the intralipid solution became contaminated with blood as observed by the treating physician, it was repeatedly removed by suction pump and replaced with fresh solution to minimize light absorption by hemoglobin. The light source was circulated around in the lung cavity by the physician during the PDT. The instantaneous light fluence rate and the cumulative light dose were monitored continuously using 8 isotropic detectors (Medlight, Switzerland) sutured to 8 strategic locations within the pleural cavity wall. Light was delivered until the prescribed light dose of 60 J cm$^{-2}$ was reached at each site. Isotropic detectors 1 to 4 were connected to four photodiodes of the multichannel dosimetry system and four spectrometers (Exemplar, B&W Tek, Inc., Newark, DE, USA) via a 1 by 2 bifurcated fiber (Ocean Optics, Dunedin, FL, USA), as shown in FIG. 1B, to monitor the fluence rate of the treatment light and Photofrin fluorescence simultaneously. Each spectrometer has wavelength range of 200 nm-1050 nm and resolution of 0.42 nm using a diode array of 2048×1 elements and 14 µm×200 µm per element. The spectral resolution achieved was 0.47 nm. Isotropic detectors 9 to 12 were connected to the multichannel dosimetry system only. The dosimetry system records light fluence rate using photodiodes. Light fluence rate at surface is measured directly with an isotropic detector placed on the surface. The measured light fluence rate is not reflective of intra-tissue light fluence rate, which may be higher or lower than the value on the tissue surface depending on the tissue optical properties. Fluorescence collected by the fibers was collimated and passed through long pass filters (Semrock, Inc., Rochester, NY, USA) to block the treatment light before the transmitted fluorescence was recorded by the spectrometers, whereas no filtration was required for the treatment-light signal in the other arm of the bifurcated fibers. The front view and the schematic diagram of the system setup are shown in FIGS. 1A-B. There are 16 channels on the system enclosure as shown in FIG. 1A. Channels 9 to 16 (top row) are connected to the dosimetry system only whereas Channels 1 to 4 (bottom row) are connected to both the dosimetry system and the spectrometers. Channels 5 to 8 (bottom row) are currently not used. In this study, Channels 1 to 4 are used to measure fluence rate of the treatment light and Photofrin fluorescence concurrently, while Channel 9 to 12 are used to measure light fluence rate only.

2.3. Optical Properties Measurements

Diffuse reflectance measurements were acquired before and after PDT treatment using a specially designed fiber optic-based contact probe comprising (e.g., or consisting of) one source fiber, coupled to an air-cooled quartz-tungsten-halogen (QTH) lamp (Avalight HAL-S, Avantes, Inc., Louisville, CO, USA), and 9 detection fibers spaced at distances from 1.4 to 8.7 mm from the source. Measurements were made with the probe in contact with the interior surface of the pleural cavity. The reflected light was collected by the detection fibers which are imaged via a spectrograph onto a CCD, to measure radially-resolved diffuse reflectance. Background signal was measured in the same tissue with the white light source turned off, and then subtracted from each measurement. Each tissue spectrum is divided by the spectrum obtained with the same light source and detector in an integrating sphere to account for the wavelength-dependence of the white light source power and CCD response. The diffuse reflectance spectra are fitted with a nonlinear fitting algorithm implemented in the Matlab programming environment to extract the values of tissue optical properties. Details of the probe design and fitting algorithm have been described previously (Finlay et al 2006a).

2.4. Optical Properties Correction 2.4.1. MC Determination of Optical Properties Correction Function MC simulated fluorescence light at the surface was divided by the total light fluence rate on the surface. This normalization is done so that our MC results are consistent with our PDT dose dosimetry results, in which the measured fluorescence was normalized to the fluence rate measured on the tissue surface. Light fluence rate at a tissue surface is calculated based on a previous study (Zhu et al 2003). The normalized MC simulated fluorescence light is referred to as FMC in this paper, and is given by $$F_{MC}(\mu_a, \mu'_s) = \frac{F_{MC,ref}(\mu_{a,ref}, \mu'_{s,ref})}{CF_{MC}(\mu_a, \mu'_s)} \quad (1)$$

To account for the differences in fluorescence due to the variation in optical properties, a set of empirical correction factors, $CF_{MC}$, were computed using the relationship shown in equation (1). $CF_{MC}$ is defined as the ratio of $F_{MC,ref}$ to $F_{MC}$, where $F_{MC,ref}$ is the fluorescence simulated at the reference optical properties ($\mu_{a,ref}$=0.3 cm$^{-1}$ and $\mu'_{s,ref}$=9.6 cm$^{-1}$). The product of $CF_{MC}$ and $F_{MC}$ at any optical properties ($\mu_a$, $\mu'_s$) is equal to $F_{MC,ref}$. The correction factor at the reference optical properties is by definition equal to 1.

The built-in fitting functions in OriginPro 2017 (OriginLab Corp., Northampton, MA, USA) were used to fit CFMC with two independent variables, $\mu_a$ and $\mu_s$. The best fit of data yields a 4-parameter power function of the form:

$$CF = C_1(\mu_a{}^{b1}\mu_a{}'^{b2} + C_2) \quad (2)$$

2.4.2. Experimental Determination of OP Correction Factor for Photofrin Fluorescence A series of tissue mimicking phantoms with Photofrin concentration of 3 mg kg$^{-1}$ and a range of optical properties ($\mu_a$=0.1-0.9 cm$^{-1}$ and $\mu'_s$=5-24 cm$^{-1}$) were used to determine the correction factor for Photofrin fluorescence measured using the 4-channel PDT dosimeter. Intralipid was added as light scatterer and India ink was added as light absorber. The raw fluorescence spectra collected from each spectrometer were fitted to the basis spectra of Photofrin, laser and Fourier components using a single value decomposition (SVD) fitting algorithm described previously (Finlay et al 2001). The SVD amplitude of Photofrin fluorescence was divided by the SVD amplitude of laser to account for the difference in excitation light fluence rate between measurements. The normalized SVD amplitude of Photofrin, referred to as $A_p$ in this paper, is correlated to $F_{MC}$ by a conversion constant $\delta$ ($A_p = \delta \cdot F_{MC}$). $A_p$ was fitted directly using equation (3) to determine parameters $C_1$, $C_2$, $b_1$ and $b_2$.

$$A_p = (\mu_a, \mu'_s) = \frac{A_{p,ref}(\mu_{a,ref}, \mu'_{s,ref})}{CF_p(\mu_a, \mu'_s)} \quad (3)$$

The reference optical properties used in this study were $\mu_{a,ref}=0.3$ cm$^{-1}$ and $\mu'_{s,ref}=9.6$ cm$^{-1}$, close to the mean of the measured tissue optical properties. $A_{p,ref}$ was determined from the average of $A_p$ obtained from Photofrin fluorescence measured at the reference optical properties using four PDT dose channels. The denominator of the term on the right hand side of equation (3) is the optical correction factor for Photofrin in phantoms, and is referred to as $CF_p$ in this paper. To correct for the variation in optical properties in the measured fluorescence, $A_p$ is multiplied by $CF_p$.

2.5. Data Analysis

The raw fluorescence spectra collected during PDT are corrected for the spectral response of the individual spectrometer and analyzed using the SVD fitting algorithm (Finlay et al 2001). This algorithm requires the basis spectra of the known components that comprise the measured fluorescence emission spectrum. The first basis spectrum is the emission of the excitation source that passes through the optical filter. This basis is created by recording the spectrum from a non-fluorescing scattering solution of 20% Intralipid diluted (1:20) in water to 1% concentration, excited with the 630 nm laser used for treatment. A background spectrum, recorded from the same solution with excitation laser turned off in a dark room, was subtracted from the source spectrum. The laser component arises primarily from the autofluorescence of isotropic detector and the low frequency tail of the excitation laser spectrum, which passes the long pass filter. Extensive experiments have been performed to verify the peak at 675 nm is caused by the isotropic detector. The laser component is therefore independent of the sample being measured and can be used as a measure of the excitation light intensity. The second basis spectrum is the fluorescence of Photofrin, measured at a concentration of 3 mg kg$^{-1}$ in the same phantom, with both the excitation source and background spectra subtracted. Each basis spectrum is the average of 10 measurements and is smoothed using a 5-point moving average.

Figure 2:
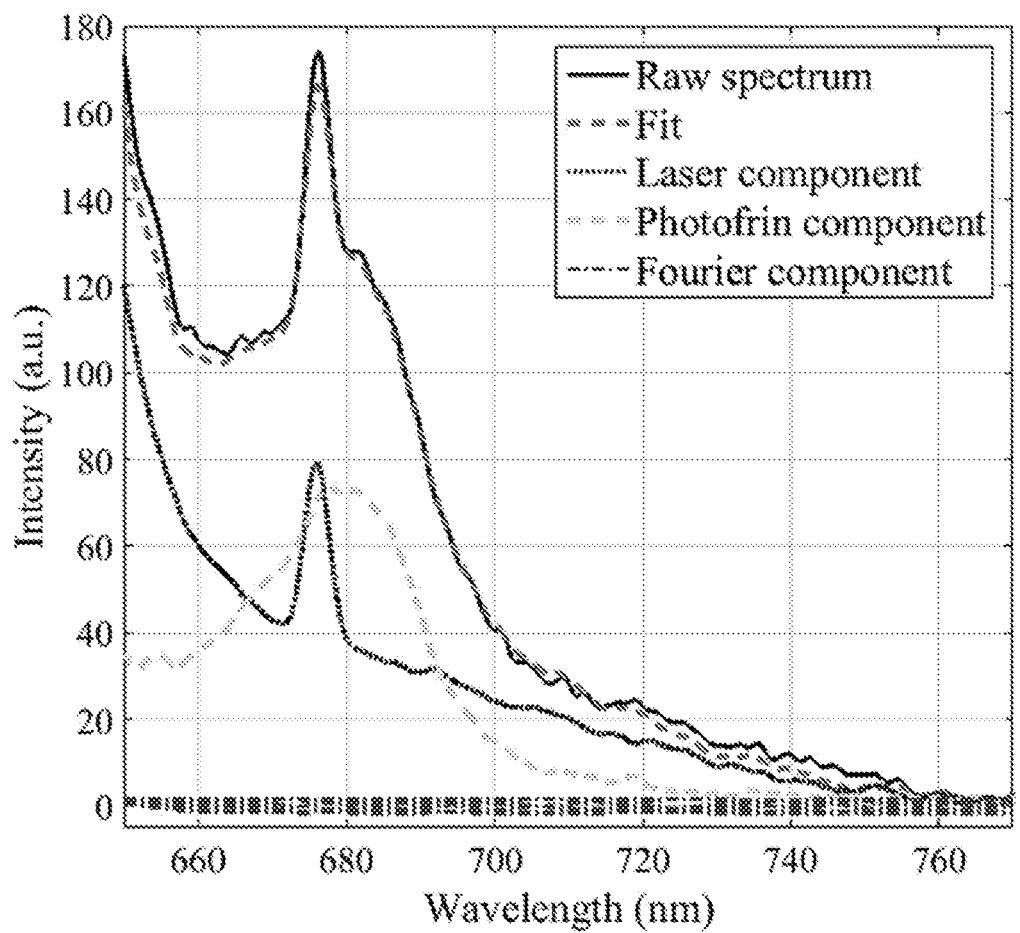
FIG. 2 shows measured raw fluorescence spectrum and its SVD fit using the laser, Photofrin and Fourier basis spectral components.

A 21-term Fourier series is included in the SVD algorithm to account for any unknown spectroscopic components, e.g. tissue autofluorescence and ambient room light, in the measured spectra (Finlay et al 2001). The Fourier components are given a much lower weight in the fitting routine than that of the excitation source and Photofrin components to restrict their application to the unknown components of the spectrum that cannot be fit by combinations of these known components. In the cases presented here, the basis spectra of the two known components adequately account for the measured fluorescence, and the Fourier components constitute only a minor contribution to the fit. Spectra of the basis components and an example of the SVD fit to one fluorescence spectrum measured from patient #020 are shown in FIG. 2.

The SVD fitting algorithm reduces the measured spectrum to a set of unitless SVD amplitudes, one for each basis component. The SVD amplitude of Photofrin is normalized to the SVD amplitude of the laser component to account for the variation in the excitation light fluence rate due to the movement of the treatment light source during PDT treatment. The normalized Photofrin SVD amplitude, after applying the optical properties correction, provides a quantitative measure of the local Photofrin concentration and is regarded as $A_p$ in this paper for the purpose of convenience. The advantage of using $A_p$ value instead of taking the intensity at a particular emission wavelength to quantify local Photofrin concentration is that $A_p$ is less sensitive to noise at individual wavelengths because it is determined by fitting to the entire measured spectrum. The use of SVD value in our application here is particularly advantageous in reducing the uncertainties in the quantification of local Photofrin concentration as a considerable number of the measured fluorescence spectra have low SNR due to the moving excitation light source. The relationship between $A_{p,ref}(CF_p * A_p)$ and Photofrin concentration is obtained through a series of measurements from tissue simulating phantoms with increasing and known Photofrin concentration, as described in section 2.6.

2.6. PDT Dosimeter Calibration and Phantom Verification

Figure 3A:
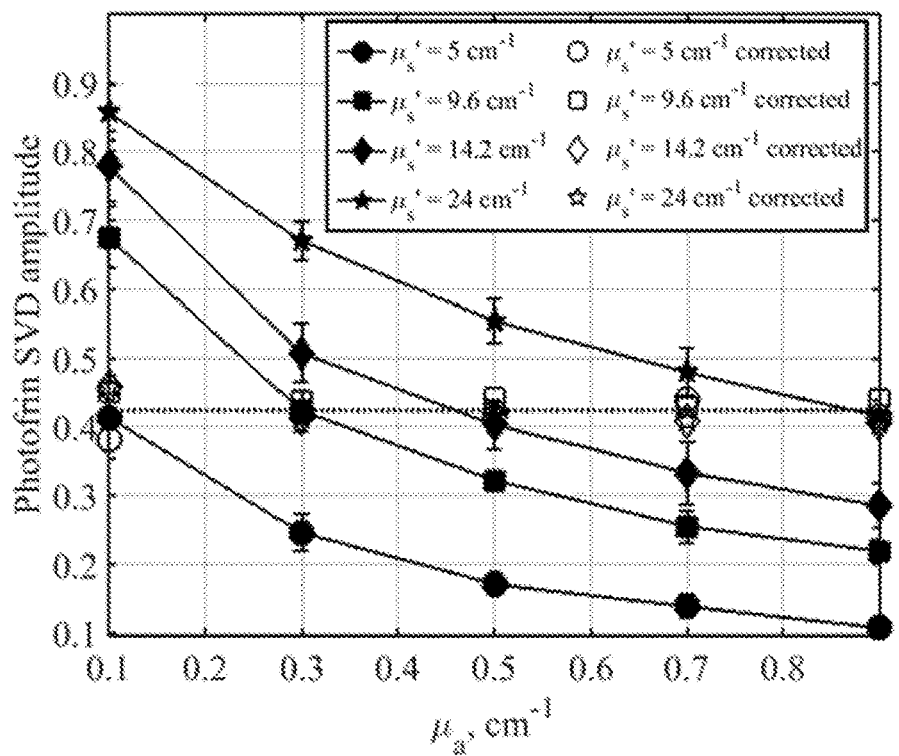
FIG. 3A shows Fluorescence SVD amplitude for Photofrin in tissue-simulating phantom experiments with different optical properties.
Figure 3B:
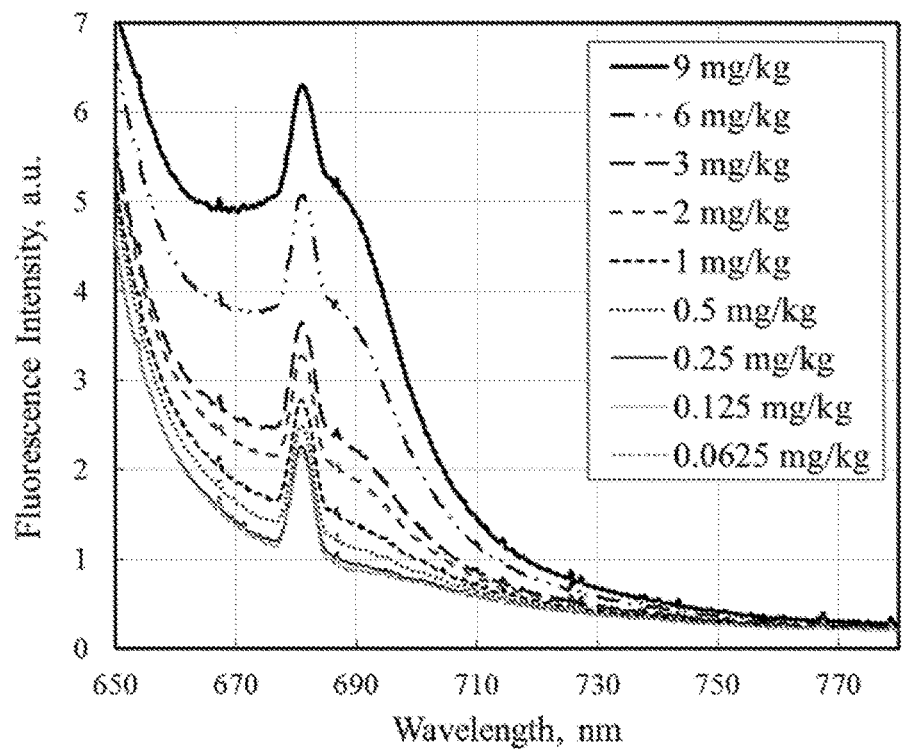
FIG. 3B shows fluorescence spectra of Photofrin at concentrations ranging from 0.0625 mg kg$^{-1}$ to 9 mg kg$^{-1}$ in tissue simulating phantom with $\mu_{a,ref}$=0.3 cm$^{-1}$ and $\mu'_{s,ref}$=9.6 cm$^{-1}$.
Figure 3C:
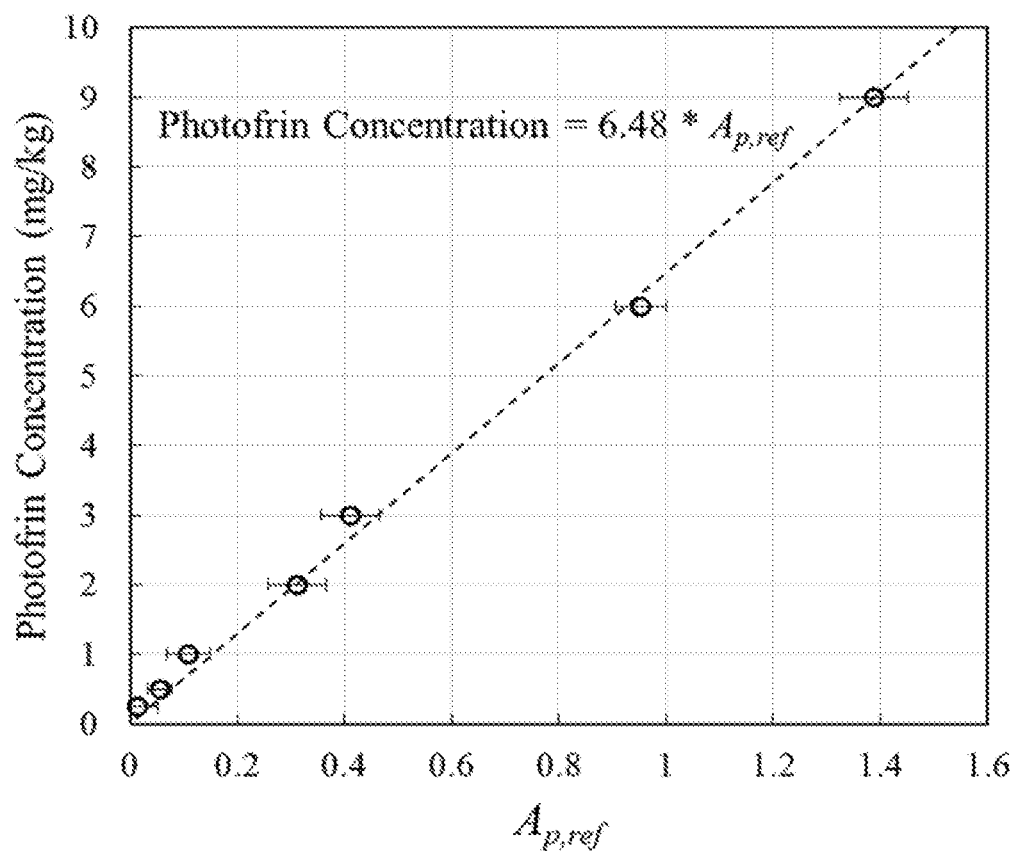
FIG. 3C shows a Photofrin concentration calibration curve.

To quantify absolute in vivo Photofrin concentration, a calibration curve which relates the $A_{p,ref}$ to the concentration of Photofrin was established using tissue simulating phantoms with increasing Photofrin concentration (0.0625 mg kg$^{-1}$ to 9 mg kg$^{-1}$). Fluorescence spectra were measured and processed as described above to obtain a set of $A_{p,ref}$ amplitudes with known concentrations of Photofrin. Fluorescence spectra measured using Channel 1 of the PDT dosimeter are shown in FIG. 3B. Photofrin concentrations of the measured fluorescence are plotted against $A_{p,ref}$ as shown in FIG. 3C. The error bars represent the standard deviation of $A_{p,ref}$ obtained from the fluorescence measured using 4 different PDT dose channels. Photofrin concentration is found to be $A_{p,ref} * 6.48$ mg kg$^{-1}$ and the minimum detectable level of Photofrin concentration of the instrument is 0.5 mg kg$^{-1}$.

Figure 4A:
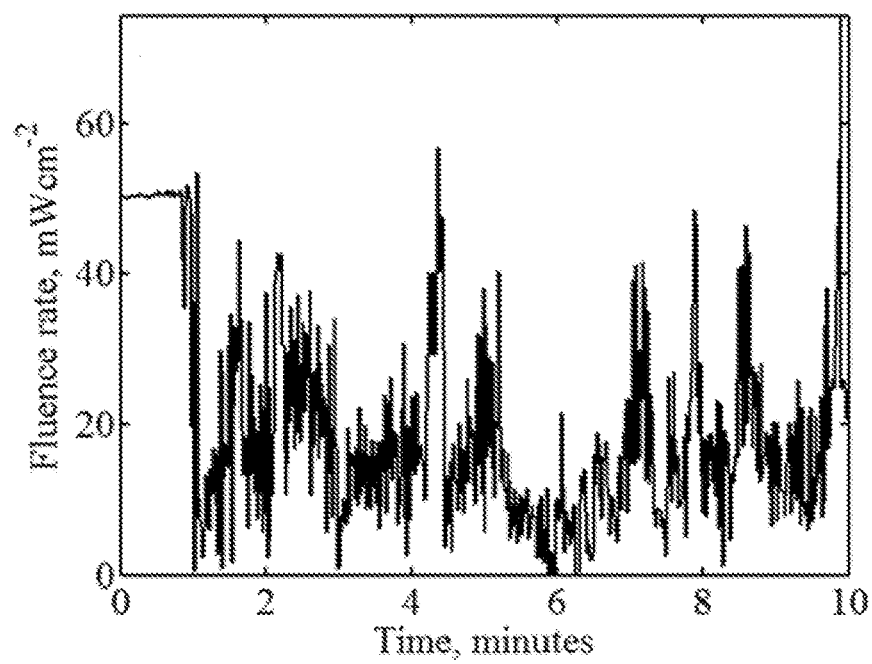
FIG. 4A shows average light fluence rate of 4 channels measured during 10 min of mock treatment.
Figure 4B:
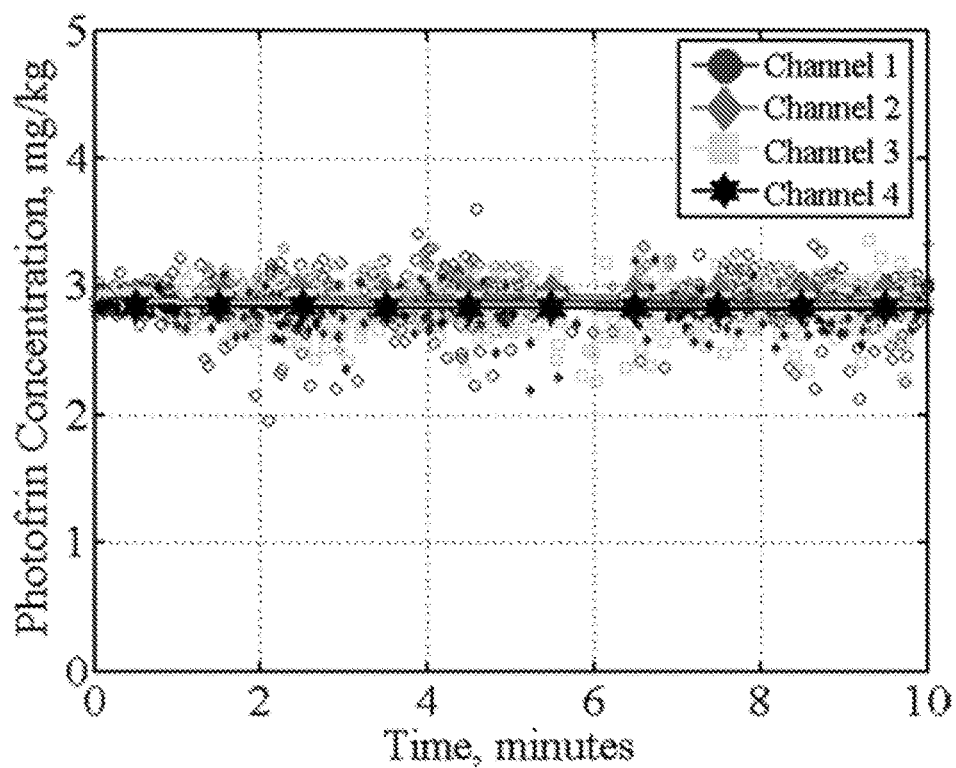
FIG. 4B shows Photofrin concentrations obtained from fluorescence measured using 4 channels.

Excitation light intensity varies vastly during PDT as the light source was constantly circulated around in the lung cavity by the physician. To test the performance of the PDT dosimetry system in measuring Photofrin fluorescence with varying excitation light intensities, a 10 min mock treatment was performed using liquid tissue-simulating phantom ($\mu_a=0.3$ cm$^{-1}$ and $\mu'_s=9.6$ cm$^{-1}$) with known Photofrin concentration of 3 mg kg$^{-1}$ and a moving light source. The fluorescence spectra were measured at the surface of the phantom using isotropic detectors as described above. The treatment started with the treatment light wand positioned at a fixed distance above the phantom for 1 min. The average fluence rate measured on the surface was 50 mW cm$^{-2}$. Then the light wand was moved randomly over the top of the phantom to simulate the variations in the light fluence rate due to the movement of treatment light source in the pleural cavity during PDT treatment. The light fluence rate measured at the surface of the phantom, averaged over the 4 channels, as plotted in FIG. 4A shows constant light fluence rate at 50 mW cm$^{-2}$ for the first minute and varying light fluence rate between 0-70 mW cm$^{-2}$ for the following 9 min. The Photofrin concentrations obtained from measured Photofrin fluorescence spectra using data analysis method described above are plotted as a function of treatment time as shown in FIG. 4B. Each data point represents Photofrin concentration obtained from one fluorescence spectrum and the solid lines represent the average Photofrin concentration calculated for every 1 min of data. The results in FIG. 4B show there is negligible photobleaching of Photofrin during the time course of the measurements. The uncertainty of measurements between channels is around 3% as the Photofrin concentrations recovered from 4 channels vary between 2.84 and 2.92 mg kg$^{-1}$.

2.7. Diffuse Reflectance Measurements

To assess the validity of our fluorescence spectroscopy method, absolute Photofrin concentrations obtained from fluorescence measurements were compared to those obtained from diffuse reflectance spectra measured using DRS contact probe as described in section 2.3 from the same locations before and after PDT treatment. This technique has been validated using phantoms with known PS concentrations (Solonenko et al 2002) and was used to recover PS concentration from in vivo reflectance measurements (Wang et al 2005). Interested readers can refer to Solonenko et al (2002) and Wang et al (2005) for more details about the instrumentation and data analysis of this method. Briefly, a multi-wavelength algorithm based on diffusion approximation equation was employed to fit all reflectance spectra between 600 nm to 800 nm simultaneously using multiple source-detector separations to extract $\mu_a(\lambda)$ and $\mu'_s(\lambda)$. Then, the concentration of Photofrin (and other chromophores) were obtained from $\mu_a(\lambda)$ using $\mu_a(\lambda) = \Sigma_i c_i \in_i(\lambda)$, where $\in_i(\lambda)$ is the extinction coefficient of i'th chromophore and $c_i$ is the molar concentration of the i'th chromophore. The major chromophores in the spectral region of interest are oxy-(HbO2), deoxy-hemoglobin (Hb), water, and Photofrin and their extinction coefficients are obtained from the literature (Wang et al 2005). The concentrations of all chromophores, $c_{water}$, $c_{Hb}$, $c_{HbO2}$ and $c_{Photofrin}$ are reconstructed directly using a nonlinearly constrained optimization method, fminsearch, implemented in Matlab. The spatial distributions of oxy-, deoxy-hemoglobin and water in the pleural cavity are beyond the scope of this study and only cPhotofrin will be reported.

Figure 5A:
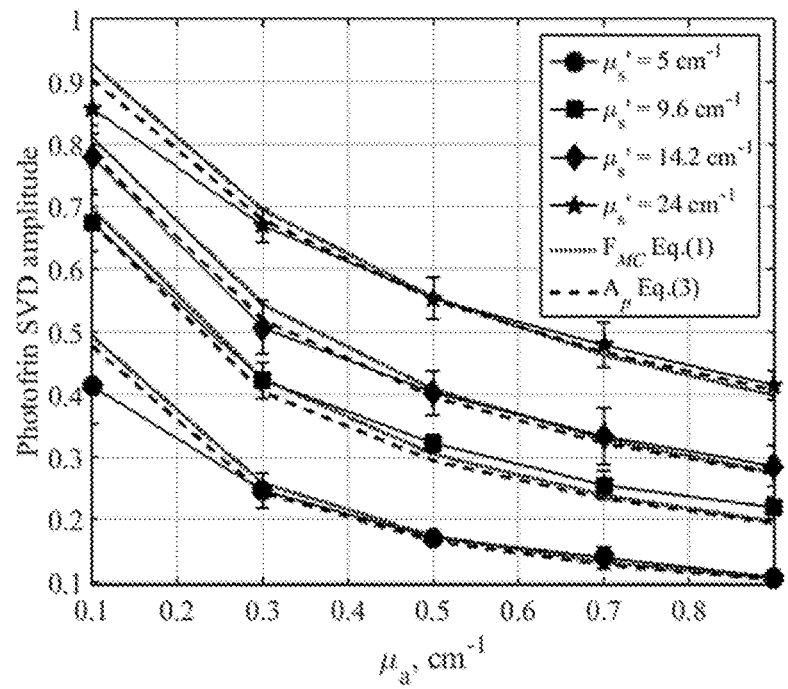
FIG. 5A shows Monte Carlo simulated fluorescence, $F_{MC}$, (dotted lines), average Photofrin SVD amplitude obtained from fluorescence measured in phantoms using 4-channel PDT dosimeter (solid lines) and $A_p$ fits using equation (3) (dashed lines).

3. Results and Discussion 3.1. MC determination of parameters for fluorescence correction MC simulated fluorescence ($F_{MC}$), detected by an isotropic detector placed at the surface of tissue with varying optical properties, are represented by dotted lines in FIG. 5A. A circular beam with radius=7 cm is used in the simulation as the incident light field to represent the broad beam illumination used in the clinic. To facilitate the comparison of MC and experimental results, the amplitudes of $F_{MC}$ are scaled by a constant so that the amplitude of $F_{MC}$ matches that of $A_p$ at the reference optical properties ($\mu_{a,ref}=0.3$ cm$^{-1}$ and $\mu'_{s,ref}=9.6$ cm$^{-1}$). Variations in fluorophore concentration and optical properties can both alter the intensity of the detected fluorescence. To investigate and account for the effect of optical properties alone on the fluorescence intensity, fluorophore concentration is kept constant in all of our simulations. The simulated fluorescence intensity increases with tissue reduced scattering coefficient and decreases with absorption coefficient. A set of correction factors, $CF_{MC}$, is computed using equation (1) to correct for the change in fluorescence intensity due to optical properties so that FMC is equal to value measured at the reference tissue optical properties ($F_{MC,ref}$). We found that equation ($\lambda$) can fit $CF_{MC}$ very well, where $C_1=22.43$, $C_2=0.011$, $b_1=0.943$, and $b_2=-0.973$. The empirical correction factors are plotted as a function of optical properties as represented by dotted lines in FIG. 5(b). Parameters $b_1$ and $b_2$ describe the behavior of the fluorescence alteration due to light scattering and absorption in the tissue while C1 is a scaling factor which accounts for the difference in fluorescence detection efficiency due to spectrometer's sensitivity and optical components along the light path. No optical properties correction is needed for fluorescence measured at the reference optical properties, as CFMC is equal to 1.

We found that the exponential form of correction factor formula suggested in our earlier publication (Sharikova et al 2013, Kim et al 2016a, 2017b, Penjweini et al 2016, Qiu et al 2016) works well within a narrower range of tissue optical properties (absorption coefficients between 0.1 and 1 cm$^{-1}$ and reduced scattering coefficients between 5 and 15 cm$^{-1}$). The exponential form of the correction factor formula is not able to fit the MC results when the reduced scattering coefficient is larger than 15 cm$^{-1}$. The power form of correction factors are used in this study, but it should be noted that the exponential form of correction factors used in earlier publications are valid for the range of reduced scattering coefficient of most measured tissue sites in this study (5.8-16.6 cm$^{-1}$). The correction factors calculated using both the power form, $CF_p$, and exponential form, CFa, are listed in table 2 for comparison.

Figure 5B:
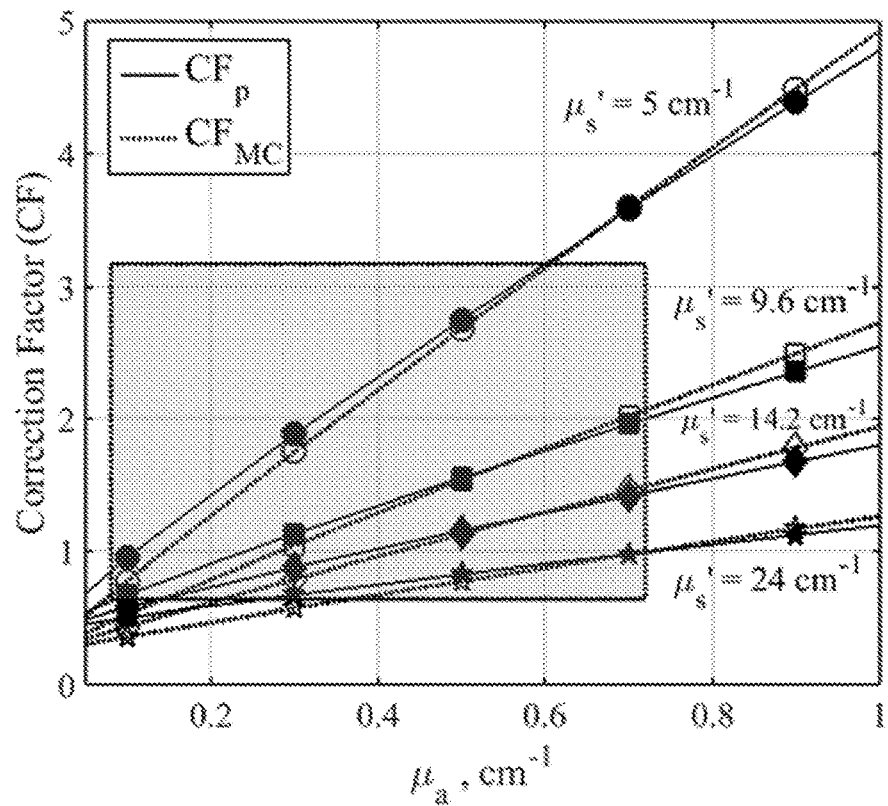
FIG. 5B shows a comparison of $CF_{MC}$ (dotted lines) and $CF_p$ (solid lines).

3.2. Phantom Determination of Parameters for Photofrin Fluorescence Correction Function The average amplitudes of $A_p$ obtained from fluorescence measured in tissue-simulating phantoms using 4 different channels of the PDT dosimeter are represented as solid lines in FIG. 5A. The error bars are the standard deviation of the $A_p$ for 4 different channels. Similar trend in the fluorescence alteration is observed as the amplitude of $A_p$ decreases with absorption coefficient and increases with reduced scattering coefficient. Equation (3) is used to fit $A_p$ using $A_{p,ref}=0.423$ at the reference optical properties ($\mu_{a,ref}=0.3$ cm$^{-1}$ and $\mu'_{s,ref}=9.6$ cm$^{-1}$). The parameters of $CF_p$ are $C_1=25.49$, $C_2=0.016$, $b_1=0.902$, and $b_2=-1.094$ and the empirical CFp are plotted as a function of optical properties in FIG. 5B, represented by solid lines. The fit of $A_p$ using equation (3) are plotted on FIG. 5A for comparison, as represented by the dashed line, and has a goodness of fit of $R^2=0.9608$. The parameters for correction factors obtained from MC simulations and phantom measurements are summarized in table 1.

The empirical correction method described above requires accurate knowledge of the tissue optical properties. As the difference in optical properties at the excitation (630 nm) and emission wavelength (650-700 nm) is rather small in this study, we have applied the correction based on the optical properties at the excitation wavelength of 630 nm obtained from diffuse reflectance spectroscopy measurements. There are significant variations in optical properties inter- and intra-patients according to our measurements. The correction factors used in analyzing our in vivo data correspond to excitation wavelength absorption coefficients of 0.08 to 0.72 cm$^{-1}$ and reduced scattering coefficients of 5.8 to 16.6 cm$^{-1}$, as indicated by the shaded area in FIG. 5B.

TABLE 1

Optical properties correction function parameters.

| Parameters | $C_1$ | $b_1$ | $b_2$ | $C_2$ |
|---|---|---|---|---|
| $CF_{MC}$ | 22.43 | 0.943 | −0.973 | 0.011 |
| $CF_p$ | 25.49 ± 0.65 | 0.902 ± 0.1 | −1.094 ± 0.12 | 0.016 ± 0.05 |

3.3. Tissue Optical Properties and Spatial Distribution of Photofrin

Figure 6A:
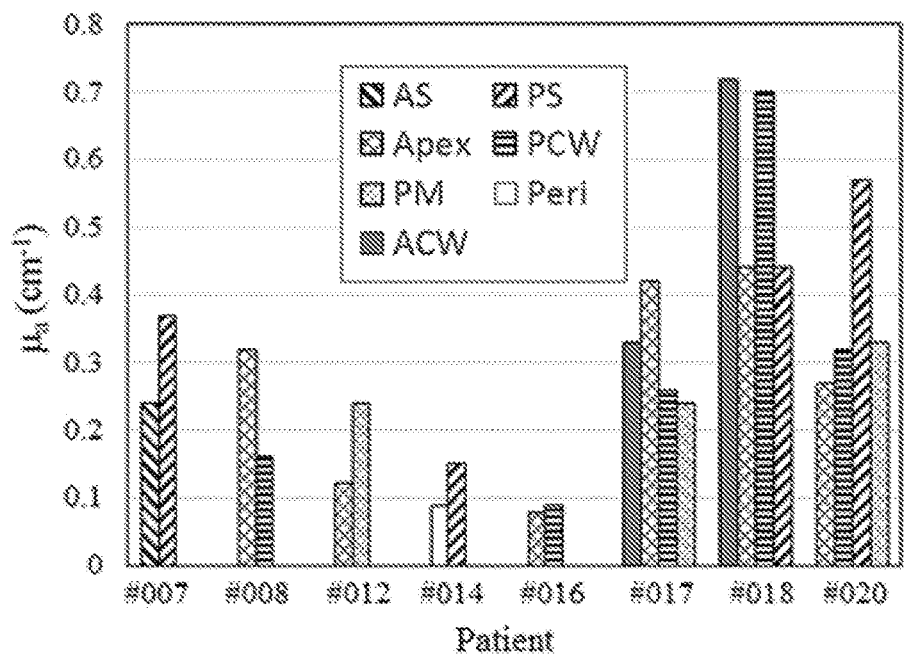
FIG. 6A shows tissue absorption coefficients.
Figure 6B:
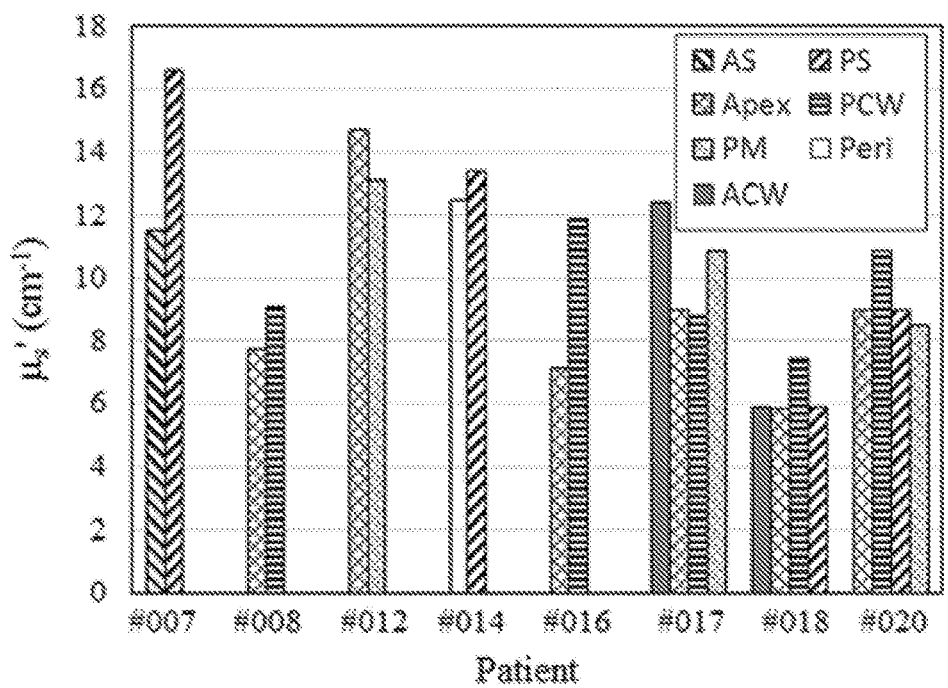
FIG. 6B shows reduced scattering coefficients at excitation wavelength of 630 nm.
Figure 6C:
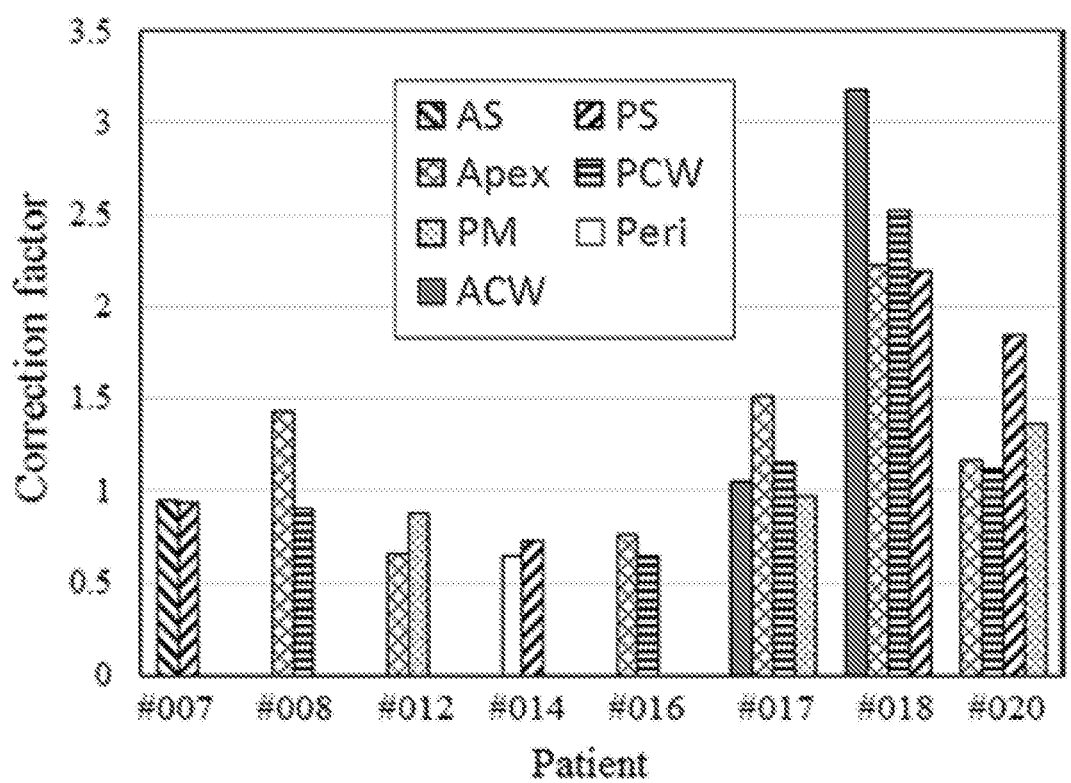
FIG. 6C shows $CF_p$ at 22 different sites in the pleural cavities of 8 patients.
Figure 7A:
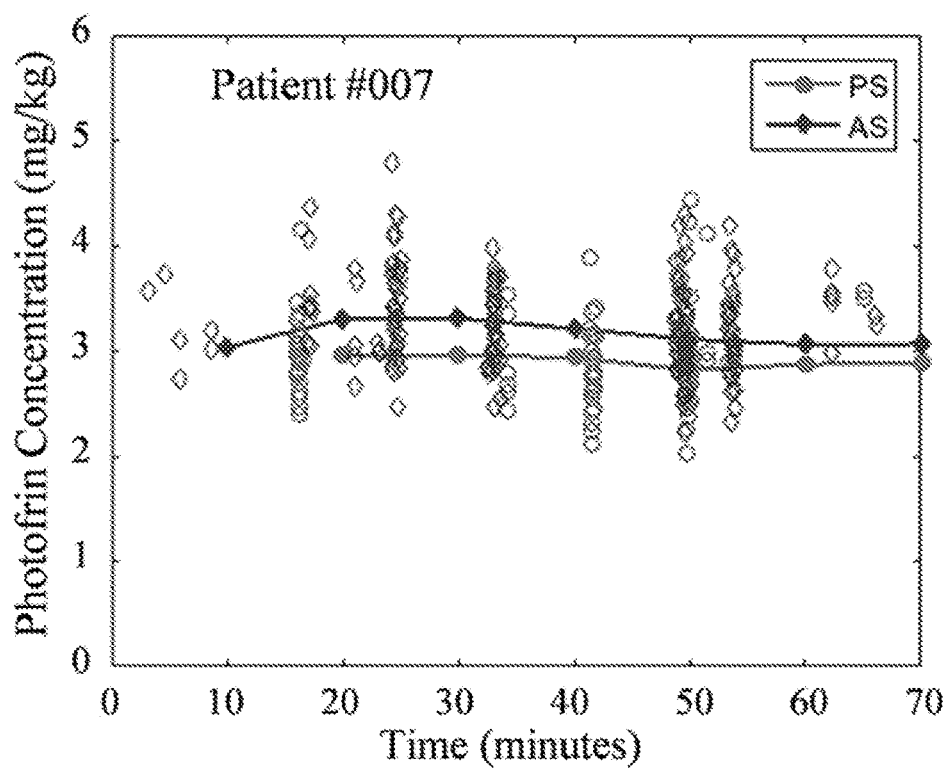
FIG. 7A shows temporal changes of Photofrin concentrations measured from sites in the pleural cavity of patient #007.
Figure 7B:
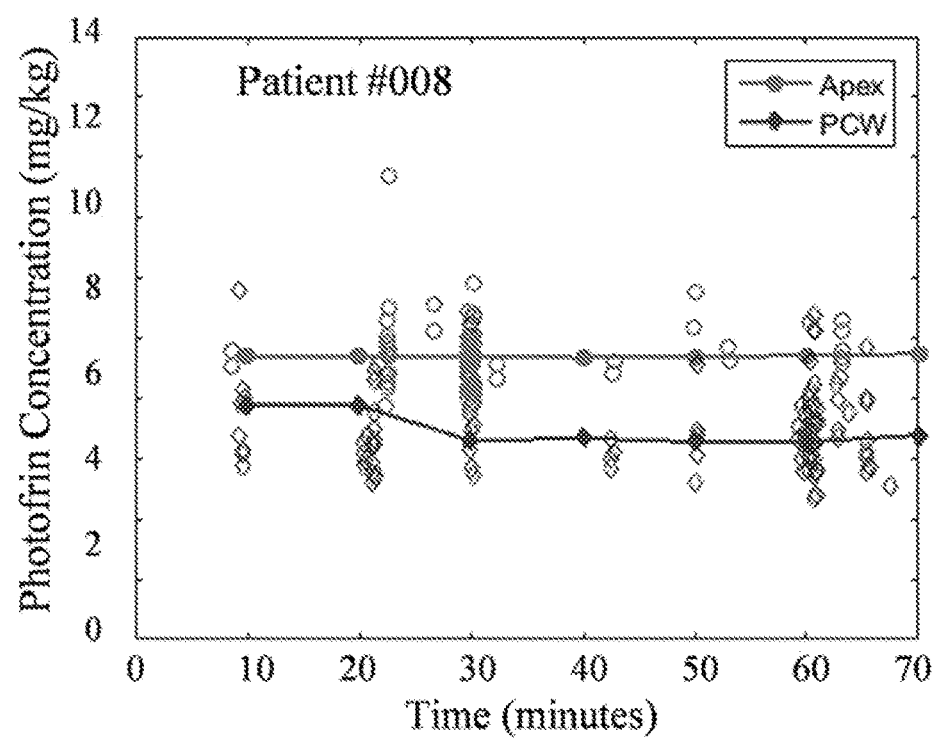
FIG. 7B shows temporal changes of Photofrin concentrations measured from sites in the pleural cavity of patient #008.
Figure 7C:
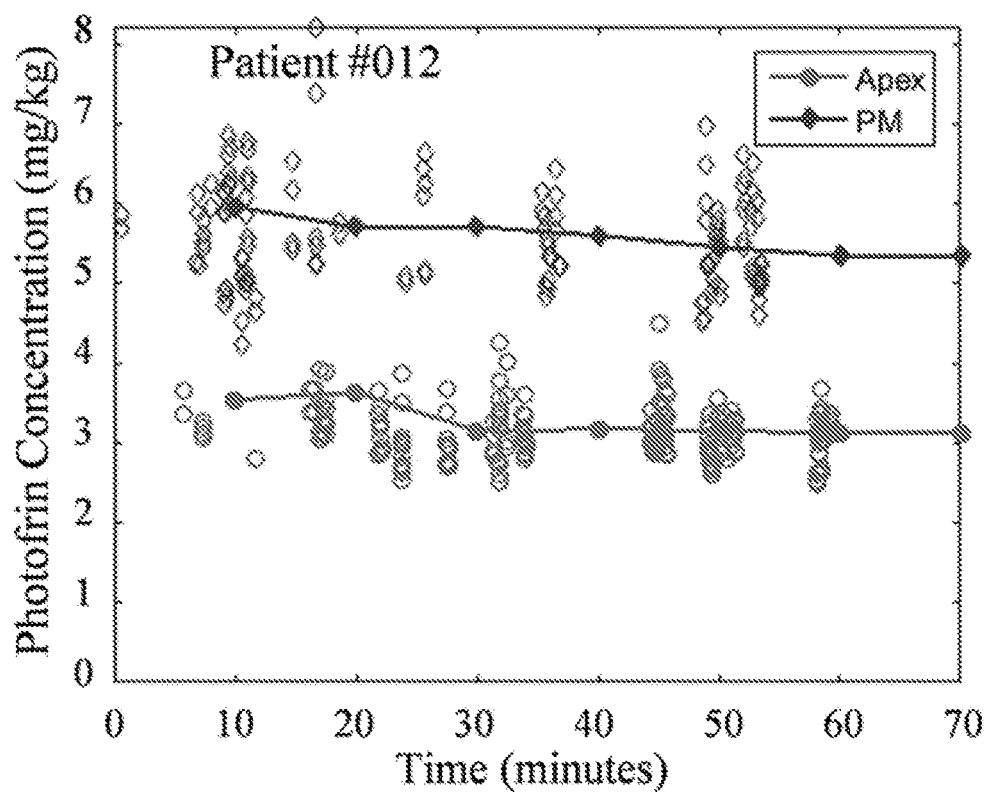
FIG. 7C shows temporal changes of Photofrin concentrations measured from sites in the pleural cavity of patient #012.
Figure 7D:
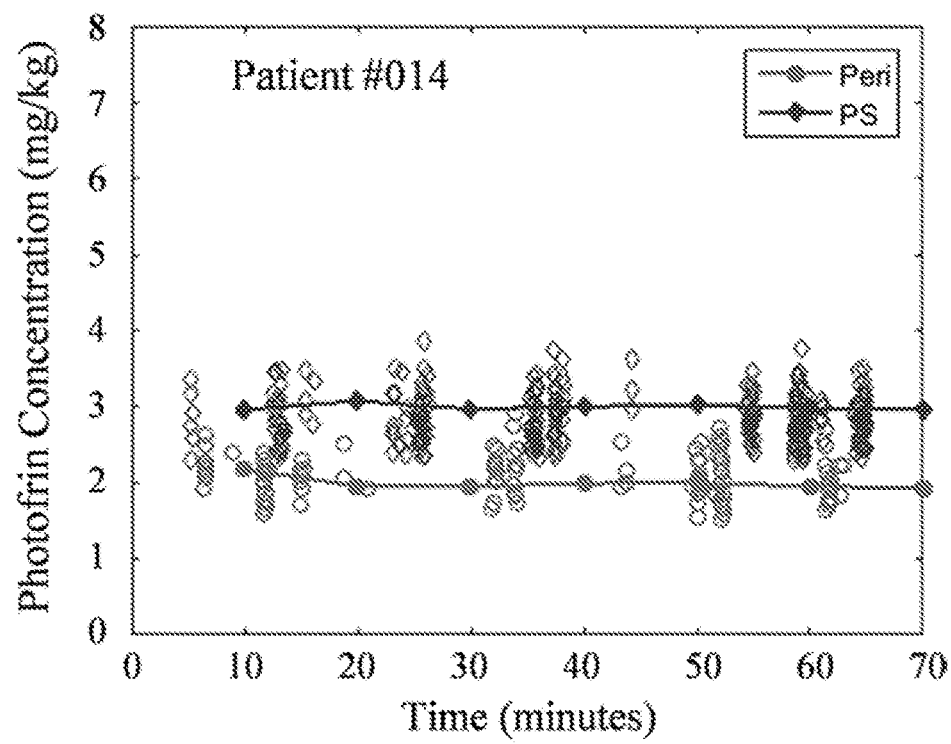
FIG. 7D shows temporal changes of Photofrin concentrations measured from sites in the pleural cavity of patient #014.
Figure 7E:
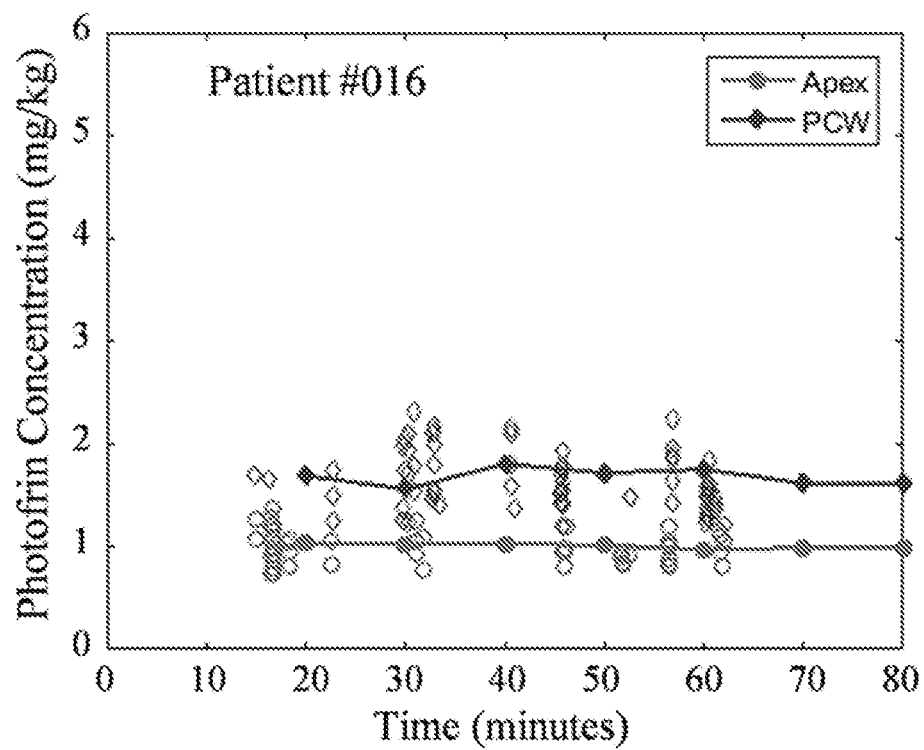
FIG. 7E shows temporal changes of Photofrin concentrations measured from sites in the pleural cavity of patient #016.
Figure 7F:
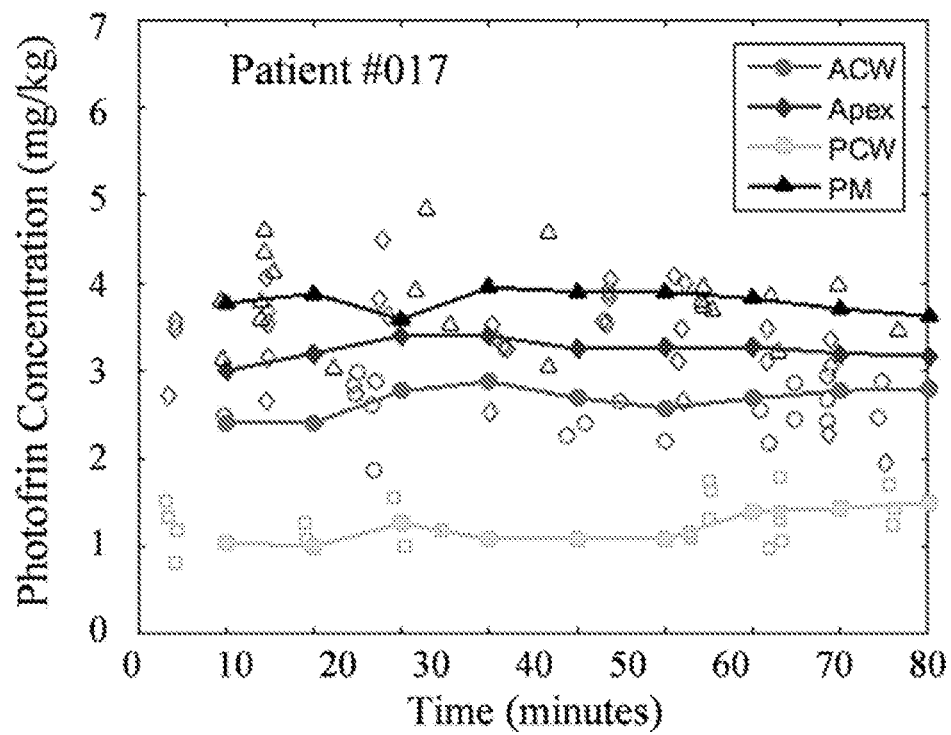
FIG. 7F shows temporal changes of Photofrin concentrations measured from sites in the pleural cavity of patient #017.
Figure 7G:
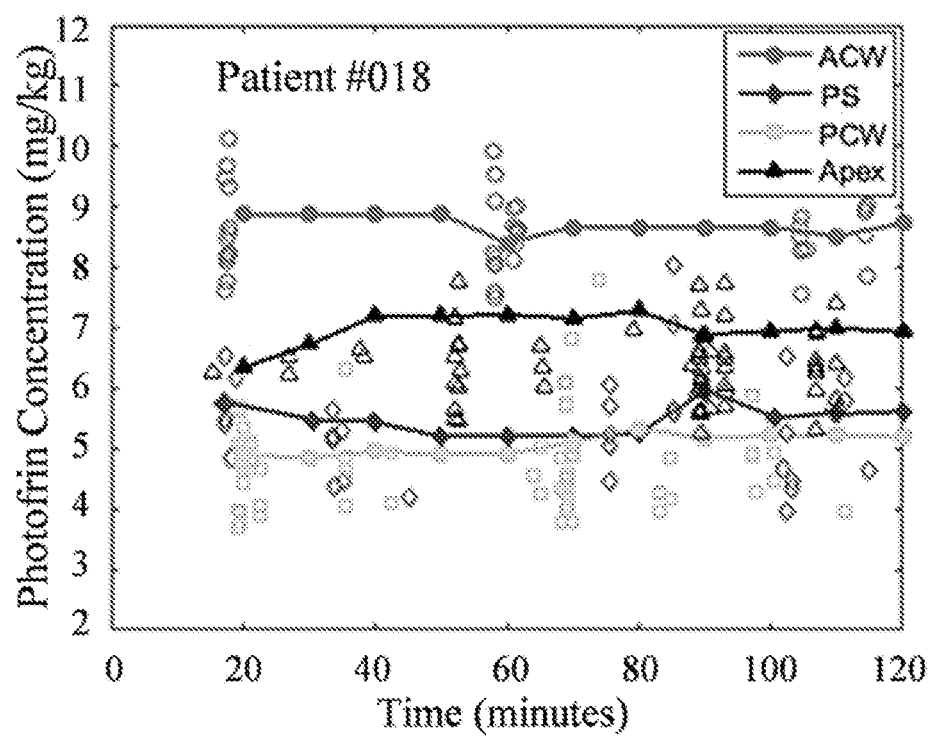
FIG. 7G shows temporal changes of Photofrin concentrations measured from sites in the pleural cavity of patient #018.
Figure 7H:
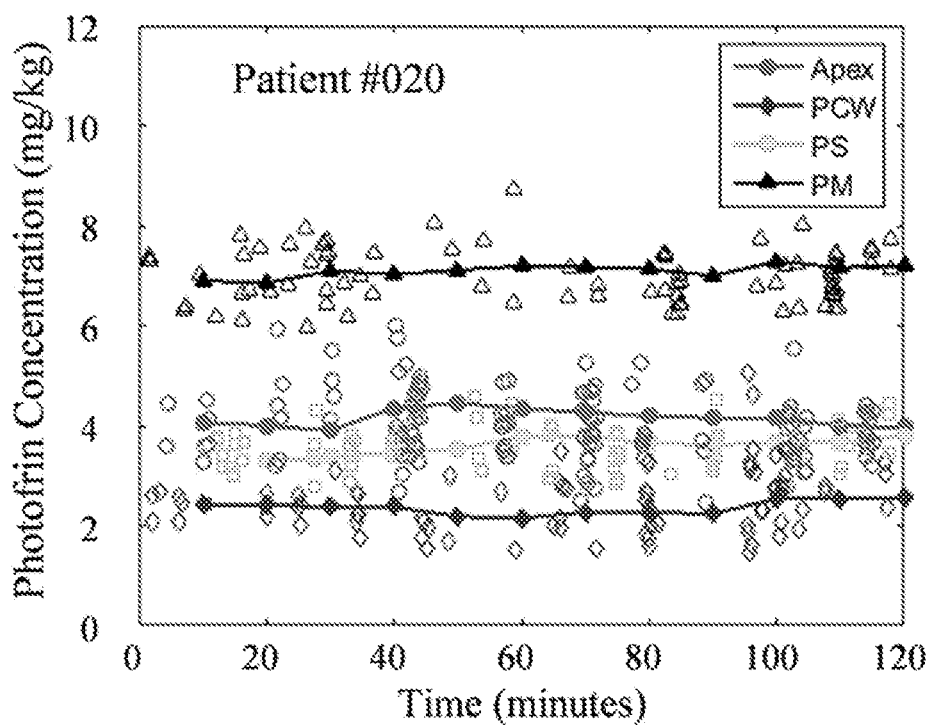
FIG. 7H shows temporal changes of Photofrin concentrations measured from sites in the pleural cavity of patient #020.

In this study, we measured in vivo diffuse reflectance and fluorescence spectra for 22 sites in the pleural cavities of 8 patients. The PDT dose dosimetry system had two channels that were capable of measuring light fluence rate and fluorescence simultaneously for the first 5 patients, later expanded to 4 channels. Tissue absorption and reduced scattering coefficients at excitation wavelength of 630 nm from all measurement sites where fluorescence spectra were taken are presented in FIGS. 6A-C. We saw large heterogeneity in the tissue optical properties within and among patients. The contribution of haemoglobin to the tissue absorption at the emission wavelength, close to the NIR biological window, is rather small. The large spatial heterogeneity in tissue optical properties, especially the high absorption coefficient observed in some patients, could be due to the thermal damage to the measured tissue caused by electrosurgery during tumor resection. FIG. 6C shows correction factors obtained for all sites based on the measured optical properties. The magnitude of correction factors range from 0.59 to 3.13 for 22 sites, with mean and median values of 1.26 and 1.04, respectively. It should be noted that the values of CF are susceptible to uncertainties in the measurement of tissue optical properties. Nevertheless, we observed small variation in CF within patients but large variation in CF between patients. The largest intra-patients difference in CF is 1.6 times, as in the locations of posterior chest wall and posterior diaphragmatic sulcus of patient #020, while the CF can vary by 4.9 times among patients. Variations in CF among and within patients clearly demonstrates the importance of optical property correction for absolute quantification of in vivo Photofrin concentration.

3.4. Temporal and Spatial Distribution of Photofrin and PDT Dose

FIGS. 7A-H show the temporal changes of local Photofrin concentrations at 22 different sites in the pleural cavities of 8 patients during the course of PDT treatment. Patient #007 and #020 are the first and the most recent patients for whom we obtained PDT dose measurements, respectively, at the time when this paper is being written. Each data point in FIGS. 7A-H represents Photofrin concentration obtained from one fluorescence spectrum using the method described above. Data smoothing was performed by taking the average of all the data points every 10 min of treatment time. The smoothed results show no significant photobleaching of Photofrin, in all measurement sites, during the time course of PDT treatment. The maximum (standard) uncertainty of the smoothed Photofrin concentrations for all patients is ±17.2% (9.5%). The uncertainty arises mainly from (1) low signal-to-noise ratio of measured fluorescence spectra due to the short acquisition time used (300 ms), and (2) the variation in treatment light fluence rate due to the movement of the light source during PDT treatment. We increased the acquisition time of the fluorescence measurements up to 2.5 s in patient #020 to improve the signal-to-noise ratio of the measured fluorescence spectra and the maximum (standard) uncertainty of the smoothed Photofrin concentrations was reduced to ±11.5% (7%).

Figure 8A:
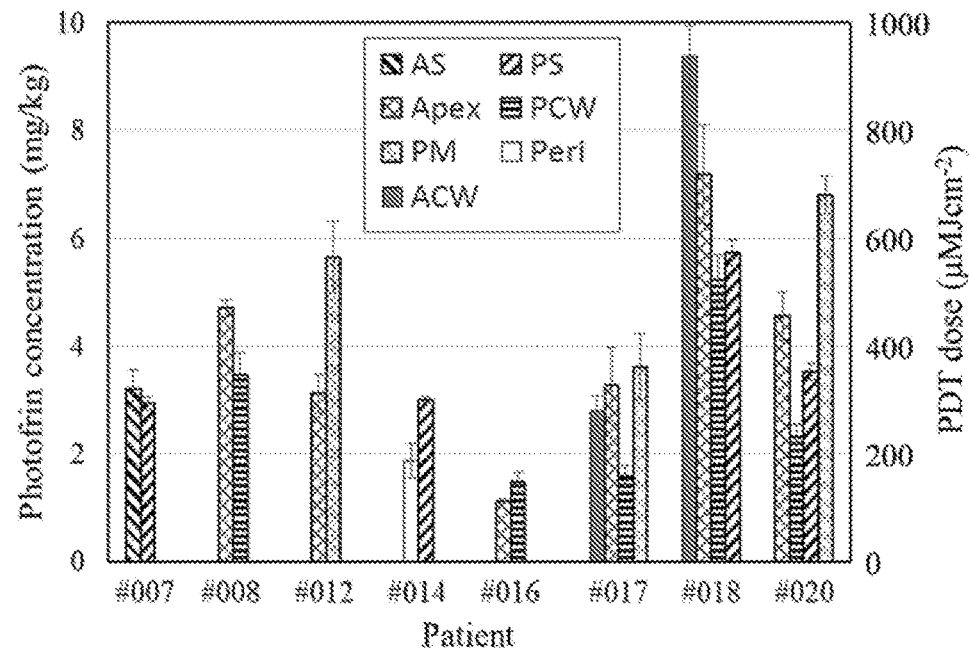
FIG. 8A shows mean Photofrin concentrations and PDT dose delivered to 22 different sites in the pleural cavities of 8 patients.

The mean Photofrin concentrations measured from all 22 sites are presented in FIG. 8A. The error bars represent the uncertainties of the smoothed Photofrin concentrations assuming no photobleaching of Photofrin during the time course of the PDT treatment. As expected, we see large spatial heterogeneities of Photofrin due to the difference in pharmacokinetics within and among patients. With the same administered Photofrin dose of 2 mg kg$^{-1}$, the local sensitizer concentrations can be different by 2.9 times within the same patient (#020) and 8.3 times between patients (#016 and #018). The range of the measured local Photofrin concentration is 1.13 to 9.38 mg kg$^{-1}$; the lowest was measured from the apex location in the pleural cavity of patient #016 while the highest was recorded from the anterior chest wall location in patient #018. The mean and median of the local Photofrin concentrations measured from all sites are 3.94±2.01 mg kg 1 and 3.37±2.01 mg kg$^{-1}$, respectively. To convert the unit of Photofrin concentration from mg kg$^{-1}$ to UM, one can use the molecular weight of Photofrin (605.691 g mol$^{-1}$)6 and assume the average density of human body of 1 kg l$^{-1}$. Thus 1 mg kg$^{-1}$=1×10$^{-3}$ g/605.691 g mol$^{-1}$ 1 l$^{-1}$=1.65×10$^{-6}$ mol 1 l$^{-1}$=1.65 μM.

Figure 8B:
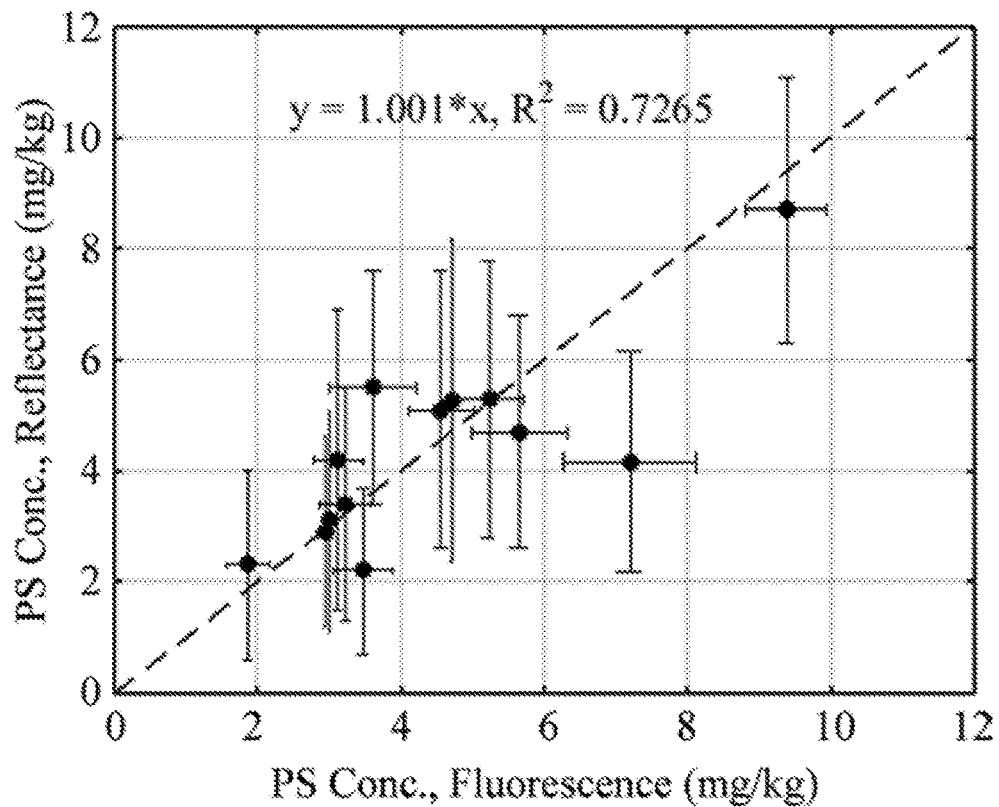
FIG. 8B shows a comparison of Photofrin concentration determined by reflectance and fluorescence measurements.

FIG. 8B shows the comparison of Photofrin concentrations obtained from fluorescence measurements and broadband reflectance measurements. Assuming no photobleaching of Photofrin during PDT treatment as suggested by our fluorescence measurements, reflectance measurements from 9 out of the total 22 sites, which show large discrepancy (~2.5 times difference) in Photofrin concentration before and after PDT treatments, are excluded from the comparison. Linear fit of y=1.001×(shown as dashed line) with a goodness of fit of R$^2$=0.7265 shows reasonable agreement between the data, validating the in vivo fluorescence measurements method using PDT dose dosimetry system.

PDT doses delivered to each measurement site are calculated by taking the product of the local Photofrin concentration and delivered light dose. As each treatment site received the same light dose of 60 J cm$^{-2}$, the delivered PDT dose can be shown on the same plot in FIG. 8A with a secondary axis on the right. Since the total light fluence is the same in all sites, the marked variations in effective PDT doses observed were caused solely by intra- and inter-subject heterogeneities in PS uptake. Large intra- and inter-patient variations in the measured Photofrin concentrations of various tumors and normal tissues have been reported in earlier studies (Busch et al 2004, Hahn et al 2006). The mean and median PDT dose of all sites in this study are 390.1±198.9 MJ cm$^{-2}$ and 333.6±198.9 μMJ cm$^{-2}$, respectively. Tissue optical properties, total light fluence, the mean and standard deviation of smoothed Photofrin concentration and the PDT dose delivered at tissue surface of each pleural site for all patients are summarized in table 2. Light fluence rate and PDT doses delivered at 3 mm below tissue surface, calculated using the analytical equation reported earlier (Ong and Zhu 2016) based on the measured tissue optical properties and mean Photofrin concentrations, are included for comparison.

The current dosimetry system is equipped with four PDT dose channels that measure both light fluence rate and PS fluorescence using the same isotropic detectors. As the isotropic detectors are sutured onto the patients' tissues during PDT treatment, they allow for continuous monitoring of light fluence and PS concentration from the same locations throughout the PDT treatment. This is advantageous compared to broadband reflectance spectroscopy in which reflectance spectra can only be taken before and after PDT treatment using our current contact probe. Our fluorescence measurements show that Photofrin concentrations are mostly unchanged during PDT treatment, but high discrepancies in Photofrin concentrations before and after PDT treatment can be observed using reflectance spectroscopy. These variations in Photofrin concentration can arise due to spatial heterogeneity of tissue and the difference in the exact locations of the two measurements. Continuous measurements of reflectance spectra during PDT treatment are not feasible in the current clinical setting. Therefore, the PDT dose dosimetry system provides a better means to monitor temporal changes in PS concentration during treatment.

Improvements to the PDT dose dosimetry system will further reduce the uncertainty in the measured Photofrin concentration. This uncertainty currently limits our confidence in measuring photobleaching, as any photobleaching in the order of uncertainty cannot be resolved. The normalization method that we employed in data analysis, in which the Photofrin SVD amplitude is divided by the laser SVD amplitude, is insufficient to completely eliminate the effect of varying excitation light fluence rate from measurements. Replacing the current long-pass filters with ones that permit a fraction of the treatment light to be collected by fluorescence spectrometer could provide a direct means to normalize the measured fluorescence to the fluctuating intensity at the excitation wavelength. In addition, we are also working on improving the detection limit of the current system by replacing the spectrometers with more sensitive ones. Work is in progress to expand the system to 16 channels capable of measuring both light fluence rate and fluorescence simultaneously and to develop real-time data analysis capability, which will incorporate input of tissue optical properties from diffuse reflectance measurement, to calculate delivered PDT dose in real time. PDT dose has been proven to be a better predictor of outcome than PDT light dose or administered PS dose alone in our preclinical studies (Qiu et al 2016). It takes into account both the patient-to-patient and site-to-site variations in PS concentration and the variation in optical properties of different tissues, and could potentially serve as a useful predictor of pleural PDT treatment outcome. In the future, PDT dose dosimetry can be used to guide and stop treatment when the desired PDT dose, rather than desired light dose, has been reached.

correction function. The minimum detectable Photofrin concentration of the instrument was determined to be 0.5 mg $kg^{-1}$. Our results showed that the local concentration of Photofrin in tissues did not change significantly during the treatment time. However, large variations in the mean Photofrin concentration are observed within and among patients. With the same administered Photofrin dose and light dose, PDT doses can be different by 2.9 times in intra-patient comparisons and 8.3 times in interpatient comparisons. PDT dose delivered during PDT treatment could serve as a useful predictor of treatment outcome as it takes into account both the patient-to-patient and site-to-site variations in PS concentration and the variation in optical properties of different tissues. Also, this suggests that care must be taken by the physician to create a homogenous PDT dose at all areas of the disease in order to achieve the desired treatment goal.

Figure 9:
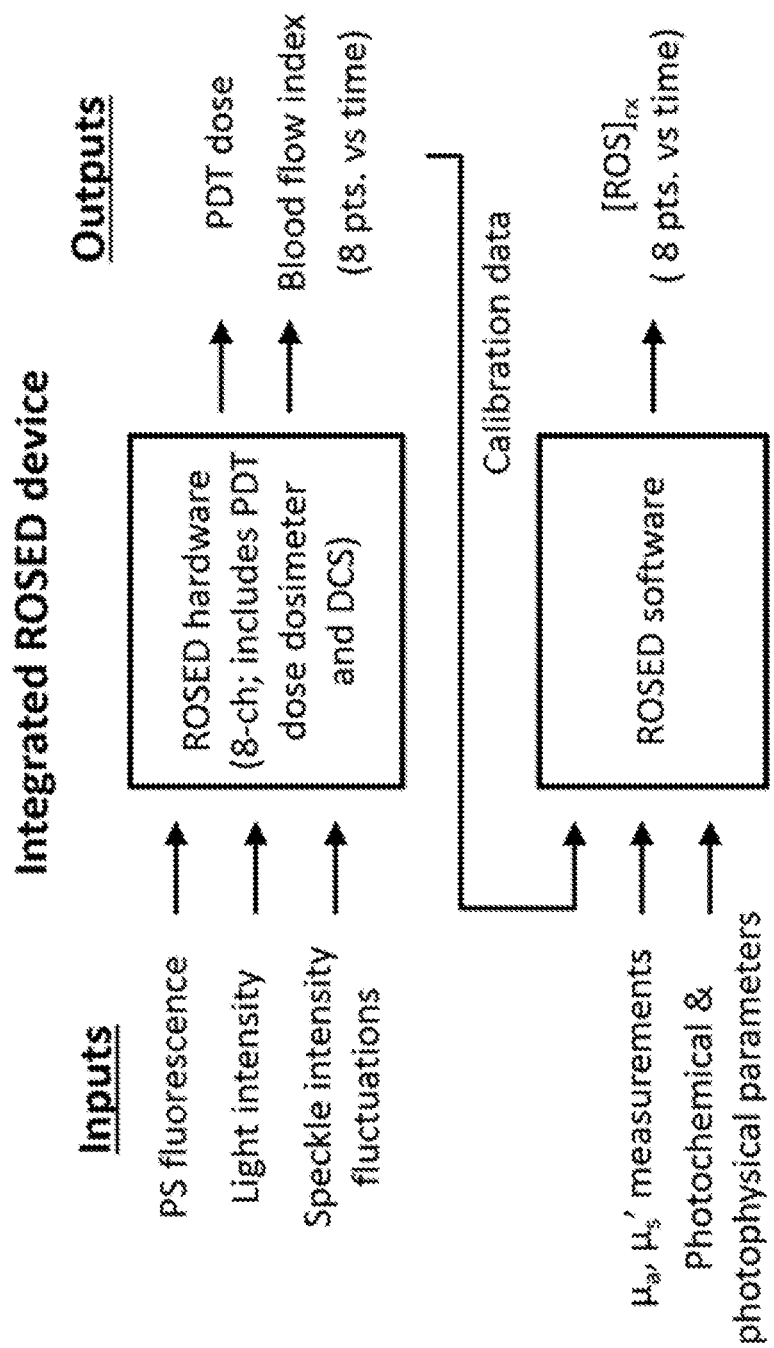
FIG. 9 shows a schematic diagram of an 8-channel integrated ROSED device.
Figure 10:
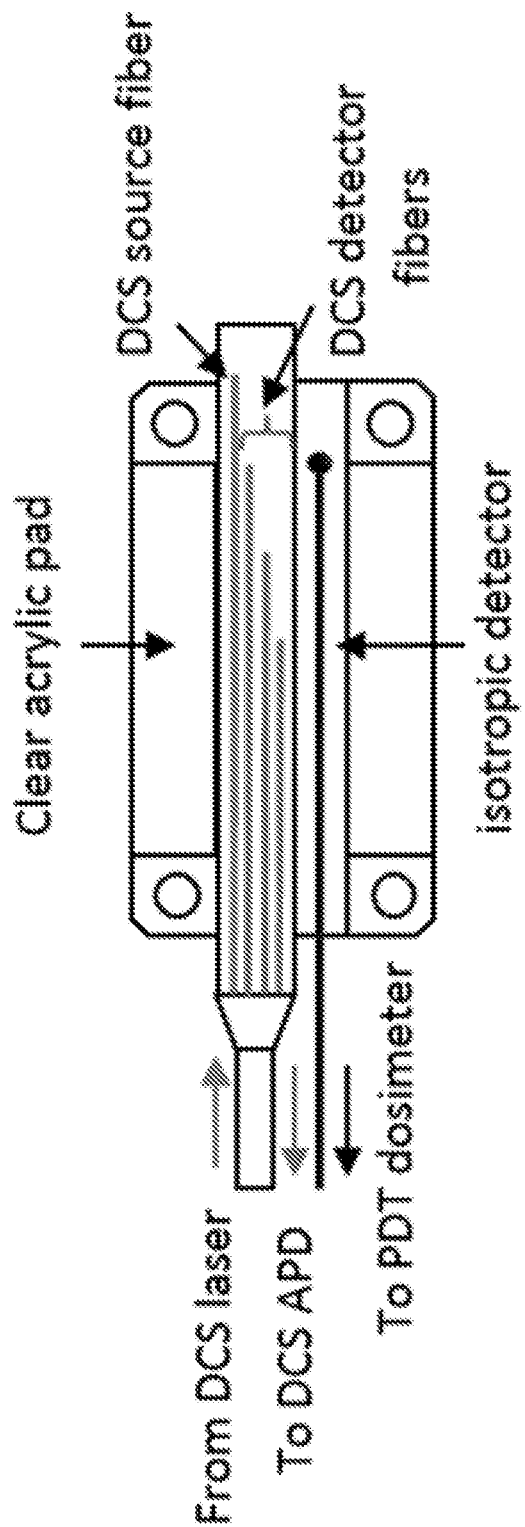
FIG. 10 shows a schematic diagram of an integrated ROSED detector probe that integrated a DCS probe for blood flow and an isotropic detector for PDT dose.

FIGS. 9-10 disclose a flow chart and a diagram of another example device for implementing photodynamic therapy. The device may comprise a plurality of channels, such as 8 channels. The device may comprise an 8-channel reactive-oxygen species (ROS) explicit dosimetry system for photodynamic therapy. This example may comprise one or more of the following features: (1) the device will be capable of simultaneous light fluence and fluorescence spectroscopy measurements (e.g., in 8 channels); (2) The footprint of the entire box will be reduced by optimizing the packing inside; (3) A diffuse correlation system (DCS) system will be expanded to include, for example, 4 long coherence lasers

TABLE 2

Tissue optical properties, correction factors, mean Photofrin concentration, light fluence at 3 mm below surface, PDT dose at surface and 3 mm below surface for 8 patients. The light fluence on surface is the same 60 J $cm^{-2}$ for all patients.

| Patient | Site | Optical Properties | | | | Mean Photofrin concentration (mg $kg^{-1}$) | Light fluence at 3 mm (J $cm^{-2}$) | PDT dose at surface (μMJ $cm^{-2}$) | PDT dose at 3 mm (μMJ $cm^{-2}$) |
|---|---|---|---|---|---|---|---|---|---|
| | | $\mu_a$ ($cm^{-1}$) | $\mu_s'$ ($cm^{-1}$) | $CF_p$ | $CF_a{}^a$ | | | | |
| #007 | AS  | 0.24 | 11.6 | 0.89 | 0.87 | 3.22 ± 0.35 | 73.7  | 318.8 ± 34.7 | 391.8 ± 42.6 |
|      | PS  | 0.37 | 16.6 | 0.89 | 0.68 | 2.94 ± 0.12 | 48.1  | 291.1 ± 11.9 | 233.5 ± 9.5  |
| #008 | Apex| 0.32 | 7.7  | 1.39 | 1.47 | 4.71 ± 0.15 | 77.4  | 466.3 ± 14.9 | 601.7 ± 19.2 |
|      | PCW | 0.16 | 9.1  | 0.84 | 0.93 | 3.47 ± 0.42 | 94.0  | 343.5 ± 41.6 | 538.2 ± 65.1 |
| #012 | Apex| 0.12 | 14.7 | 0.61 | 0.51 | 3.12 ± 0.35 | 87.4  | 308.9 ± 34.7 | 449.8 ± 50.5 |
|      | PM  | 0.24 | 13.1 | 0.83 | 0.76 | 5.65 ± 0.67 | 69.7  | 559.4 ± 66.3 | 650.1 ± 77.1 |
| #014 | Peri| 0.09 | 12.5 | 0.59 | 0.56 | 1.87 ± 0.31 | 100.7 | 185.1 ± 30.7 | 310.6 ± 51.5 |
|      | PS  | 0.15 | 13.4 | 0.68 | 0.61 | 3.01 ± 0.05 | 83.7  | 298.0 ± 5.0  | 415.7 ± 6.9  |
| #016 | Apex| 0.08 | 7.1  | 0.71 | 0.83 | 1.13 ± 0.02 | 119.1 | 111.9 ± 2.0  | 221.9 ± 3.9  |
|      | PCW | 0.09 | 11.9 | 0.60 | 0.59 | 1.47 ± 0.20 | 102.1 | 145.5 ± 19.8 | 247.8 ± 33.7 |
|      | ACW | 0.33 | 12.4 | 1.00 | 0.95 | 2.80 ± 0.27 | 61.2  | 277.2 ± 26.7 | 282.9 ± 27.3 |
| #017 | Apex| 0.42 | 9    | 1.46 | 1.52 | 3.27 ± 0.71 | 63.5  | 323.7 ± 70.3 | 342.7 ± 74.4 |
|      | PCW | 0.26 | 8.8  | 1.11 | 1.18 | 1.58 ± 0.21 | 80.1  | 156.4 ± 20.8 | 208.7 ± 27.7 |
|      | PM  | 0.24 | 10.9 | 0.92 | 0.93 | 3.62 ± 0.61 | 75.8  | 358.4 ± 60.4 | 452.6 ± 76.3 |
|      | ACW | 0.72 | 5.9  | 3.13 | 3.13 | 9.38 ± 0.57 | 57.4  | 928.6 ± 56.4 | 887.7 ± 53.9 |
| #018 | Apex| 0.44 | 5.8  | 2.18 | 2.21 | 7.19 ± 0.92 | 74.9  | 711.8 ± 91.1 | 888.6 ± 113.7|
|      | PCW | 0.7  | 7.4  | 2.48 | 2.61 | 5.23 ± 0.47 | 52.1  | 517.8 ± 46.5 | 449.7 ± 40.4 |
|      | PS  | 0.44 | 5.9  | 2.15 | 2.18 | 5.73 ± 0.24 | 74.4  | 567.3 ± 23.8 | 703.8 ± 29.5 |
| #020 | Apex| 0.27 | 9    | 1.12 | 1.18 | 4.56 ± 0.45 | 78.1  | 451.4 ± 44.6 | 587.9 ± 58.0 |
|      | PCW | 0.32 | 10.9 | 1.08 | 1.07 | 2.32 ± 0.23 | 66.4  | 229.7 ± 22.8 | 254.3 ± 25.2 |
|      | PS  | 0.57 | 9    | 1.79 | 1.88 | 3.54 ± 0.16 | 53.3  | 350.6 ± 15.8 | 311.1 ± 14.1 |
|      | PM  | 0.33 | 8.5  | 1.31 | 1.38 | 6.81 ± 0.35 | 73.4  | 674.2 ± 34.7 | 824.3 ± 42.4a|

$^a CP_a = ((P_1 + P_2 \mu_s') \mu_s') \exp((S_1 + S_2 \mu_s')/\mu_{eff})$ (Sharikova et al 2013, Kim et al 2016a, 2017b, Penjweini et al 2016, Qiu et al 2016); where $P_1 = 3.881$; $P_2 = 0.0103$; $S_1 = 0.5043$; $S_2 = -0.01622$.

4. Conclusion

A 4-channel PDT dose dosimeter was developed and used during Photofrin-mediated pleural PDT. Light dosimetry and PS fluorescence were acquired simultaneously using the same isotropic detectors sutured on pleural cavity wall during PDT treatment. The Photofrin concentration could be determined from fluorescence data using optical properties and 6 4-channel photon counting detectors to allow for 8 simultaneous DCS measurements in the patient (e.g., pleural cavity). Each laser will be shared by two DCS probes using bifurcated fibers; (4) 8 integrated ROSED probes of isotropic detector and DCS detectors and sources.

To estimate blood flow, DCS quantifies the fast speckle intensity fluctuation of multiply scattered coherent NIR light induced by red blood cell motion. Specifically, the normalized intensity temporal autocorrelation function, $g_2(t)=<I(t) I(t+t)>/<I(t)>^2>$, is computed at multiple delay-times, t, where I(t) is the detected light intensity at time t, and the angular brackets ($<\ >$) represent time-averages. A DCS blood flow index, BFI, is ascertained from the decay of $g_2(t)$. BFI is proportional to the blood volume flow rate and numerically equal to $\alpha D_b$, where a is the fraction of photon scattering events that occur from red blood cells in the tissue and $D_b$ is the diffusion coefficient of the red blood cells (Durduran et al 2010). The DCS blood flow index is directly proportional to tissue blood flow, and has been successfully validated against a plethora of gold-standard techniques.

Data indicative of the blood flow may be determined according to the techniques of Durduran, T., R. Choe, W. B. Baker, and A. G. Yodh, Diffuse optics for tissue monitoring and tomography. Reports on Progress in Physics, 2010. 73: p. 076701, which is hereby incorporated by reference in its entirety. The data indicative of the blood flow may be determined according to the techniques of Mesquita, R., T. Durduran, G. Yu, E. Buckley, M. Kim, C. Zhou, R. Choe, U. Sunar, and A. G. Yodh, Direct measurement of tissue blood flow and metabolism with diffuse optics. Philos T Roy Soc A, 2011. 369(1955): p. 4390-4406, which is hereby incorporated by reference in its entirety.

The data indicative of the blood flow (e.g., blood flow index) may be used to determine in-vivo tissue oxygen concentration ($[^3O_2]$). The in-vivo tissue oxygen concentration in combination with light fluence ($\phi$) and photosensitizer concentration ($[S_0]$) obtained previously can be used to determine the reactive oxygen species concentrations ($[ROS]_{rx}$) (Kim M M et al, 2017a):

$$[ROS]_{rx} = \int_0^t \left( \xi \frac{[^3O_2]}{[^3O_2]+\beta} \phi[S_0] + \eta \frac{1}{[^3O_2]+\beta} \phi[S_0] \right) \cdot dt,$$

where $\xi$, $\beta$, and $\eta$ are photochemical parameters specific to a photosensitizer (Kim M M et al 2017a). Blood flow index (BFI) obtained from DCS correlates well with in-vivo tissue oxygen concentration ($[^3O_2]$ for $[ROS]_{rx}$ determination (Penjiweini et al 2017). PDT dose ($\phi[S_0]$) and $[ROS]$rx predicts the outcome of photodynamic therapy better than light fluence alone for all photosensitizers studied (Photofrin, HPPH, BPD) (Penjiweini et al 2017, Penjiweini et al 2016, Kim et al 2017b, Kim et al 2016b, Qiu et al 2016, Qiu et al 2017).

Figure 11:
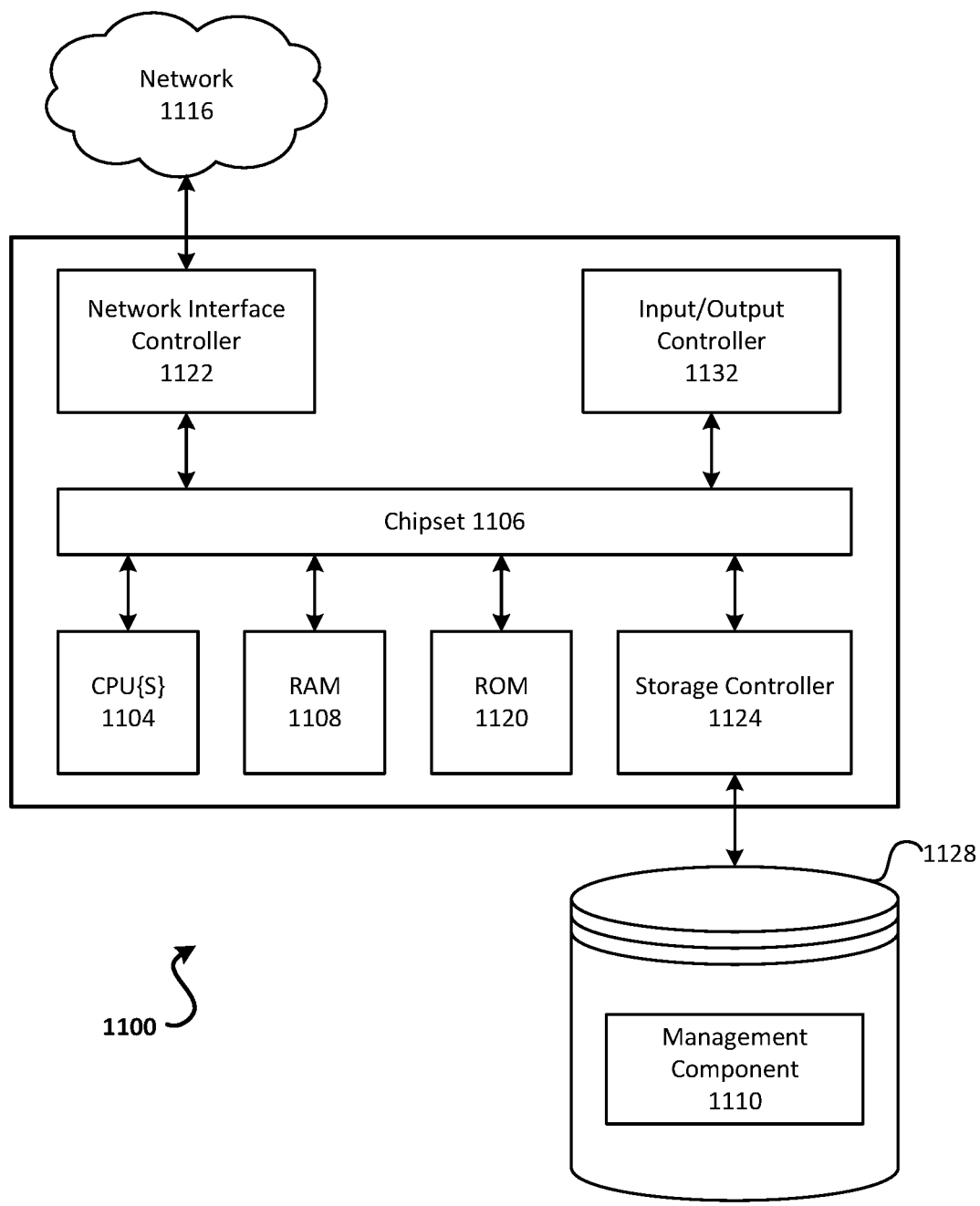
FIG. 11 is a block diagram illustrating an example computing device for implementing one or more aspects of the disclosure.

FIG. 11 depicts a computing device that may be used in various aspects, such as the servers, modules, and/or devices depicted elsewhere herein. The computer architecture shown in FIG. 11 shows a conventional server computer, workstation, desktop computer, laptop, tablet, network appliance, PDA, e-reader, digital cellular phone, or other computing node, and may be utilized to execute any aspects of the computers described herein, such as to implement the methods described further herein.

The computing device 1100 may include a baseboard, or "motherboard," which is a printed circuit board to which a multitude of components or devices may be connected by way of a system bus or other electrical communication paths. One or more central processing units (CPUs) 1104 may operate in conjunction with a chipset 1106. The CPU(s) 804 may be standard programmable processors that perform arithmetic and logical operations necessary for the operation of the computing device 1100.

The CPU(s) 1104 may perform the necessary operations by transitioning from one discrete physical state to the next through the manipulation of switching elements that differentiate between and change these states. Switching elements may generally include electronic circuits that maintain one of two binary states, such as flip-flops, and electronic circuits that provide an output state based on the logical combination of the states of one or more other switching elements, such as logic gates. These basic switching elements may be combined to create more complex logic circuits including registers, adders-subtractors, arithmetic logic units, floating-point units, and the like.

The CPU(s) 1104 may be augmented with or replaced by other processing units, such as GPU(s) 1105. The GPU(s) 1105 may comprise processing units specialized for but not necessarily limited to highly parallel computations, such as graphics and other visualization-related processing.

A chipset 1106 may provide an interface between the CPU(s) 1104 and the remainder of the components and devices on the baseboard. The chipset 1106 may provide an interface to a random access memory (RAM) 1108 used as the main memory in the computing device 1100. The chipset 1106 may further provide an interface to a computer-readable storage medium, such as a read-only memory (ROM) 1120 or non-volatile RAM (NVRAM) (not shown), for storing basic routines that may help to start up the computing device 1100 and to transfer information between the various components and devices. ROM 1120 or NVRAM may also store other software components necessary for the operation of the computing device 1100 in accordance with the aspects described herein.

The computing device 1100 may operate in a networked environment using logical connections to remote computing nodes and computer systems through local area network (LAN) 1116. The chipset 1106 may include functionality for providing network connectivity through a network interface controller (NIC) 1122, such as a gigabit Ethernet adapter. A NIC 1122 may be capable of connecting the computing device 1100 to other computing nodes over a network 1116. It should be appreciated that multiple NICs 1122 may be present in the computing device 1100, connecting the computing device to other types of networks and remote computer systems.

The computing device 1100 may be connected to a mass storage device 1128 that provides non-volatile storage for the computer. The mass storage device 1128 may store system programs, application programs, other program modules, and data, which have been described in greater detail herein. The mass storage device 1128 may be connected to the computing device 1100 through a storage controller 1124 connected to the chipset 1106. The mass storage device 1128 may consist of one or more physical storage units. A storage controller 1124 may interface with the physical storage units through a serial attached SCSI (SAS) interface, a serial advanced technology attachment (SATA) interface, a fiber channel (FC) interface, or other type of interface for physically connecting and transferring data between computers and physical storage units.

The computing device 1100 may store data on a mass storage device 1128 by transforming the physical state of the physical storage units to reflect the information being stored. The specific transformation of a physical state may depend on various factors and on different implementations of this description. Examples of such factors may include, but are not limited to, the technology used to implement the physical storage units and whether the mass storage device 1128 is characterized as primary or secondary storage and the like.

For example, the computing device 1100 may store information to the mass storage device 1128 by issuing instructions through a storage controller 1124 to alter the magnetic characteristics of a particular location within a magnetic disk drive unit, the reflective or refractive characteristics of a particular location in an optical storage unit, or the electrical characteristics of a particular capacitor, transistor, or other discrete component in a solid-state storage unit. Other transformations of physical media are possible without departing from the scope and spirit of the present description, with the foregoing examples provided only to facilitate this description. The computing device 1100 may further read information from the mass storage device 1128 by detecting the physical states or characteristics of one or more particular locations within the physical storage units.

In addition to the mass storage device 1128 described above, the computing device 1100 may have access to other computer-readable storage media to store and retrieve information, such as program modules, data structures, or other data. It should be appreciated by those skilled in the art that computer-readable storage media may be any available media that provides for the storage of non-transitory data and that may be accessed by the computing device 800.

By way of example and not limitation, computer-readable storage media may include volatile and non-volatile, transitory computer-readable storage media and non-transitory computer-readable storage media, and removable and non-removable media implemented in any method or technology. Computer-readable storage media includes, but is not limited to, RAM, ROM, erasable programmable ROM ("EPROM"), electrically erasable programmable ROM ("EEPROM"), flash memory or other solid-state memory technology, compact disc ROM ("CD-ROM"), digital versatile disk ("DVD"), high definition DVD ("HD-DVD"), BLU-RAY, or other optical storage, magnetic cassettes, magnetic tape, magnetic disk storage, other magnetic storage devices, or any other medium that may be used to store the desired information in a non-transitory fashion.

A mass storage device, such as the mass storage device 1128 depicted in FIG. 11, may store an operating system utilized to control the operation of the computing device 1100. The operating system may comprise a version of the LINUX operating system. The operating system may comprise a version of the WINDOWS SERVER operating system from the MICROSOFT Corporation. According to further aspects, the operating system may comprise a version of the UNIX operating system. Various mobile phone operating systems, such as IOS and ANDROID, may also be utilized. It should be appreciated that other operating systems may also be utilized. The mass storage device 1128 may store other system or application programs and data utilized by the computing device 1100.

The mass storage device 1128 or other computer-readable storage media may also be encoded with computer-executable instructions, which, when loaded into the computing device 1100, transforms the computing device from a general-purpose computing system into a special-purpose computer capable of implementing the aspects described herein. These computer-executable instructions transform the computing device 1100 by specifying how the CPU(s) 1104 transition between states, as described above. The computing device 1100 may have access to computer-readable storage media storing computer-executable instructions, which, when executed by the computing device 1100, may perform the methods described herein.

A computing device, such as the computing device 1100 depicted in FIG. 11, may also include an input/output controller 1132 for receiving and processing input from a number of input devices, such as a keyboard, a mouse, a touchpad, a touch screen, an electronic stylus, or other type of input device. Similarly, an input/output controller 1132 may provide output to a display, such as a computer monitor, a flat-panel display, a digital projector, a printer, a plotter, or other type of output device. It will be appreciated that the computing device 1100 may not include all of the components shown in FIG. 11, may include other components that are not explicitly shown in FIG. 11, or may utilize an architecture completely different than that shown in FIG. 11.

As described herein, a computing device may be a physical computing device, such as the computing device 1100 of FIG. 11. A computing node may also include a virtual machine host process and one or more virtual machine instances. Computer-executable instructions may be executed by the physical hardware of a computing device indirectly through interpretation and/or execution of instructions stored and executed in the context of a virtual machine.

Figure 12:
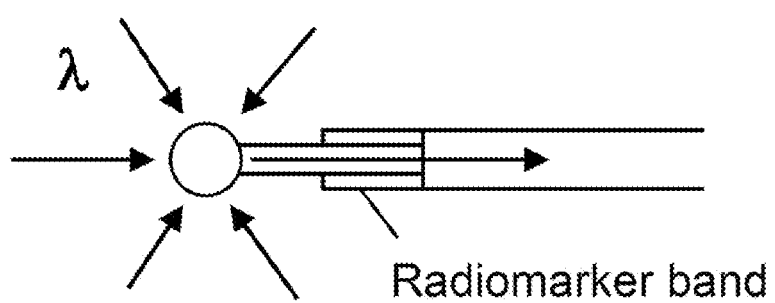
FIG. 12 is a diagram showing an example sensor of an optical detector.

FIG. 12 is a diagram showing an example sensor of an isotropic detector. The sensor may be disposed an at end of an optical fiber (e.g., first optical fiber). The sensor may comprise a Medlight isotropic model probe. The isotropic probe may comprise a fiber-based catheter intended to be used for measuring light intensity in a diffusing medium such as biological tissue. The small spherical tip of the probe may collect the light in a 6 solid angle with an identical efficiency. The probed light may be guided by the fiber to the proximal end of the catheter and can be coupled to a photodetector through an SMA905 connector. The isotropic probe can be manufactured with a gold radiomarker band and consequently the measurement position can be located in the tissue.

Figure 13A:
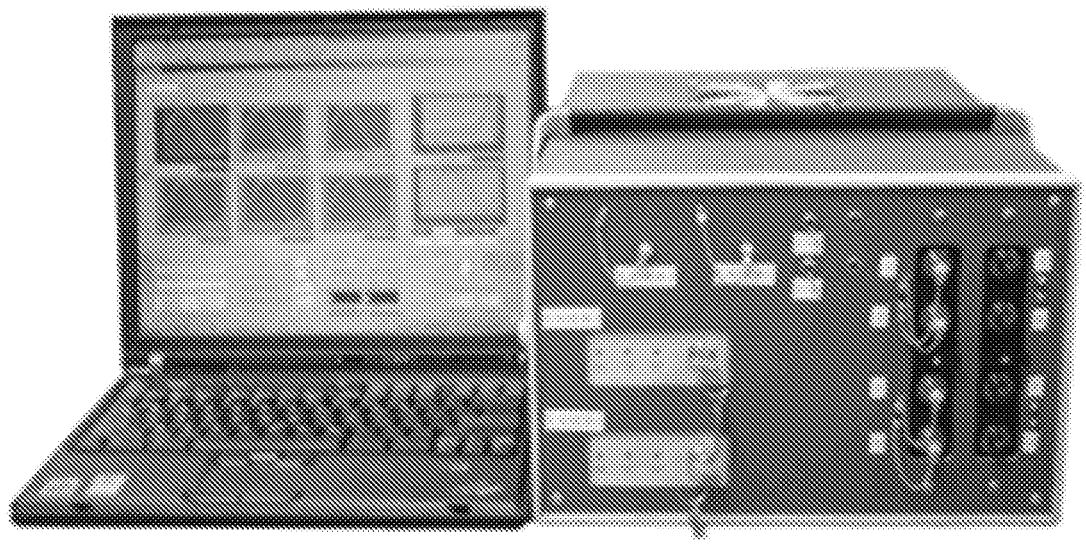
FIG. 13A shows a multi-channel DCS system for blood flow measurement.
Figure 13B:
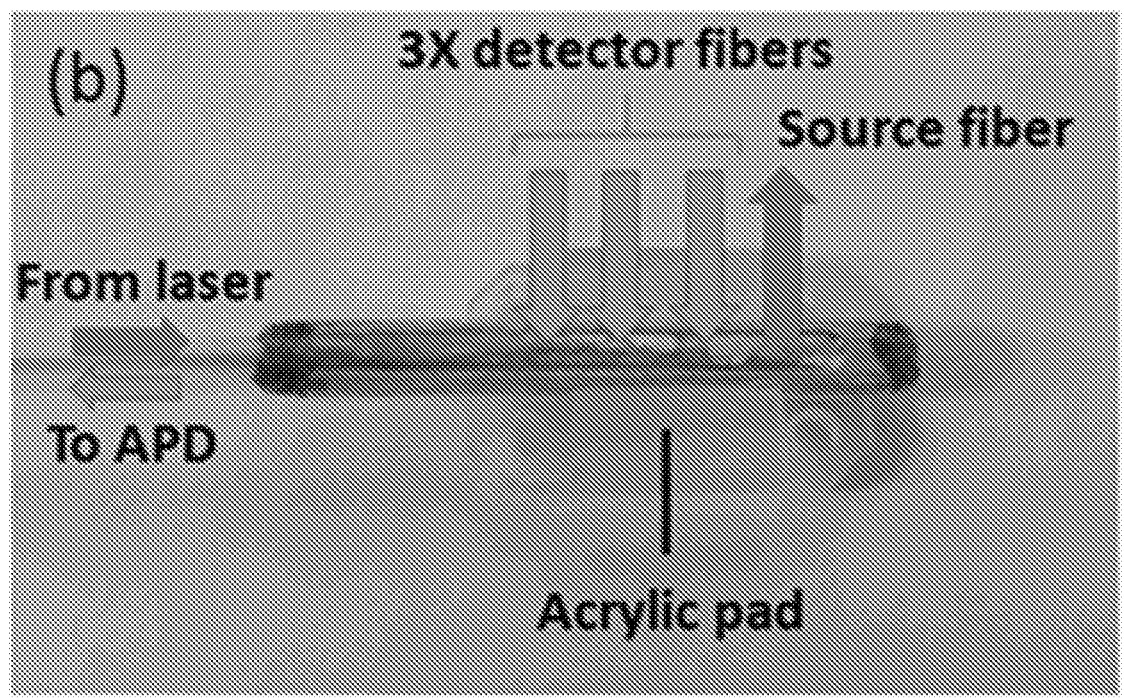
FIG. 13B shows a contact probe with three detector fibers at 0.4, 0.7 and 1 cm lateral from source fiber, mounted on an acrylic pad for patient blood flow during pleural PDT.
Figure 13C:
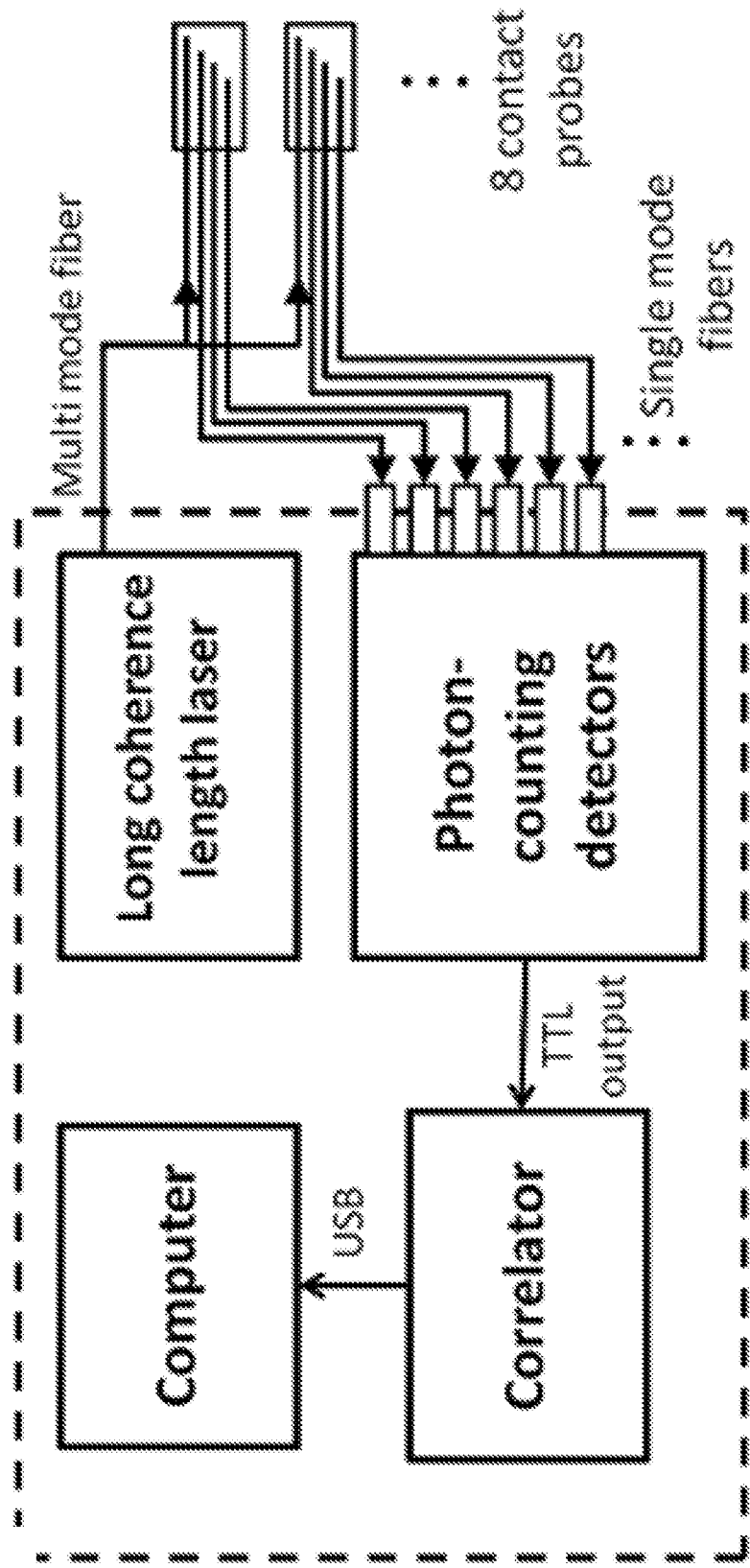
FIG. 13C shows a schematic of a DCS instrument for blood flow measurement.

FIG. 13A shows a multi-channel DCS system for blood flow measurement. An example probe (e.g., blood flow probe) can comprise one or more optical fibers (e.g., detector fibers). The one or more optical fibers can have different lengths. FIG. 13B shows a contact probe with three detector fibers at 0.4, 0.7 and 1 cm lateral from source fiber, mounted on an acrylic pad for patient blood flow during pleural PDT. FIG. 13C shows a schematic of a DCS instrument for blood flow measurement. An example instrument can comprise 2 probes, or any number of probes, such as 8 probes (e.g., 8 probes for blood flow measurements at 8 pleural locations).

Figure 14A:
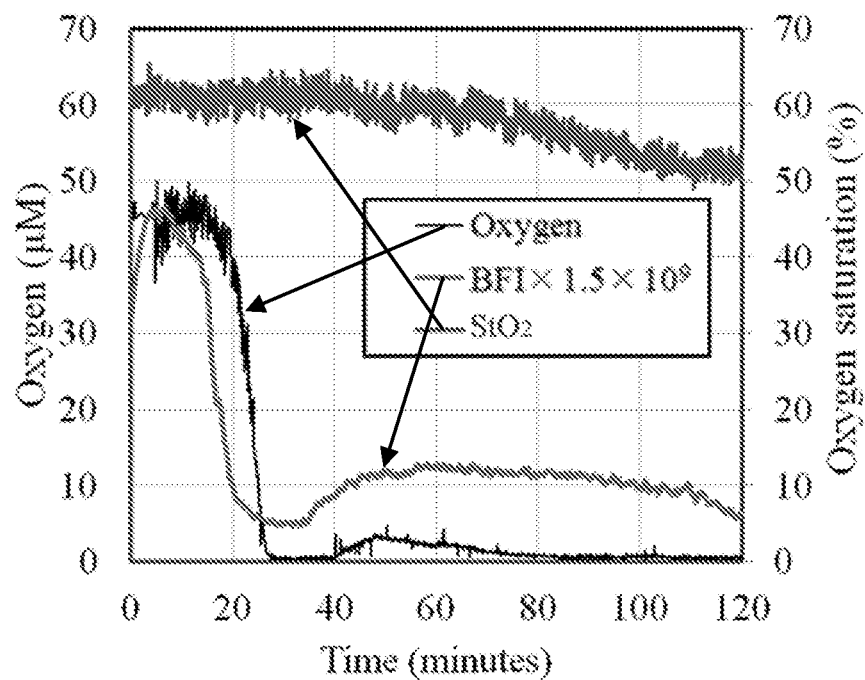
FIG. 14A shows a correlation of the temporal variations of tissue oxygenation level and rescaled blood flow during Photofrin-PDT.
Figure 14B:
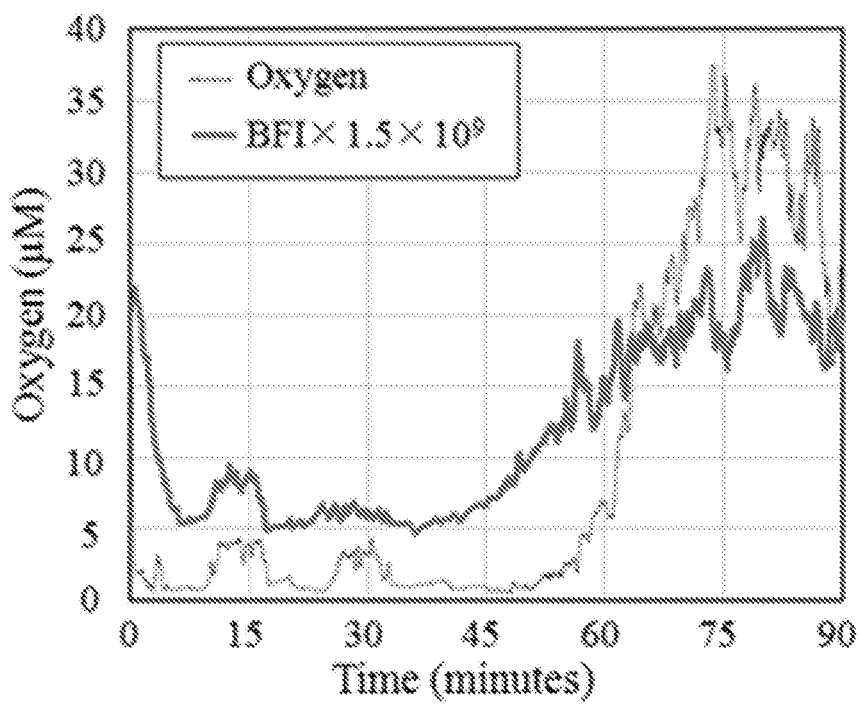
FIG. 14B shows a correlation of the temporal variations of tissue oxygenation level and rescaled blood flow during Photofrin-PDT.
Figure 14C:
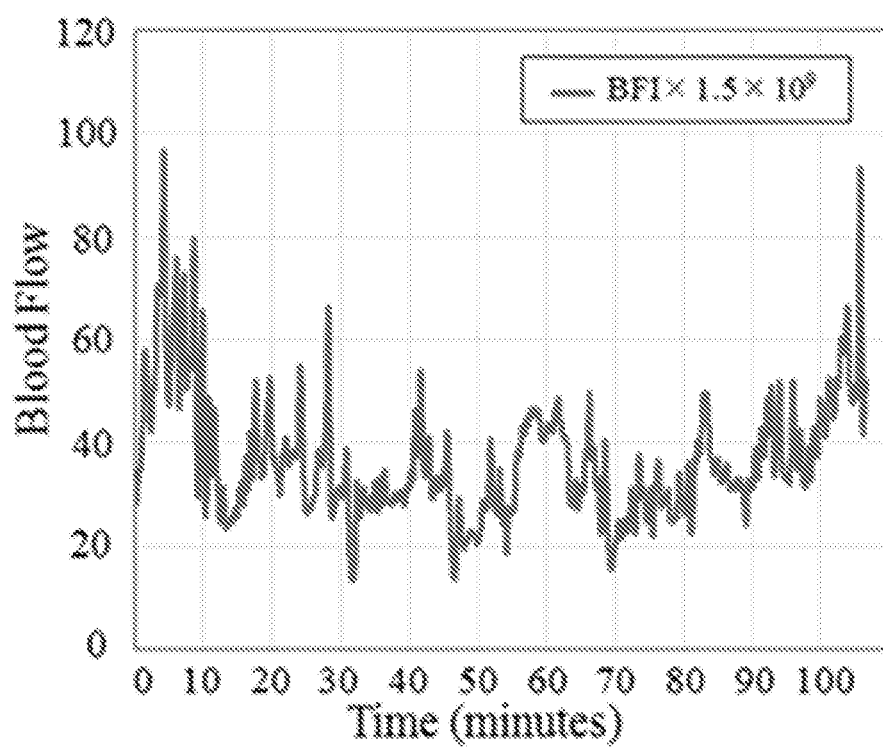
FIG. 14C shows Blood flow in a patient during Photofrin-mediated pleural PDT.

FIG. 14A-B show correlations of the temporal variations of tissue oxygenation level (black line) and rescaled blood flow (red line) during Photofrin-PDT for two mice. Oxygen saturation (StO2) measured during Photofrin-PDT for mouse is also shown in FIG. 14A. FIG. 14C shows blood flow in a patient during Photofrin-mediated pleural PDT. The scaling factor for blood flow to match tissue oxygen concentration is 1.5×109.

An example system may comprise the multi-channel DCS system (e.g., shown in FIGS. 9-10 and FIGS. 13A-C) integrated (e.g., in a single box or form factor) with system shown in FIG. 1A-B. For example, a single probe may comprise a photodynamic therapy dosage sensor comprising a first optical fiber that is bifurcated into a second optical fiber and a third optical fiber. The single probe may comprise a blood flow sensor comprising a fourth optical fiber configured to emit a light and one or more fifth optical fibers configured to receive a reflection of the emitted light. The first optical fiber, second optical fiber, third optical fiber, fourth optical fiber, one or more fifth optical fibers, or a combination thereof may be integrated into a single wrapper, sheath, insulator, and/or the like. The single probe may have a single output port (e.g., for plugging into a single box/ processing device) comprising all of the optical fibers together or may have multiple output ports for plugging into multiple ports (e.g., on the same box, or multiple boxes). The device may have a channel (e.g., port) for each of at least 8 integrated probes). For example, a device may comprise one or more spectrometers, a multichannel DCS system, a dosimetry system, one or more processors, memory comprising software, a display (e.g., or port for outputting data to another device, such as a display). The device may simultaneously receive (e.g., and/or process) optical signals on multiple channels for multiple probes (e.g., and each probe may comprise multiple optical fibers that may be split, bifurcated and/or the like to different processing units, such as a PDT dosage unit (e.g., spectrometers), des processing unit (e.g., photon counting detectors, laser, correlator), dosimetry unit, and/or the like. Each of the PDT dosage unit, des processing unit, dosimetry unit may comprise one or more processors, or one or more processors may be shared between these units.

REFERENCES FOR MAIN TEXT (ABOVE)

Attix F H 1986 Introduction to Radiological Physics and Radiation Dosimetry (New York: Wiley) pp 38-60.

Busch T M et al 2004 Hypoxia and photofrin uptake in the intraperitoneal carcinomatosis and sarcomatosis of photodynamic therapy patients Clin. Cancer Res. 10 4630-8.

Diamond K R, Patterson M S and Farrell T J 2003 Quantification of fluorophore concentration in tissue-simulating media by fluorescence measurements with a single optical fiber Appl. Opt. 42 2436-42.

Finlay J C, Conover D L, Hull E L and Foster T H 2001 Porphyrin bleaching and PDT-induced spectral changes are irradiance dependent in ALA-sensitized normal rat skin in vivo J. Photochem. Photobiol. 73 54-63.

Finlay J C and Foster T H 2005 Recovery of hemoglobin oxygen saturation and intrinsic fluorescence with a forward-adjoint model Appl. Opt. 44 1917-33.

Finlay J C, Zhu T C, Dimofte A, Friedberg J S and Hahn S M 2006a Diffuse reflectance spectra measured in vivo in human tissues during Photofrin-mediated pleural photodynamic therapy Proc. SPIE 6139 61390.

Finlay J C, Zhu T C, Dimofte A, Stripp D, Malkowicz S B, Busch T M and Hahn S M 2006b Interstitial fluorescence spectroscopy in the human prostate during motexafin lutetium-mediated photodynamic therapy J. Photochem. Photobiol. 82 1270-8.

Friedberg J S et al 2017 Extended pleurectomy-decortication-based treatment for advanced stage epithelial mesothelioma yielding a median survival of nearly three years Ann. Thoracic Surg. 103 912-9.

Gardner C M, Jacques S L and Welch A J 1996 Fluorescence spectroscopy of tissue: recovery of intrinsic fluorescence from measured fluorescence Appl. Opt. 35 1780-92.

Gross S A and Wolfsen H C 2010 The role of photodynamic therapy in the esophagus Gastrointest. Endosc. Clin. North Am. 20 35-53.

Hahn S M, Putt M E, Metz J, Shin D B, Rickter E, Menon C, Smith D, Glatstein E, Fraker D L and Busch T M 2006 Photofrin uptake in the tumor and normal tissue of patients receiving intraperitoneal photodynamic therapy Clin. Cancer Res. 12 5464-70.

Huang Z 2005 A review of progress in clinical photodynamic therapy Technol. Cancer Res. Treat. 4 283-93.

Jarvi M T, Patterson M S and Wilson B C 2012 Insights into photodynamic therapy dosimetry: simultaneous singlet oxygen luminescence and photosensitizer photobleaching measurements Biophys. J. 102 661-71.

Kim M M, Ashwini A G, Alexander G and Zhu T C 2017a On the in vivo photochemical rate parameters for PDT reactive oxygen species modeling Phys. Med. Biol. 62 R1-48.

Kim M M, Darafsheh A, Ahmad M, Finlay J C and Zhu T C 2016a PDT dose dosimeter for pleural photodynamic therapy Proc. SPIE 9694 96940.

Kim M M, Penjweini R and Zhu T C 2017b Evaluation of singlet oxygen explicit dosimetry for predicting treatment outcomes of benzoporphyrin derivative monoacid ring A-mediated photodynamic therapy J. Biomed. Opt. 22 028002.

Kim M M, Penjweini R, Liang X and Zhu T C 2016b Explicit macroscopic singlet oxygen modeling for benzoporphyrin derivative monoacid ring a (BPD)-mediated photodynamic therapy J. Photochem. Photobiol. B 164 314-22.

Lambson K, Liang X, Sharikova A V, Zhu T C and Finlay J C 2013 A theoretical and experimental examination of fluorescence in enclosed cavities Proc. SPIE 8568 85680.

Middelburg T A, Hoy C L, Neumann H A M, Amelink A and Robinson D J 2015 Correction for tissue optical properties enables quantitative skin fluorescence measurements using multi-diameter single fiber reflectance spectroscopy J. Dermatol. Sci. 79 64-73.

Muller M G, Georgakoudi I, Zhang Q, Wu J and Feld M S 2001 Intrinsic fluorescence spectroscopy in turbid media: disentangling effects of absorption and scattering Appl. Opt. 40 4633-46.

Ong Y H, Kim M M, Finlay J C, Dimofte A, Cengel K A and Zhu T C 2017 Four-channel PDT dose dosimetry for pleural photodynamic therapy Proc. SPIE 10047 1004717

Ong Y H and Zhu T C 2016 Analytic function for predicting light fluence rate of circular fields on a semi-infinite turbid medium Opt. Exp. 24 26261-81.

Penjweini R, Kim M M, Liu B and Zhu T C 2016 Evaluation of the 2-(1-Hexyloxyethyl)-2-devinyl pyropheophorbide (HPPH) mediated photodynamic therapy by macroscopic singlet oxygen modeling J. Biophoton. 9 1344-54.

Prahl S A, Keijzer M, Jacques S L and Welch A J 1989 A Monte Carlo model of light propagation in tissue Proc. SPIE IS5 102-11.

Qiu H et al 2017 A comparison of dose metrics to predict local tumor control for photofrin-mediated photodynamic therapy J. Photochem. Photobiol. 93 1115-22.

Qiu H, Kim M M, Penjweini R and Zhu T C 2016 Macroscopic singlet oxygen modeling for dosimetry of Photofrin-mediated photodynamic therapy: an in vivo study J. Biomed. Opt. 21 88002.

Sandell J L and Zhu T C 2011 A review of in vivo optical properties of human tissues and its impact on PDT J. Biophoton. 4 773-87.

Sharikova A V, Finlay J C, Liang X and Zhu T C 2013 PDT dose dosimetry for pleural photodynamic therapy Proc. SPIE 8568 856817.

Simone C B and Cengel K A 2014 Photodynamic therapy for lung cancer and malignant pleural mesothelioma Semin. Oncol. 41 820-30.

Solonenko M, Cheung R, Busch T M, Kachur A, Griffin G M, Vulcan T, Zhu T C, Wang H W, Hahn S M and Yodh A G 2002 In vivo reflectance measurement of optical properties, blood oxygenation and motexafin lutetium uptake in canine large bowels, kidneys and prostates Phys. Med. Biol. 47 857-73.

Triesscheijn M, Baas P, Schellens J H M and Stewart F A 2006 Photodynamic therapy in oncology Oncologist 11 1034-44.

Wang H W et al 2005 Broadband reflectance measurements of light penetration, blood oxygenation, hemoglobin concentration, and drug concentration in human intraperitoneal tissues before and after photodynamic therapy J. Biomed. Opt. 10 14004.

Weersink R A, Bogaards A, Gertner M, Davidson S R, Zhang K, Netchev G, Trachtenberg J and Wilson B C 2005 Techniques for delivery and monitoring of TOOKAD (WST09)-mediated photodynamic therapy of the prostate: clinical experience and practicalities J. Photochem. Photobiol. B 79 211-22 Phys. Med. Biol. 63 (2018) 015031 (14pp) 14.

Wilson B C and Patterson M S 2008 The physics, biophysics and technology of photodynamic therapy Phys. Med. Biol. 53 R61-10$^9$.

Zhou X, Pogue B W, Chen B, Demidenko E, Joshi R, Hoopes J and Hasan T 2006 Pretreatment photosensitizer dosimetry reduces variation in tumor response Int. J. Radiat. Oncol. Biol. Phys. 64 1211-20.

Zhu T C, Dimofte A, Hahn S M and Lustig R A 2003 Light dosimetry at tissue surfaces for small circular fields Proc. SPIE 4952 56-67.

Zhu T C and Finlay J C 2006 Prostate PDT dosimetry Photodiag. Photodyn. Ther. 3 234-46.

Zhu T C and Finlay J C 2008 The role of photodynamic therapy (PDT) physics Med. Phys. 35 3127-36.

Durduran, T., R. Choe, W. B. Baker, and A. G. Yodh, 2010, Diffuse optics for tissue monitoring and tomography. Reports on Progress in Physics, 73: p. 076701.

Rozhin Penjweini, Michele M. Kim, Yi Hong Ong, Timothy C. Zhu 2017 Singlet oxygen explicit dosimetry to predict long-term local tumor control for Photofrin-mediated photodynamic therapy. Proc SPIE 10047:100471

ADDITIONAL EXAMPLES AND DATA

Additional examples are described below. Any of the features of any of the examples can be combined with any of the features of the text above or the other examples. References for each example are number separately for each example below.

Example 1—Reactive Oxygen Species Explicit Dosimetry for Photofrin-Mediated Pleural Photodynamic Therapy Explicit dosimetry of treatment light fluence and implicit dosimetry of photosensitizer photobleaching are commonly used methods to guide dose delivery during clinical PDT. Tissue oxygen, however, is not routinely monitored intraoperatively even though it is one of the three major components of treatment. Quantitative information about in vivo tissue oxygenation during PDT is desirable, because it enables reactive oxygen species explicit dosimetry (ROSED) for prediction of treatment outcome based on PDT-induced changes in tumor oxygen level. Here ROSED is demonstrated in a clinical setting, Photofrin-mediated pleural photodynamic therapy, by utilizing tumor blood flow information measured by diffuse correlation spectroscopy (DCS). A DCS contact probe was sutured to the pleural cavity wall after surgical resection of pleural mesothelioma tumor to monitor tissue blood flow (blood flow index) during intraoperative PDT treatment. Isotropic detectors were used to measure treatment light fluence and photosensitizer concentration. Blood-flow-derived tumor oxygen concentration, estimated by applying a preclinically determined conversion factor of $1.5 \times 10^9$ µMs/cm$^2$ to the blood flow index, was used in the ROSED model to calculate the total reacted reactive oxygen species [ROS]rx. Seven patients and 12 different pleural sites were assessed and large inter- and intra-patient heterogeneities in [ROS]rx were observed although an identical light dose of 60 J/cm$^2$ was prescribed to all patients.

Light, photosensitizer, and tissue oxygen are the three most important factors required by photodynamic therapy (PDT) to produce reactive oxygen species (ROS) that kill tumor cells directly, damage tumor vasculature, and stimulate the body's immune response (1-3). In clinical practice, PDT is generally prescribed as a drug dose (mg of photosensitizer per kg of body weight) and treatment light fluence (Jcm$^{-2}$), along with a drug-light interval and light fluence rate (mWcm$^{-2}$). Dosimetry of light fluence is routinely performed to guide PDT delivery, but the delivered light doses are limited in terms of their accuracy in predicting treatment outcome because they do not account for the variation in tissue optical properties, the pharmacokinetics and photobleaching of photosensitizer, and tumor oxygenation during PDT (4-6). Compared to the light fluence and photosensitizer photobleaching ratio, PDT dose defined as the absorbed light dose by the photosensitizer during PDT has been shown to be a better dosimetric quantity for prediction of treatment outcome as long as the oxygen supply is sufficient (4-6). However, this PDT dose metric is less effective when tissue is deprived of oxygen. Since both photochemical consumption of oxygen and microvascular shutdown can lead to tissue hypoxia during PDT, ROS produced via the interactions of all three PDT inputs is the best dose metric for prediction of treatment outcomes; ROS effectively accounts for temporal changes in the light, photosensitizer and tissue oxygen during PDT (5-12). Direct measurement of ROS, however, is very challenging in clinical settings due to the extremely weak signal and the short lifetime of ROS (13-15).

Our work employs an approach based on an empirical macroscopic reactive oxygen species explicit dosimetry (ROSED) model that has been proposed to calculate the total amount of reacted reactive oxygen species ([ROS]rx); the model utilizes the light diffusion equation and the complete set of PDT kinetic equations which quantify dynamic interactions between the light, the photosensitizer concentration, and the tissue oxygenation (16, 17). Recent studies in mice models suggest that measurement of tissue oxygen is important to improve calculation of [ROS]rx, especially for Photofrin-mediated PDT, due to large heterogeneity in PDT-induced physiologic response (4, 8, 9). The ROSED model-calculated tissue oxygen ($^3O_2$) concentrations were found to be in good agreement with measured values for mice treated by BPD- and HPPH-mediated PDT, but the large mouse-to-mouse variations in the temporal changes of [$^3O_2$] for Photofrin-mediated PDT were difficult to model mathematically using ROSED (8, 9). Moreover, although there is a plethora of established techniques for in vivo tissue oxygen measurement, to the best of our knowledge, there are no instruments, approved by the Food and Drug Administration (FDA), which can be used to measure tissue oxygen non-invasively in patients during PDT.

Thus, in this example the potential use of tumor blood flow to perform ROSED when tissue oxygen information is not available during clinical PDT is demonstrated. Blood flow can be measured non-invasively using an optical modality known as diffuse correlation spectroscopy (DCS).

First, we investigated the relationship between tumor blood flow and tumor oxygen during Photofrin-mediated PDT of mice bearing radiation-induced fibrosarcoma (RIF) tumors. Based on the resulting preclinically determined blood flow to oxygen conversion factor, we performed ROSED for Photofrin-mediated photodynamic therapy of patients with malignant pleural mesothelioma. A custom DCS contact probe was used to measure blood flow of the pleural cavity wall intraoperatively. Explicit measurements of light fluence rate and fluorescence measurements of Photofrin concentration were performed using an isotropic detector; monitoring of tumor blood flow was performed concurrently using a DCS probe sutured adjacent to the isotropic detector during PDT delivery. Information about light fluence, Photofrin concentration, and blood-flow-derived oxygen were then used in calculation of [ROS]rx. Different dose metrics, including light fluence, PDT dose and [ROS]rx were also compared and assessed for intra- and inter-patient heterogeneity.

Materials and Methods

Tumor model and PDT treatment conditions: A preclinical study was conducted using a murine model to investigate the relationship between the dynamics of tumor oxygen and blood flow during PDT. Female C3H mice (Charles River Laboratories, Kingston, NY) between 6 to 8 weeks of age were used in this study. Radiation-induced fibrosarcoma (RIF) tumors were propagated on the shoulders of mice by intradermal injection of $3\times10^5$ cells. The mice were fed with chlorophyll-free (alfalfa-free) rodent diet (Harlan Laboratories Inc., Indianapolis, Indiana, US) for two weeks prior to treatment to eliminate the fluorescence signal from chlorophyll-breakdown products, which overlap with the emission spectrum of Photofrin fluorescence. PDT was performed when tumors reached ~4-5 mm in diameter. The treatment area was depilated with Nair (Church & Dwight Co., Inc., Ewing, New Jersey, US) and 5 mg/kg Photofrin was injected via tail vein 24 hours prior to measurements and light delivery. Tissue optical properties and Photofrin fluorescence spectra were obtained using a custom-made multi-fiber contact probe, as described elsewhere (18, 19), before and after PDT. Tissue oxygenation and blood flow changes were monitored continuously during the delivery of PDT using oximeter and DCS as described below. At a 24-h drug-light interval, superficial irradiation of the tumor was performed with a 630-nm laser (Biolitec AG., A-1030, Vienna). A microlens fiber was coupled to the laser to irradiate the tumor uniformly. The details of the PDT treatment conditions are summarized in Table 2. Animals used in this study were under the care of the University of Pennsylvania Laboratory Animal Resources and the studies were approved by the University of Pennsylvania Institutional Animal Care and Use Committee.

Measurement of tumor tissue oxygenation during preclinical PDT: Tumor oxygen was monitored throughout the PDT treatment in mice using an optical oxygen partial pressure ($pO_2$) monitor (OxyLite Pro, Oxford Optronix, Oxford, UK), with a bare-fiber-type probe (NX-BF/O/E, Oxford Optronix, Oxford, UK). The tip of the probe was inserted into the tumor at approximately 1-2 mm depth from the treatment surface to measure the changes in tissue oxygen partial pressure within the tumor mass during PDT. $^3O_2$ concentration was then approximated by multiplying the measured $pO_2$ with $^3O_2$ solubility in tissue, which is 1.295 μM/mmHg (20, 21).

Measurement of blood flow during preclinical PDT: Tumor blood flow was measured using DCS, an optical technique that measures the rapid speckle intensity fluctuations induced by blood flow. DCS, within a noncontact probe setup, was used to monitor blood flow changes in mice during PDT. A detailed description of the DCS instrument can be found in (22, 23). Briefly, a continuous wave 785-nm laser with long coherence length (CrystaLaser Inc., Reno, NV) delivered light through a source fiber, and the diffuse reflected light was collected using two single mode fibers located 0.3 cm laterally from the source fiber. These fibers were mounted on the imaging plane of a camera with sensor removed. A camera lens was used to focus the laser and to collect diffuse reflected light from the tumor at a fixed distance of 15 cm from the camera lens. This setup permits noncontact blood flow measurements during PDT without obstructing the treatment light. Two single photon counting avalanche photodiodes were used to detect the diffuse light in parallel. Notch filters at 630 nm and a 785 nm bandpass filter were used to prevent the ambient room light and the strong 630-nm treatment laser from saturating the detectors. Tissue blood flow measurements started 5 minutes before the beginning of PDT treatment and lasted until completion of PDT.

Clinical PDT treatment and PDT dose detection: The primary goal of this study was to demonstrate and perform explicit dosimetry ROSED in a clinical setting by utilizing knowledge acquired preclinically. Patients with pathologically confirmed epithelioid malignant pleural mesothelioma were enrolled in a phase II randomized clinical trial of extended pleurectomy/decortication with or without Photofrin-mediated PDT. Photofrin (provided by Pinnacle Biologics, Chicago, IL, USA) was administered at 2 mg per kg of body weight as an intravenous infusion approximately 24 hours prior to the anticipated time of intra-operative PDT. After surgically resecting all gross disease, PDT treatment was performed with 630 nm light to a total fluence of 60 $J/cm^2$ as previously described (24-28). Briefly, the pleural cavity was filled with diluted Intralipid solution to aid with light scattering and 60 $J/cm^2$ 630 nm light was delivered to the pleural cavity via an optical fiber inserted into modified endotracheal tube filled with 0.1% Intralipid. Homogeneous light delivery is accomplished by continuously moving the light source around the pleural cavity b with continuous feedback monitoring of light fluence rate and cumulative fluence provided by 8 isotropic detectors (Medlight, Switzerland) sutured to the chest wall. Four of the eight isotropic detectors were used to monitor the light dose and Photofrin fluorescence simultaneously. Long pass filters (Semrock, Inc., Rochester, NY, USA) were used to block the treatment light before the fluorescence was recorded by 4 single channel spectrometers (Exemplar, B&W Tek, Inc., Newark, DE, USA).

Figure 15A:
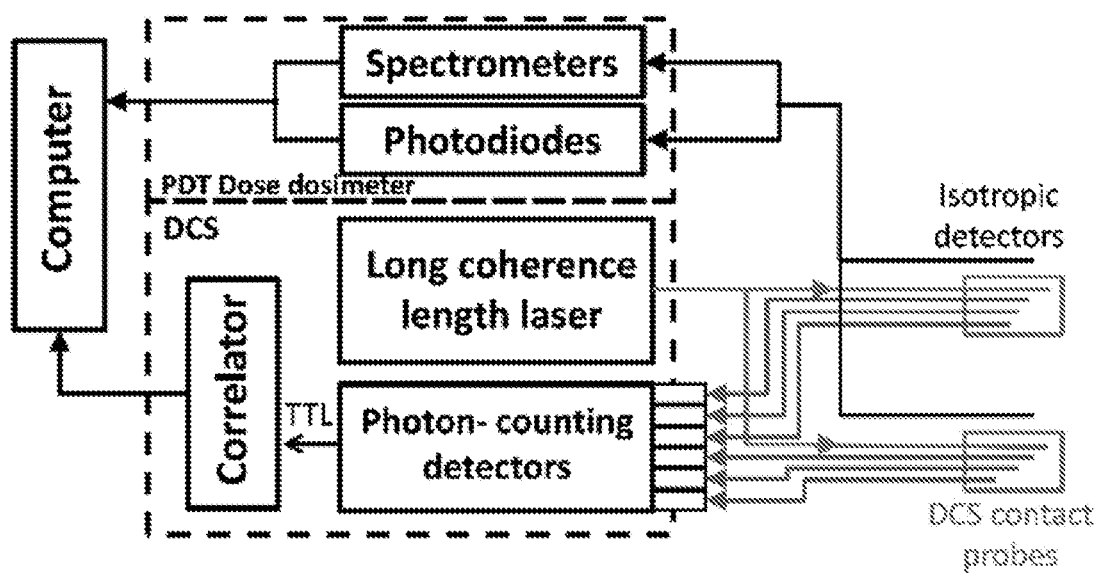
FIG. 15A shows a schematic diagram of the PDT dosimeter and DCS.

A schematic diagram of ROSED dosimeter which consists of a PDT dose dosimeter and a DCS module is shown in FIG. 15A. PDT dose dosimeter consists of photodiodes for light fluence rates measurements and spectrometers for fluorescence measurements. More details about PDT dosimeter and the quantification of absolute Photofrin concentration from measured fluorescence spectra can be found in (19).

Figure 15B:
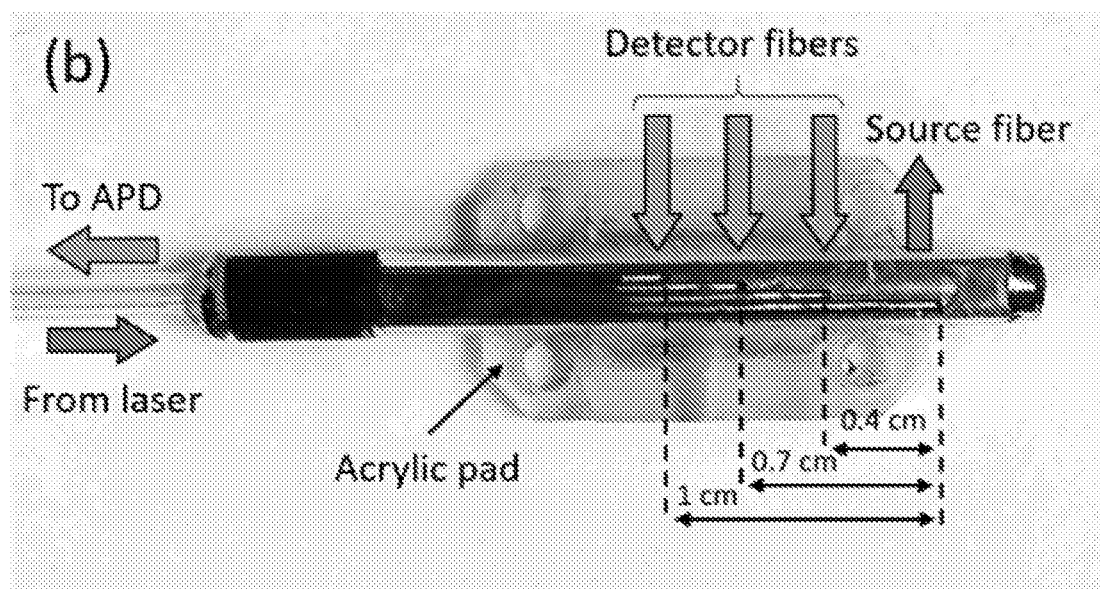
FIG. 15B shows a picture of the DCS contact probe.

FIG. 15A shows a schematic diagram of the PDT dosimeter and DCS. FIG. 15B shows a picture of the DCS contact probe, which comprises of one multimode source fiber and 3 single-mode detector fibers positioned at 0.4 cm, 0.7 cm and 1 cm laterally from the source.

Measurement of blood flow during clinical PDT: DCS monitoring of tissue blood flow during pleural PDT was implemented using a custom built DCS contact probe as shown in FIG. 15B. The contact probe consists of a side-firing multimode source fiber and three single mode detector fibers polished at 45°. Light from a continuous wave 785-nm laser with long coherence length was delivered through the source fiber, and the reflected diffuse light was collected using the detector fibers located at 0.4, 0.7 and 1.0-cm from the source fiber. Three single photon counting avalanche photodiodes were used to detect the diffuse light in parallel. The DCS probe was mounted onto a clear acrylic rectangle pad with small holes at each corner that allowed it to be sutured adjacent to one of the isotropic detectors measuring light fluence rate and photosensitizer fluorescence data. Tissue blood flow was measured continuously throughout the PDT treatment. The study started with one DCS contact probe for the first 2 patients, and it was later expanded for the next 5 patients to include the second DCS contact probe to enable simultaneous measurements of blood flow at two different pleural sites.

Calculation of [ROS]rx using ROSED: The PDT process is described by a set of kinetic equations which can be simplified to compute the production of [ROS]rx (4, 8, 9, 13). These equations are dependent on the temporal and spatial distribution of light fluence rate ($\phi$), photosensitizer concentration ([$S_0$]), ground state oxygen concentration ([$^3O_2$]), oxygen supply rate (g), and the photosensitizer-specific reaction-rate parameters ($\delta$, $\beta$, $\sigma$, and $\xi$). The relevant equations are:

$$\frac{d[S_0]}{dt} = -\frac{[^3O_2]}{[^3O_2]+\beta}([S_0]+\delta)\phi[S_0]\xi\sigma \quad (A1)$$

$$\frac{d[^3O_2]}{dt} = -\frac{[^3O_2]}{[^3O_2]+\beta}\phi[S_0]\xi + g\left(1-\frac{[^3O_2]}{[^3O_2]_0}\right) \quad (A2)$$

$$\frac{d[ROS]_{rx}}{dt} = \xi\frac{[^3O_2]}{[^3O_2]+\beta}\phi[S_0] \quad (A3)$$

Definitions and values of the five specific PDT photo-chemical parameters for Photofrin are given in Table 3. Since Photofrin concentration and tissue oxygen were measured in this study, only Eq. (A3) is needed to calculate for [ROS]rx. For the calculation of [ROS]rx, the term on the right-hand side of Eq. (A3) is integrated over the time course of PDT treatment using the measured value of [$^3O_2$], [$S_0$], and light fluence rate. In vivo light fluence rate distribution can be estimated from the in-air light fluence rate using a 6-parameter analytic expression (29). Tissue optical properties needed for this calculation were obtained from diffuse reflectance measurements using the multi-fiber contact probe. Besides using the value of [$^3O_2$] measured by Oxylite Pro, we also investigated the use of tissue blood flow measured by DCS during PDT to calculate for [ROS]$_{rx}$. The rationale of using tissue blood flow as a surrogate for [$^3O_2$] is because convective supply of oxygen depends directly on blood flow. Changes in tissue oxygenation depend critically on oxygen consumption and supply by blood flow. A conversion factor of $1.5\times10^9$ µMs/cm² was found to be needed to scale the blood flow index to match the measured tissue oxygen. [ROS]$_{rx}$ calculated based on [$^3O_2$] measured by Oxylite was compared with that determined based on DCS blood-flow-derived oxygen.

TABLE 3

Model parameters used in the macroscopic kinetics equations for Photofrin.

| Parameter | Definition | Value | References |
|---|---|---|---|
| $\epsilon$ (cm$^{-1}$ µM$^{-1}$) | Photofrin extinction coefficient | $3.5 \times 10^{-3}$ | (4) |
| $\xi$ (cm² s$^{-1}$ mW$^{-1}$) | Specific oxygen consumption rate | $3.7 \times 10^{-3}$ | (4) |
| $\sigma$ (µM$^{-1}$) | Specific photobleaching ratio | $7.6 \times 10^{-5}$ | (4) |
| $\beta$ (µM) | Oxygen quenching threshold concentration | 11.9 | (4) |
| $\delta$ (µM) | Low-concentration correction | 33 | (4) |

Results

Correlation Between Tumor Oxygen and Blood Flow

Figure 16:
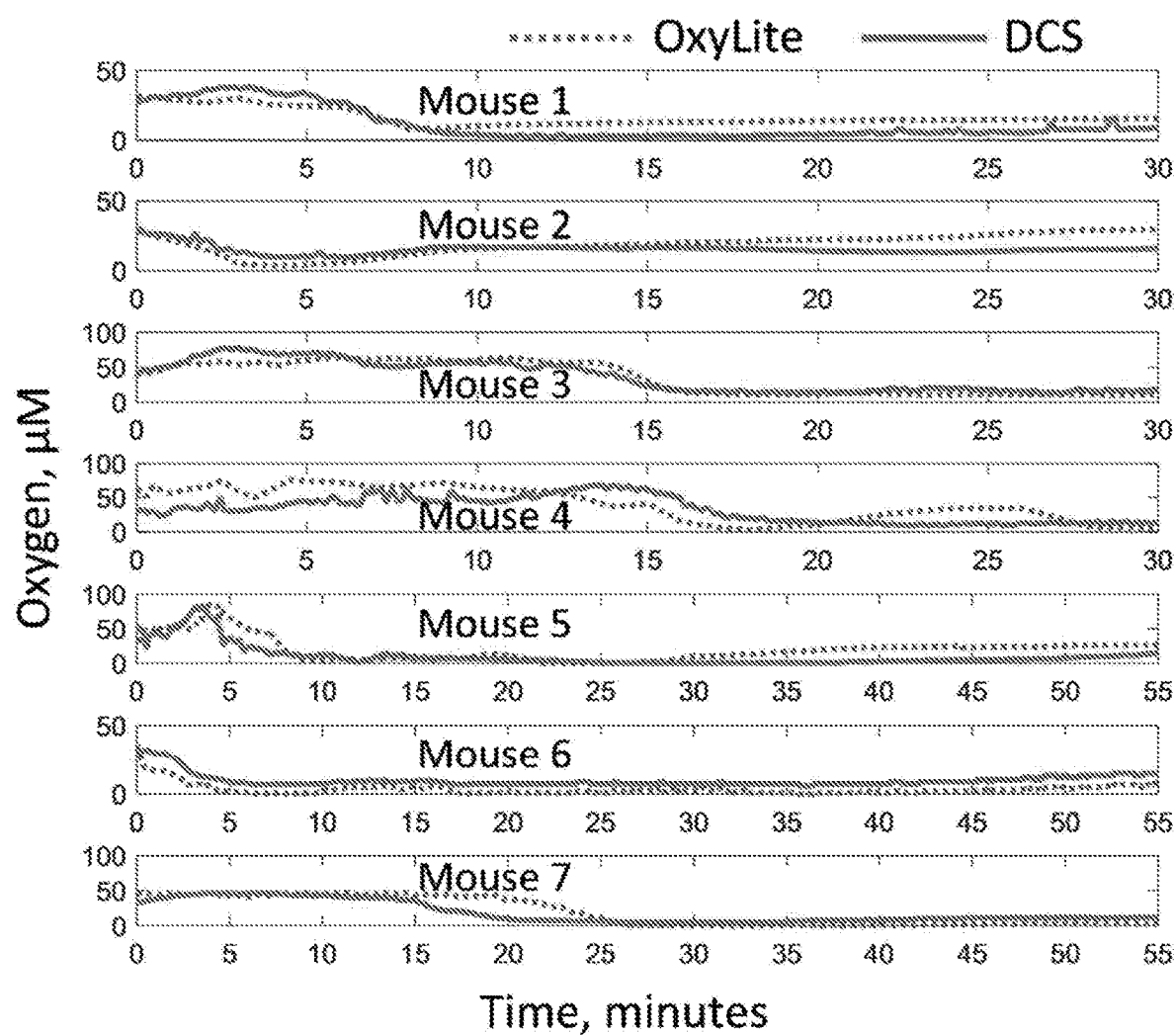
FIG. 16 shows a comparison of tissue oxygen measured using the Oxylite Pro (dotted lines) and blood-flow-derived tissue oxygen estimated as the product of the blood flow index and a conversion factor of $1.5 \times 10^9$ μMs/cm² (solid lines).

FIG. 16 shows a comparison of tissue oxygen measured using the Oxylite Pro (blue dotted lines) and blood-flow-derived tissue oxygen estimated as the product of the blood flow index and a conversion factor of $1.5\times10^9$ µMs/cm² (red solid lines).

FIG. 16 shows the comparison of tissue oxygen measured using two different techniques for seven mice during PDT treatment: blue lines for OxyLite Pro measurements and red lines for DCS measurements. For OxyLite Pro measurements, tumor oxygen (in µM) was approximated from the measured tumor oxygen tension (in mmHg) by multiplying by 1.295 µM/mmHg. For DCS measurements, tumor oxygen was approximated from the blood flow index (cm²/s) using the conversion factor of $1.5\times10^9$ µMs/cm². We have previously demonstrated (8, 30), in murine models, that the magnitude of DCS-measured blood flow index can be scaled by a factor of $1.5\times10^9$ to match the magnitude of the tumor oxygen level at the beginning of light delivery for PDT. Indeed, in the present investigation, we computed the average ratio of the entire spectrum of tumor oxygen to tumor blood flow for all mice investigated and determined a similar blood flow index to tumor oxygen conversion factor of ~$1.5\times10^9$ µMs/cm². Generally, results in FIG. 16 show large variation in temporal changes of tumor oxygenation for mice treated with similar and different PDT treatment conditions. Measurements of tumor oxygen during PDT is therefore very important for accurate ROSED, since the heterogeneities in temporal changes in tumor oxygen cannot be modelled using Eq. A2.

Table 4. In-air light fluence rate (pair), treatment time, initial Photofrin concentration in tumors [PS], and total reacted reactive oxygen species concentration [ROS]rx calculated based on measured [3O2] and DCS blood flow.

TABLE 4

| Index | Mouse # | In-air light fluence rate, $\phi_{air}$ (mW/cm$^2$) | Treatment time (s) | Initial Photofrin concentration, [PS] (μM) | Calculated [ROS]$_{rx}$ (mM) | |
|---|---|---|---|---|---|---|
| | | | | | Measured [$^3$O$_2$] | DCS blood flow |
| 1 | 12-1 | 75 | 1800 | 6.9 | 1.39 | 1.35 |
| 2 | 12-2 | 75 | 1800 | 6.8 | 1.24 | 1.18 |
| 3 | 12-3 | 75 | 1800 | 5.2 | 1.07 | 1.12 |
| 4 | 12-4 | 75 | 1800 | 5.7 | 1.09 | 0.95 |
| 5 | 11-2 | 75 | 3333 | 6.5 | 2.33 | 2.21 |
| 6 | 11-3 | 75 | 3333 | 4.2 | 1.73 | 1.92 |
| 7 | 11-4 | 75 | 3333 | 4.5 | 1.89 | 1.81 |

Although the overall trends in tumor oxygen obtained from Oxylite and DCS measurements are in good agreement, there are subtle differences in the absolute level of oxygen concentration between the two methods. To test if these differences would affect the accuracy of ROSED, we calculated and compared the cumulative [ROS]rx using Eq. A3 based on Oxylite-measured [$^3$O$_2$] and blood-flow-derived [$^3$O$_2$]. A summary of the treatment conditions for the seven mice, including in-air light fluence rate, treatment time, initial Photofrin concentration in tumors [S$_0$], and the calculated total reacted reactive oxygen species concentration [ROS]rx are given in Table 3. It should be noted that Photofrin concentrations were measured at different timepoints during PDT treatment to account for photobleaching, but only initial values of Photofrin concentration are reported here. Despite differences in the absolute level of tumor oxygen, the calculated [ROS]rx based on the two oxygen measurement methods are in close agreement as shown in Table 4. Differences between the calculated [ROS]rx based on Oxylite-measured [$^3$O$_2$] and blood-flow-derived [$^3$O$_2$] data are within 12% for all mice. This suggests that tumor blood flow index, which can be measured noninvasively during clinical PDT, can legitimately be used to derive tumor oxygenation and to calculate for [ROS]rx with desired accuracy.

Temporal and Spatial Distribution of Light Fluence Rate, Oxygen and Photofrin During Pleural PDT FIGS. 17A-H show real-time measurements. FIGS. 17A-B show treatment fluence rate. FIGS. 17C-D show blood-flow-derived oxygen. FIGS. 17E-F show Photofrin concentration measured from two pleural cavity sites. FIGS. 17A, 17C, and 17E are measurements taken from patient #37; FIGS. 17B, 17D, and 17F are measurements taken from patient #38. FIGS. 17G-H are overlay plots of fluence rate and oxygen measurements taken from patient #37.

FIGS. 17A-H shows explicit measurements of light fluence rate, blood-flow-derived oxygen and Photofrin concentration at two different sites in the pleural cavities of two patients (FIGS. 17A, 17C, and 17E are for patient #37, and FIGS. 17B, 17D, 17F are for patient #38) during PDT treatment. FIG. 17A shows temporal changes in light fluence rate detected on the tissue surface of apex (blue line) and posterior mediastinum (red line) in the pleural cavity of patient #37 during the time course of PDT treatment; and FIG. 17B shows the treatment light fluence rate detected on the tissue surface of posterior mediastinum (blue line) and posterior sulcus (red line) for patient #38. Rapid and large fluctuations in the detected light fluence rates were observed for all pleural sites and for all patients (not shown in FIGS. 17A-H). These fluctuations in treatment light fluence rate are due to movement of the treatment light wand in the pleural cavity as the PDT surgeon "paints" the light dose uniformly over the entire pleural cavity. High fluence rates (up to 600 mWcm$^{-2}$) were detected when the PDT treatment wand was in close proximity to an isotropic detector. Very low or no treatment light fluence rate was detected when the PDT treatment wand was moved away from an isotropic detector to a distant pleural site. Light fluence dosimetry at pleural sites, where no DCS measurement was performed, are not reported in this paper.

FIGS. 17C-D show the temporal changes in tumor oxygen measured at the same pleural sites (as in FIGS. 17A-B) for patient #37 and patient #38. Oxygen concentrations were approximated from the blood flow index obtained from DCS measurements, by multiplying the DCS flow index by the conversion factor determined preclinically (as described above).

We can see that tumor oxygen levels were low at the beginning of PDT treatment, suggesting tissue hypoxia due to surgical damage of the tissue vasculature. As PDT starts, tumor oxygen fluctuates significantly, and the fluctuation patterns are distinct from site-to-site and from patient-to-patient during light delivery. Interestingly, fluctuations in tumor oxygen were correlated with variations in light fluence rate. FIGS. 17G-H show overlay plots of fluence rate and tumor oxygen taken from apex and PM locations in patient #37. Comparison between light fluence rate and tumor oxygen shows that high fluence rate induces rapid increase in tumor blood flow and hence increase in tumor oxygen. During periods of low light fluence rate, tissue blood flow (oxygen) decreases and/or returns to the baseline level.

FIGS. 17E-F plots temporal changes in local Photofrin concentration measured at two pleural sites for patient #37 and patient #38. Only Photofrin concentration at sites where DCS measurement was performed, are shown. Each data point in FIGS. 17E-F represents a Photofrin concentration that is obtained from one fluorescence spectrum using the method described elsewhere (19). Photofrin concentrations are corrected for variation in tissue optical properties, obtained using diffuse reflectance spectroscopy, based on an analytical correction function (19). Photofrin fluorescence was excited using the PDT treatment laser. The highly fluctuating treatment light fluence rate, due to the fact that the light source was constantly circulating in the lung cavity, resulted in ±15% uncertainty in the extracted Photofrin concentration. Mean concentration of Photofrin was calculated for all data points every 10 minutes of treatment time, and the results are shown as solid lines in each plot. The mean Photofrin concentrations exhibit no sign of photobleaching for all measurement sites and for all patients (including data not shown) during the time course of PDT treatment. The mean Photofrin concentrations for each pleural site was used for the calculation of [ROS]$_{rx}$ using ROSED and are summarized in Table 4.

Calculated [ROS]rx Using ROSED for Clinical PDT

Table 5. Tissue optical properties, mean Photofrin concentration, light fluence, PDT dose and [ROS]rx at the surface of 12 pleural sites on 7 patients. The light fluence rate on surface is the same at 60 Jcm-2 for all patients.

TABLE 5

| Patient | Site | $\mu_a$ (cm$^{-1}$) | $\mu_s'$ (cm$^{-1}$) | [Photofrin] (mg/kg) | Light fluence at surface (J/cm$^2$) | PDT dose ($\mu$M J/cm$^2$) | [ROS]rx (mM) |
|---|---|---|---|---|---|---|---|
| #20 | PM | 0.42 | 10.3 | 7.2 | 60 | 710.8 | 0.69 |
| #27 | ACW | 0.32 | 8.9 | 5.7 | 60 | 564.3 | 0.34 |
| #29 | PCW | 0.65 | 13.2 | 9.8 | 60 | 965.3 | 1.17 |
|  | ACW | 0.38 | 9.6 | 6.0 | 60 | 594.0 | 0.46 |
| #35 | PM | 0.48 | 9.2 | 5.7 | 60 | 564.3 | 0.85 |
|  | AS | 0.35 | 9.1 | 6.7 | 60 | 663.3 | 0.33 |
| #37 | PM | 0.17 | 5.9 | 4.1 | 60 | 396.0 | 0.75 |
|  | Apex | 0.22 | 6.3 | 3.9 | 60 | 382.1 | 0.59 |
| #38 | PM | 0.23 | 6.8 | 4.4 | 60 | 435.6 | 0.41 |
|  | PS | 0.62 | 12.3 | 10.4 | 60 | 1029.6 | 0.72 |
| #40 | PM | 0.25 | 10.2 | 4.1 | 60 | 403.9 | 0.31 |
|  | AS | 0.35 | 11.2 | 6.7 | 60 | 659.3 | 0.41 |
| Average |  | 0.37 ± 0.15 | 9.4 ± 2.2 | 6.2 ± 2.1 | 60 | 614 ± 202.6 | 0.59 ± 0.25 |

PM: posterior mediastinum; ACW: anterior chest wall; PCW: posterior chest wall; AS: anterior sulcus; PS: posterior sulcus.

1 mg/kg Photofrin=1.65 µM Photofrin.

Cumulative [ROS]$_{rx}$ generated by PDT can be calculated using ROSED by integrating the right-hand side of Eq. A3 over the time course of PDT treatment. Temporal and spatial distribution of light fluence rate on the tissue surface ($\phi$), mean Photofrin concentration ([S$_0$]), blood-flow-derived tumor oxygen ([$^3$O$_2$]) and photophysical parameters ($\xi$ and $\beta$) are needed for the calculation of [ROS]rx. The ROSED-calculated [ROS]rx (mM) for 12 sites in seven patients are summarized in Table 4. Comparison to other commonly used dose metrics, namely light fluence (J/cm$^2$), and the PDT dose (µM J/cm$^2$) defined as the product of light fluence and photosensitizer concentration, are also included in Table 4. Tissue optical properties used for the correction of Photofrin concentration, and the resultant mean corrected Photofrin concentration ([Photofrin]) are also provided. The mean (standard deviation) optical properties ($\mu_a$, $\mu_s'$) of all pleural tissues for seven patients are 0.37±0.15 cm$^{-1}$ and 9.4±2.2 cm$^{-1}$, respectively. The mean Photofrin concentration of all pleural tissues for seven patients is 6.2±2.1 mg/kg. Note, 1 mg/kg of Photofrin is equivalent to 1.65 µM of Photofrin. PDT treatments were delivered based on light dosimetry until the prescribed 60 Jcm$^{-2}$ of light fluence. Therefore, the light fluence detected at the surface for all pleural sites are equal as shown in Table 4.

Despite the same light dose, PDT dose delivered to all sites can be largely different. The mean (standard deviation) PDT dose delivered to these seven patients is 614±202.6 µM J/cm$^2$, with a maximum of 1029.6 µM J/cm$^2$ and minimum of 382.1 µM J/cm$^2$. The variations in delivered PDT dose are mainly due to the intra- and inter-patient heterogeneities in Photofrin uptake. Lastly, assessment of ROSED reveals large variation in the calculated [ROS]rx for all patients, with a mean (standard deviation) of 0.59±0.25 mM and a range of 0.31–1.17 mM. These values are consistent with those reported in previous preclinical Photofrin-mediated PDT studies (4, 8, 9, 31).

DISCUSSION

Treatment light fluence is the most commonly used dose metric for clinical PDT dosimetry due to its simplicity of measurement and correlation to treatment outcome. PDT dose is a better metric than light fluence alone, with improved treatment outcome prediction because it accounts for variations in tumor photosensitizer uptake. Our group has demonstrated the feasibility of clinical PDT dose dosimetry by concurrent measurement of light fluence rate and photosensitizer concentration during PDT. In preclinical investigations, [ROS]rx, or [$^3$O$_2$]rx for type II PDT only, have been demonstrated to be the best dose metric to predict PDT treatment outcome (4-6); however, its clinical implementation is challenging due to a lack of FDA-approved instrument to measure tissue oxygenation reliably during PDT.

For our work, we employ the ROSED model (Eq. A2). In principle, it can be used to estimate [$^3$O$_2$] when PS-specific photophysical parameters are known, and the estimated [$^3$O$_2$] is found to be in close agreement with measured tumor oxygen during preclinical PDT using several photosensitizers, including HPPH and BPD (10, 11). However, for Photofrin-mediated PDT, large mouse-to-mouse heterogeneity in tumor oxygen changes has been observed in preclinical studies (8, 22) and these inter-subject variations [$^3$O$_2$] in cannot be modeled using Eq. (A2). Thus, explicit measurement of tumor oxygen is needed to improve the accuracy of the calculated [ROS]rx to better predict for treatment outcome.

Since the convective oxygen delivery depends directly on blood flow, increasing blood flow will increase the delivery of oxygen via the blood to the tissues. Our previous simulation study (20) showed that maximum oxygen supply rate (g) increases linearly with blood flow velocity ($v_z$). Indeed, in our present investigation, we observed that changes in tumor blood flow during PDT correlates well with the temporal changes in tumor oxygen (see FIG. 16). Tumor blood flow is measured using DCS, which is a noninvasive optical modality that can be employed clinically to collect patient's blood flow data. The average ratio of tumor oxygen to tumor blood flow for all mice was determined to be 1.5×10$^9$, similar to the conversion factor determined from our previous investigation (22). (The conversion factor has a unit of µMs/cm$^2$; hence the blood-flow-derived tumor oxygen (blood flow index multiplied by conversion factor) has the same units as measured tumor oxygen (µM).)

Tissue optical properties used to determine blood flow indices were obtained from diffuse reflectance measured before the beginning of PDT treatment. Tissue optical properties were assumed to be constant during the time course of PDT. Irwin et. al. has investigated the effect of optical properties on the DCS blood flow indices and found that $\mu_s'$ has a greater influence on blood flow than $\mu_a$ (32). However, one should expect larger temporal variation in tissue $\mu_a$ than $\mu_s'$, due to the rapid and large fluctuations in tumor blood flow that would cause the total hemoglobin concentration to change significantly. $\mu_s'$ depends on the size, morphology and structure of the tissue components, and is less likely to highly vary during the time course of a PDT treatment. Based on Irwin's investigation, a 150% change in tissue absorption would result in approximately 40% error in the estimated blood flow index. Therefore, small mismatches between traces of OxyLite-measured tumor oxygen and blood-flow-derived tumor oxygen as shown in FIG. 16 could be due to over- or underestimation of blood flow indices caused by false assumption of constant tissue optical properties in this study. For future PDT studies, concurrent measurements of DCS and optical properties would be useful to account for temporal variations in tissue $\mu_a$ and $\mu_s'$. Nevertheless, despite the potential error in blood-flow-derived tumor oxygen as discussed above, [ROS]rx calculated based on blood flow in this study are in very good agreement with the [ROS]rx calculated using measured [$^3O_2$]. We found that small differences in [$^3O_2$] have minimal impact on the calculation of [ROS]rx.

In conclusion, for the first time, we performed ROSED in a clinical setting with concurrent explicit measurements of light fluence rate and PS concentration using a PDT dose dosimeter, and blood flow using DCS. Tumor oxygenation was estimated by multiplying DCS blood flow index by a preclinically determined conversion factor of $1.5 \times 10^9$ µMs/cm². The mean (standard deviation) of calculated [ROS]rx from a total of 12 pleural sites and seven patients is 0.59±0.25 mM. The results reveal large inter- and intra-patient heterogeneity in [ROS]rx, although PDT treatment was performed to a prescribed light dose of 60 J/cm². ROSED has been demonstrated in preclinical studies to be a useful predictor of treatment outcome, because it accounts for both subject-to-subject and site-to-site variations in PS concentration and tissue oxygenation. This study suggests that real-time ROSED could be explored to guide physicians in creating a homogenous [ROS]rx at all areas of disease, thereby providing for the desired treatment goal.

REFERENCES FOR EXAMPLE 1

1. Dougherty, T. J., C. J. Gomer, B. W. Henderson, G. Jori, D. Kessel, M. Korbelik, J. Moan and Q. Peng (1998) Photodynamic Therapy. *JNCI: Journal of the National Cancer Institute* 90, 889-905.
2. Agostinis, P., K. Berg, K. A. Cengel, T. H. Foster, A. W. Girotti, S. O. Gollnick, S. M. Hahn, M. R. Hamblin, A. Juzeniene, D. Kessel, M. Korbelik, J. Moan, P. Mroz, D. Nowis, J. Piette, B. C. Wilson and J. Golab (2011) Photodynamic therapy of cancer: An update. *CA: A Cancer Journal for Clinicians* 61, 250-281.
3. Allison, R. R. and K. Moghissi (2013) Photodynamic Therapy (PDT): PDT Mechanisms. *Clin Endosc* 46, 24-29.
4. Qiu, H., M. M. Kim, R. Penjweini and T. C. Zhu (2016) Macroscopic singlet oxygen modeling for dosimetry of Photofrin-mediated photodynamic therapy: an in-vivo study. *J Biomed Opt* 21, 88002-88002.
5. Penjweini, R., M. M. Kim, B. Liu and T. C. Zhu (2016) Evaluation of the 2-(1-Hexyloxyethyl)-2-devinyl pyropheophorbide (HPPH) mediated photodynamic therapy by macroscopic singlet oxygen modeling. *Journal of Biophotonics* 9, 1344-1354.
6. Kim, M. M., R. Penjweini and T. C. Zhu (2017) Evaluation of singlet oxygen explicit dosimetry for predicting treatment outcomes of benzoporphyrin derivative monoacid ring A-mediated photodynamic therapy. *J Biomed Opt* 22, 1-10, 10.
7. Yamamoto, J., S. Yamamoto, T. Hirano, S. Li, M. Koide, E. Kohno, M. Okada, C. Inenaga, T. Tokuyama, N. Yokota, S. Terakawa and H. Namba (2006) Monitoring of Singlet Oxygen Is Useful for Predicting the Photodynamic Effects in the Treatment for Experimental Glioma. *Clinical Cancer Research* 12, 7132-7139.
8. Penjweini, R., M. M. Kim, Y. H. Ong and T. C. Zhu (2017) Singlet oxygen explicit dosimetry to predict long-term local tumor control for Photofrin-mediated photodynamic therapy. SPIE.
9. Sheng, T., Y. H. Ong, T. M. Busch and T. C. Zhu (2019) Reactive oxygen species explicit dosimetry to predict local tumor control for Photofrin-mediated photodynamic therapy. SPIE.
10. Penjweini, R., M. M. Kim, Y. H. Ong and T. C. Zhu (2017) Singlet oxygen explicit dosimetry to predict local tumor control for HPPH-mediated photodynamic therapy. SPIE.
11. Kim, M. M., R. Penjweini, Y. H. Ong and T. C. Zhu (2017) Singlet oxygen explicit dosimetry to predict long-term local tumor control for BPD-mediated photodynamic therapy. SPIE.
12. Wei, Y., J. Zhou, D. Xing and Q. Chen (2007) In vivo monitoring of singlet oxygen using delayed chemiluminescence during photodynamic therapy. *J Biomed Opt* 12, 1-7, 7.
13. Ong, Y. H., M. M. Kim and T. C. Zhu (2018) Photodynamic Therapy Explicit Dosimetry. In *Recent Advancements and Applications in Dosimetry*, Vol. 1. pp. 45-72. Nova Science Publishers, Inc.
14. Jarvi, M. T., M. S. Patterson and B. C. Wilson (2012) Insights into photodynamic therapy dosimetry: simultaneous singlet oxygen luminescence and photosensitizer photobleaching measurements. *Biophys J* 102, 661-671.
15. Jarvi, M. T., M. J. Niedre, M. S. Patterson and B. C. Wilson (2006) Singlet oxygen luminescence dosimetry (SOLD) for photodynamic therapy: current status, challenges and future prospects. *Photochemistry and photobiology* 82, 1198-1210.
16. Wang, K. K.-H., J. C. Finlay, T. M. Busch, S. M. Hahn and T. C. Zhu (2010) Explicit dosimetry for photodynamic therapy: macroscopic singlet oxygen modeling. *Journal of Biophotonics* 3, 304-318.
17. Zhu, T. C., J. C. Finlay, X. Zhou and J. Li (2007) Macroscopic modeling of the singlet oxygen production during PDT. SPIE.
18. Finlay, J. C., T. C. Zhu, A. Dimofte, J. S. Friedberg and S. M. Hahn (2006) Diffuse reflectance spectra measured in vivo in human tissues during Photofrin-mediated pleural photodynamic therapy. *Proceedings of SPIE—the International Society for Optical Engineering* 6139.
19. Ong, Y. H., M. M. Kim, J. C. Finlay, A. Dimofte, S. Singhal, E. Glatstein, K. A. Cengel and T. C. Zhu (2017) PDT dose dosimetry for Photofrin-mediated pleural photodynamic therapy (pPDT). *Physics in medicine and biology* 63, 015031.
20. Zhu, T. C., B. Liu and R. Penjweini (2015) Study of tissue oxygen supply rate in a macroscopic photodynamic therapy singlet oxygen model. *J Biomed Opt* 20, 038001-038001.

21. Whiteley, J. P., D. J. Gavaghan and C. E. Hahn (2002) Mathematical modelling of oxygen transport to tissue. *Journal of mathematical biology* 44, 503-522.
22. Ong, Y. H., M. M. Kim, R. Penjweini, C. E. Rodriguez, A. Dimofte, J. C. Finlay, T. M. Busch, A. G. Yodh, K. A. Cengel, S. S. M. D. and T. C. Zhu (2017) *Monitoring and assessment of tumor hemodynamics during pleural PDT*. SPIE.
23. Yu, G., T. Durduran, C. Zhou, H. W. Wang, M. E. Putt, H. M. Saunders, C. M. Sehgal, E. Glatstein, A. G. Yodh and T. M. Busch (2005) Noninvasive monitoring of murine tumor blood flow during and after photodynamic therapy provides early assessment of therapeutic efficacy. *Clinical cancer research: an official journal of the American Association for Cancer Research* 11, 3543-3552.
24. Friedberg, J. S., C. B. Simone, 2nd, M. J. Culligan, A. R. Barsky, A. Doucette, S. McNulty, S. M. Hahn, E. Alley, D. H. Sterman, E. Glatstein and K. A. Cengel (2017) Extended Pleurectomy-Decortication-Based Treatment for Advanced Stage Epithelial Mesothelioma Yielding a Median Survival of Nearly Three Years. *The Annals of thoracic surgery* 103, 912-919.
25. Friedberg, J. S., M. J. Culligan, R. Mick, J. Stevenson, S. M. Hahn, D. Sterman, S. Punekar, E. Glatstein and K. Cengel (2012) Radical pleurectomy and intraoperative photodynamic therapy for malignant pleural mesothelioma. *The Annals of thoracic surgery* 93, 1658-1665; discussion 1665-1657.
26. Friedberg, J. S., R. Mick, M. Culligan, J. Stevenson, A. Fernandes, D. Smith, E. Glatstein, S. M. Hahn and K. Cengel (2011) Photodynamic therapy and the evolution of a lung-sparing surgical treatment for mesothelioma. *The Annals of thoracic surgery* 91, 1738-1745.
27. Du, K. L., S. Both, J. S. Friedberg, R. Rengan, S. M. Hahn and K. A. Cengel (2010) Extrapleural pneumonectomy, photodynamic therapy and intensity modulated radiation therapy for the treatment of malignant pleural mesothelioma. *Cancer biology & therapy* 10, 425-429.
28. Simone, C. B., 2nd and K. A. Cengel (2014) Photodynamic therapy for lung cancer and malignant pleural mesothelioma. *Seminars in oncology* 41, 820-830.
29. Ong, Y. H. and T. C. Zhu (2016) Analytic function for predicting light fluence rate of circular fields on a semi-infinite turbid medium. *Opt. Express* 24, 26261-26281.
30. Ong, Y. H., M. M. Kim, Z. Huang and T. C. Zhu (2018) Reactive oxygen species explicit dosimetry (ROSED) of a type 1 photosensitizer. SPIE.
31. Qiu, H., M. M. Kim, R. Penjweini, J. C. Finlay, T. M. Busch, T. Wang, W. Guo, K. A. Cengel, C. B. Simone I I, E. Glatstein and T. C. Zhu (2017) A Comparison of Dose Metrics to Predict Local Tumor Control for Photofrin-mediated Photodynamic Therapy. *Photochemistry and photobiology* 93, 1115-1122.
32. Irwin, D., L. Dong, Y. Shang, R. Cheng, M. Kudrimoti, S. D. Stevens and G. Yu (2011) Influences of tissue absorption and scattering on diffuse correlation spectroscopy blood flow measurements. *Biomed. Opt. Express* 2, 1969-1985.

Example 2—Reactive Oxygen Species Explicit Dosimetry to Predict Tumor Growth for BPD-Mediated Vascular Photodynamic Therapy Photodynamic therapy (PDT) is a well-established treatment modality for cancer and other malignant diseases; however, quantities such as light fluence, and PDT dose do not fully account for all of the dynamic interactions between the key components involved. In particular, fluence rate ($\varnothing$) effects are not accounted for, which has a large effect on the oxygen consumption rate. In this preclinical study, reacted reactive oxygen species ($[ROS]_{rx}$) was investigated as a dosimetric quantity for PDT outcome. We studied the ability of $[ROS]_{rx}$ to predict the cure index (CI) after PDT of murine tumors; $CI=1-k/k_{ctr}$, where k and $k_{ctr}$ are the growth rate of PDT-treated and control (untreated) tumor, respectively. Mice bearing radiation induced fibrosarcoma (RIF) tumors were treated with BPD-mediated PDT at different in-air fluences (22.5, 40, 45, 50, 70 and 100 J/cm$^2$) and in-air $\varnothing$ (75 and 150 mW/cm$^2$) with a BPD dose of 1 mg/kg and a drug-light interval of 15 mins. Treatment was delivered with a collimated laser beam of 1 cm diameter at 690 nm. Explicit dosimetry of initial tissue oxygen concentration, tissue optical properties, and BPD concentration was used to calculate $[^1O_2]_{rx}$. $\varnothing$ was calculated for the treatment volume based on Monte-Carlo simulations and measured tissue optical properties. CI was used as an endpoint for four dose metrics: light fluence, PDT dose, and $[ROS]_{rx}$. PDT dose was defined as the product of the time-integral of photosensitizer concentration and $\varnothing$ at a 3 mm tumor depth. Preliminary studies show that $[ROS]_{rx}$ best correlates with CI and is an effective dosimetric quantity that can predict treatment outcome. The threshold dose for $[ROS]_{rx}$ is determined to be 0.23 mM and is about 4.3 times smaller than the corresponding value for conventional BPD-mediated PDT using DLI of 3 hrs.

Photodynamic therapy (PDT) is a used for treatment of cancer and other localized diseases. PDT leads to fewer side effects than radiation and chemotherapy, because it does not involve ionizing radiation and can be well-localized[1,2]. Widespread use of PDT has been stilted due to the difficulty in accurately quantifying the dose. PDT is not only "dynamic" but also multifaceted[3,4]. It incorporates light, photosensitizer, and oxygen to create activated singlet oxygen ($^1O_2$) to kill cells. To address the need for better dosimetry in PDT, we have developed a singlet oxygen explicit dosimetry model to predict PDT outcome[5-8]. The four major photochemical parameters in a macroscopic singlet oxygen model have been investigated and determined for the photosensitizer benzoporphyrin derivative monoacid A (BPD).

In this study, reactive oxygen species explicit dosimetry (ROSED) was performed using measured values of light fluence rate, photosensitizer concentration and [ROS] to evaluate the treatment outcomes of BPD-mediated vascular PDT in mice bearing radiation-induced fibrosarcoma (RIF) tumors. Vascular-targeted PDT can be achieved using a short (15 minute) drug light interval[9]. By inducing vascular shutdown, nutrient supply and removal of metabolic waste is halted which results in RIF tumor cell death. This is beneficial because tumor vasculature is easy to access for targeting, and vascular damage is efficient in cancer cell killing and has a low likelihood of leading to drug resistance.

Materials and Methods

Tumor Model

RIF cells were cultured and 30 µl were injected at 1×10$^7$ cells/ml intradermally over the right shoulders of 6 to 8 weeks old female C$_3$H mice (NCI-Frederick, Frederick, Maryland), as described previously[10-12]. Animals were under the care of the University of Pennsylvania Laboratory Animal Resources. All studies were approved by the University of Pennsylvania Institutional Animal Care and Use Committee. Tumors were treated at a size of ~3 to 5 mm in diameter. Fur within the region of tumor inoculation was clipped prior to injection of cells, and the treatment area was depilated with Nair (Church & Dwight Co., Inc., Ewing, New Jersey) at least 24 h before measurements. Mice were provided a chlorophyll-free (alfalfa-free) rodent diet (Harlan Laboratories Inc., Indianapolis, Indiana) starting at least 10 days prior to treatment to eliminate the fluorescence signal from chlorophyll-breakdown products, which have a similar emission range to the BPD fluorescence spectra used to determine the concentration of BPD in the tumor. During the delivery of PDT, mice were kept under anesthesia on a heat pad at 38° C.

PDT Treatment Conditions

PDT was delivered using an optical fiber with a microlens attachment coupled to a diode laser. A 690 nm laser (B&W Tek Inc., Newark, Delaware) was used for PDT after a 15 min drug-light interval. The in-air fluence rate ($\phi_{air}$) is defined as the calculated irradiance determined by the laser power divided by the treatment area (1 cm diameter spot size). The in-air fluence was calculated by multiplying the in-air fluence rate by the treatment time. RIF tumor-bearing mice with no photosensitizer and no light excitation were used as controls (n=5). Treatment conditions are summarized in Table 6.

(B&W Tek Inc., Newark, Delaware). A microlens fiber was coupled to the laser to irradiate the tumor uniformly. Animals were assigned to four light dose groups, and each group was comprised of 2 to 3 subgroups with different $\phi$. There were a total of 6 treatment groups: 22.5 J/cm$^2$ at 75 mW/cm$^2$, 30 J/cm$^2$ at 75 mW/cm$^2$, 45 mW/cm$^2$ at 75 mW/cm$^2$, 50 J/cm$^2$ at 75 mW/cm$^2$, 70 J/cm$^2$ at 150 mW/cm$^2$ and 100 J/cm$^2$ at 150 mW/cm$^2$. Tumor-bearing mice that received neither light irradiation nor BPD were used as controls.

Oxygen Measurements

The in vivo tissue oxygen partial pressure $_pO_2$ was measured during PDT treatment using a phosphorescence-based ROS probe (OxyLite Pro, Oxford Optronix, Oxford, United Kingdom). A bare-fiber-type probe (NX-BF/O/E, Oxford Optronix, Oxford, United Kingdom) was placed inside the tumor at a 3 mm depth from the treatment surface. The ROS concentration ([ROS]) was calculated by multiplying the measured $_pO_2$ with the ROS solubility in tissue, which is 1.295 µM/mmHg.[5] Measured [ROS]$_0$ and [ROS](t) were used to calculate reacted oxygen species using the macroscopic singlet oxygen model.[14,15]

TABLE 6

| Index | Mice # | Fluence rate in air (expected) mW/cm$^2$ | Fluence rate (measured) on surface mW/cm$^2$ | Fluence rate in tissue (3 mm) mW/cm$^2$ | Total treatment time seconds | BPD concentration µM | PDT dose µMJ/cm$^2$ | [ROS] µM | k | CI |
|---|---|---|---|---|---|---|---|---|---|---|
| 1 | #15-4 | 75.00 | 95.70 | 73.62 | 300.00 | 0.23 | 5.10 | 0.07 | 0.41 | 0.01 |
| 2 | #15-5 | 75.00 | 96.90 | 74.54 | 300.00 | 0.22 | 4.97 | 0.06 | 0.41 | 0.01 |
| 3 | #14-3 | 75.00 | 97.20 | 74.77 | 300.00 | 0.20 | 4.43 | 0.03 | 0.42 | 0.00 |
| 4 | #16-4 | 75.00 | 95.00 | 73.08 | 300.00 | 0.13 | 2.77 | 0.04 | 0.41 | 0.01 |
| 5 | #16-5 | 75.00 | 89.00 | 68.46 | 300.00 | 0.22 | 4.58 | 0.14 | 0.40 | 0.03 |
| 6 | #8-1 | 75.00 | 98.00 | 75.38 | 400.00 | 0.19 | 5.70 | 0.20 | 0.34 | 0.18 |
| 7 | #8-2 | 75.00 | 88.00 | 67.69 | 400.00 | 0.29 | 7.85 | 0.32 | 0.00 | 1.00 |
| 8 | #8-3 | 75.00 | 87.00 | 68.15 | 400.00 | 0.25 | 6.82 | 0.22 | 0.20 | 0.51 |
| 9 | #17-5 | 75.00 | 78.00 | 60.00 | 400.00 | 0.17 | 4.08 | 0.17 | 0.38 | 0.07 |
| 10 | #18-1 | 75.00 | 118.00 | 90.77 | 400.00 | 0.24 | 8.71 | 0.29 | 0.03 | 0.93 |
| 11 | #18-2 | 75.00 | 98.00 | 75.38 | 400.00 | 0.15 | 4.52 | 0.11 | 0.42 | 0.00 |
| 12 | #8-4 | 75.00 | 76.00 | 58.46 | 600.00 | 0.25 | 8.70 | 0.22 | 0.19 | 0.54 |
| 13 | #8-5 | 75.00 | 75.00 | 57.69 | 600.00 | 0.31 | 10.69 | 0.41 | 0.00 | 1.00 |
| 14 | #9-1 | 75.00 | 84.00 | 64.62 | 600.00 | 0.19 | 7.37 | 0.20 | 0.29 | 0.30 |
| 15 | #15-1 | 75.00 | 118.00 | 90.77 | 600.00 | 0.20 | 10.91 | 0.28 | 0.06 | 0.85 |
| 16 | #15-2 | 75.00 | 104.00 | 80.00 | 600.00 | 0.14 | 6.54 | 0.20 | 0.31 | 0.25 |
| 17 | #15-3 | 75.00 | 114.00 | 87.69 | 600.00 | 0.23 | 11.91 | 0.47 | 0.00 | 1.00 |
| 18 | #16-1 | 75.00 | 96.00 | 73.85 | 666.00 | 0.16 | 7.66 | 0.21 | 0.17 | 0.59 |
| 19 | #16-2 | 75.00 | 98.00 | 75.38 | 666.00 | 0.19 | 9.50 | 0.25 | 0.14 | 0.67 |
| 20 | #16-3 | 75.00 | 94.00 | 72.31 | 666.00 | 0.19 | 9.28 | 0.37 | 0.00 | 1.00 |
| 21 | #17-1 | 75.00 | 102.00 | 78.46 | 666.00 | 0.18 | 9.42 | 0.28 | 0.08 | 0.81 |
| 22 | #17-2 | 75.00 | 76.00 | 58.46 | 666.00 | 0.19 | 7.37 | 0.21 | 0.25 | 0.39 |
| 23 | #17-3 | 75.00 | 78.00 | 60.00 | 666.00 | 0.14 | 5.40 | 0.17 | 0.33 | 0.21 |
| 24 | #17-4 | 75.00 | 78.00 | 60.00 | 666.00 | 0.21 | 8.30 | 0.23 | 0.18 | 0.56 |
| 25 | #3-2 | 150.00 | 233.00 | 179.23 | 467.00 | 0.14 | 11.30 | 0.35 | 0.00 | 1.00 |
| 26 | #3-3 | 150.00 | 260.00 | 200.00 | 467.00 | 0.11 | 10.38 | 0.32 | 0.00 | 1.00 |
| 27 | #3-4 | 150.00 | 269.00 | 206.92 | 467.00 | 0.15 | 14.78 | 0.53 | 0.00 | 1.00 |
| 28 | #3-5 | 150.00 | 284.00 | 218.46 | 467.00 | 0.12 | 12.53 | 0.51 | 0.00 | 1.00 |
| 29 | #A-3 | 150.00 | 270.00 | 207.69 | 467.00 | 0.12 | 11.29 | 0.41 | 0.00 | 1.00 |
| 30 | #4-1 | 150.00 | 268.00 | 259.00 | 667.00 | 0.17 | 29.86 | 0.75 | 0.00 | 1.00 |
| 31 | #4-2 | 150.0 | 255.00 | 246.40 | 667.00 | 0.14 | 23.32 | 0.51 | 0.00 | 1.00 |
| 32 | #4-3 | 150.0 | 272.00 | 262.80 | 667.00 | 0.18 | 32.18 | 0.74 | 0.00 | 1.00 |
| 33 | #4-4 | 150.0 | 260.00 | 251.00 | 667.00 | 0.12 | 19.51 | 0.62 | 0.00 | 1.00 |
| 34 | #A-4 | 150.0 | 249.00 | 240.60 | 667.00 | 0.13 | 20.53 | 0.64 | 0.00 | 1.00 |

Table 6: In-air light fluence, in-air light fluence rate, BPD concentration in tumors, initial tissue oxygenation, PDT dose, as well as calculated reactive oxygen species concentration.

BPD (trademark Visudyne®) at a dosage of 1 mg/kg was injected through the mouse tail vein as described previously.[12,13] At a 15 min drug-light interval, superficial irradiation of the tumor was performed with a 690-nm laser BPD Concentration Following the drug-light interval of 15 min, measurements of light fluence rate, photosensitizer concentration and [ROS] were performed. BPD fluorescence spectra was obtained using a custom-made multi-fiber contact probe before and after PDT.[17] The probe is connected to a 405 nm laser (Power Technology Inc., Little Rock, AR, USA) for the fluorescence excitation of BPD and a multichannel CCD spectrograph (InSpectrum, Princeton Instruments, Trenton, NJ, USA) for the collection of the spectra. The in vivo photosensitizer concentration was obtained by comparing the in vivo BPD spectra with those of phantoms with known photosensitizer concentrations. The attenuation of the fluorescence signal due to light absorption and scattering by tissues was corrected by applying an empirical correction factor described elsewhere.[16] The accuracy of in vivo measurements was validated by ex vivo measurements in separate mice.[19]

Tumor Regrowth Rate Analysis

Tumor volumes were measured daily after PDT. Width (a) and length (b) were measured with slide calibers, and tumor volumes (V) was calculated using $V=\pi \times a^2 \times b/6$.[20] Tumor volumes were tracked for 14 days, and the tumor regrowth factor (k) was calculated by the best exponential fit [with a form $f(d)=Ae^{kd}$] to the measured volumes over the days (d). CI was calculated for each treatment group as $$CI = 1 - \frac{k}{k_{ctr}} \quad (B1)$$

where k is the tumor regrowth factor for each group and $k_{ctr}$ is the regrowth factor for the control group, which consisted of tumors exposed to neither BPD nor light illumination.

Reactive Oxygen Species Explicit Dosimetry

Type II PDT process can be described by a set of kinetic equations which can be simplified to describe the creation of $[ROS]_{rx}$.[21,22] These equations are dependent on the temporal and spatial distribution of ø, photosensitizer concentration ($[S_0]$), ground state oxygen concentration ([ROS]), and the photosensitizer-specific reaction-rate parameters (β and ξ). The relevant equations are:

$$[ROS]_{rx} = \int_{t=0}^{T} \xi \frac{[^3O_2]}{[^3O_2]+\beta} \phi [S_0] dt \quad (B2)$$

where φ is the light fluence rate, S is the source term, $\mu_a$ and $\mu_s'$ are the absorption and reduced scattering coefficients, respectively. The five parameters involved in the kinetic equations are photosensitizer-specific and details of each can be found elsewhere.[21] ξ is the photochemical oxygen consumption rate per light fluence rate and photosensitizer concentration under ample ROS supply. β represents the ratio of the monomolecular decay rate of the triplet state photosensitizer to the bimolecular rate of the triplet photosensitizer quenching by ROS. g is the maximum macroscopic oxygen perfusion rate. The reacted oxygen species concentration ($[ROS]_{rx}$) used as a dosimetric measure in other studies was calculated and compared using an initial ground state oxygen concentration of ($[ROS]_0$) of 40 µM, the measured $[ROS]_0$, the measured $[ROS]_{(t)}$ throughout treatment, and the [ROS] determined with blood flow changes measured during treatment. The two parameters used in Eq. (B2) are obtained from literature: $\xi=(55\pm15)\times10^{-3}$ cm$^2$ s$^{-1}$ mW$^{-1}$ and β=11.9 M.[1]

Results and Discussion

Figure 18:
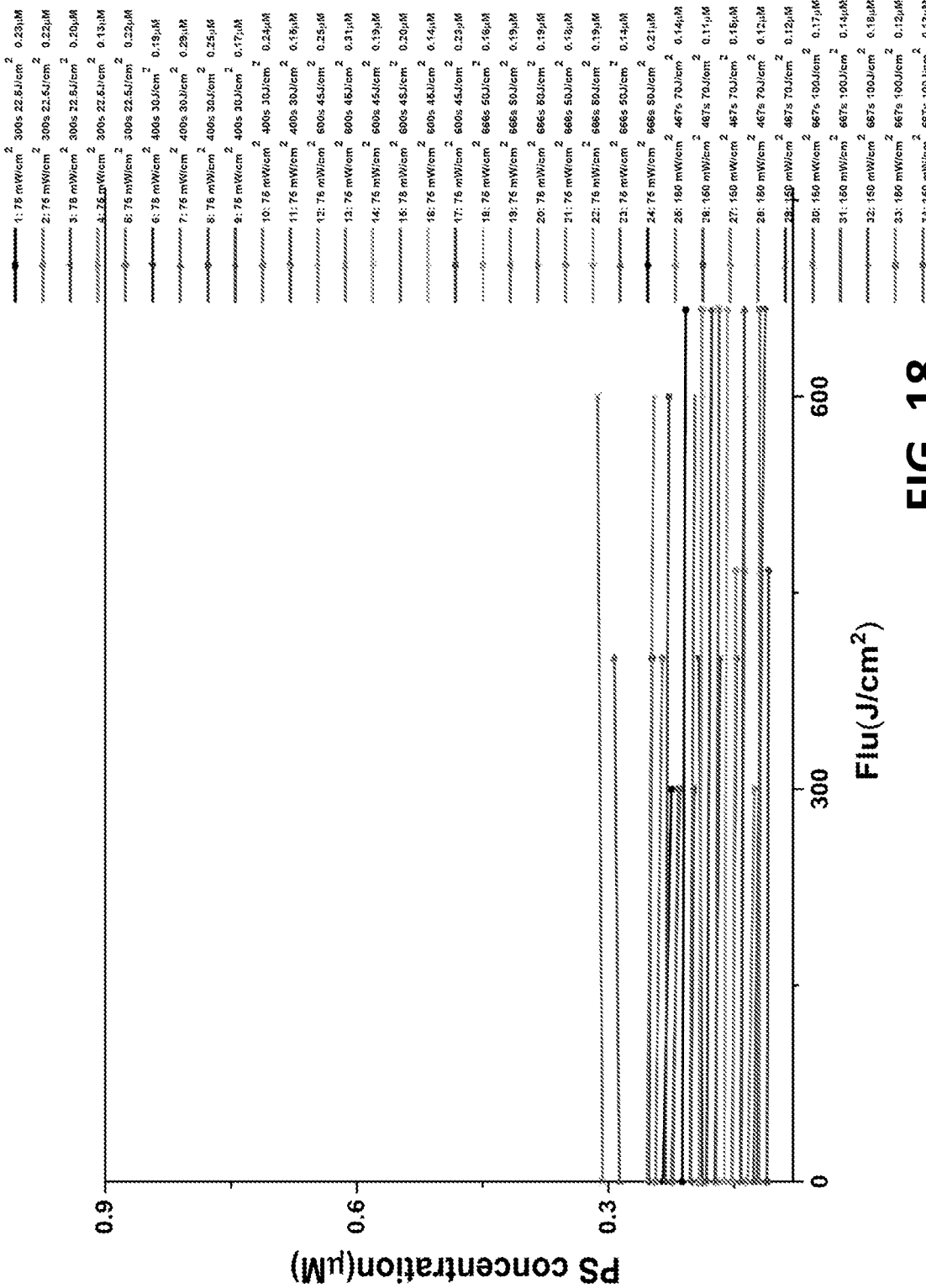
FIG. 18 shows BPD concentration versus fluence at 3 mm tumor depth for various treatment conditions.

BPD-mediated PDT with different in-air fluences, different $\phi_{air}$, and different exposure times was performed in mouse models bearing RIF tumors. Tissue optical properties, photosensitizer concentration, and tissue oxygenation were measured to calculate PDT dose, and $[ROS]_{rx}$. Table 6 summarizes all of the treatment conditions, FIG. 18 shows BPD concentration versus fluence at 3 mm tumor depth for various treatment conditions. The lines indicate the calculated change in photosensitizer concentration during light delivery for PDT.

BPD concentration was measured both before and after PDT treatment. It is shown in FIG. 18, the symbols represent the measured values, and the solid lines are model-calculated photosensitizer concentration during treatment. There are not significant changes.

Figure 19:
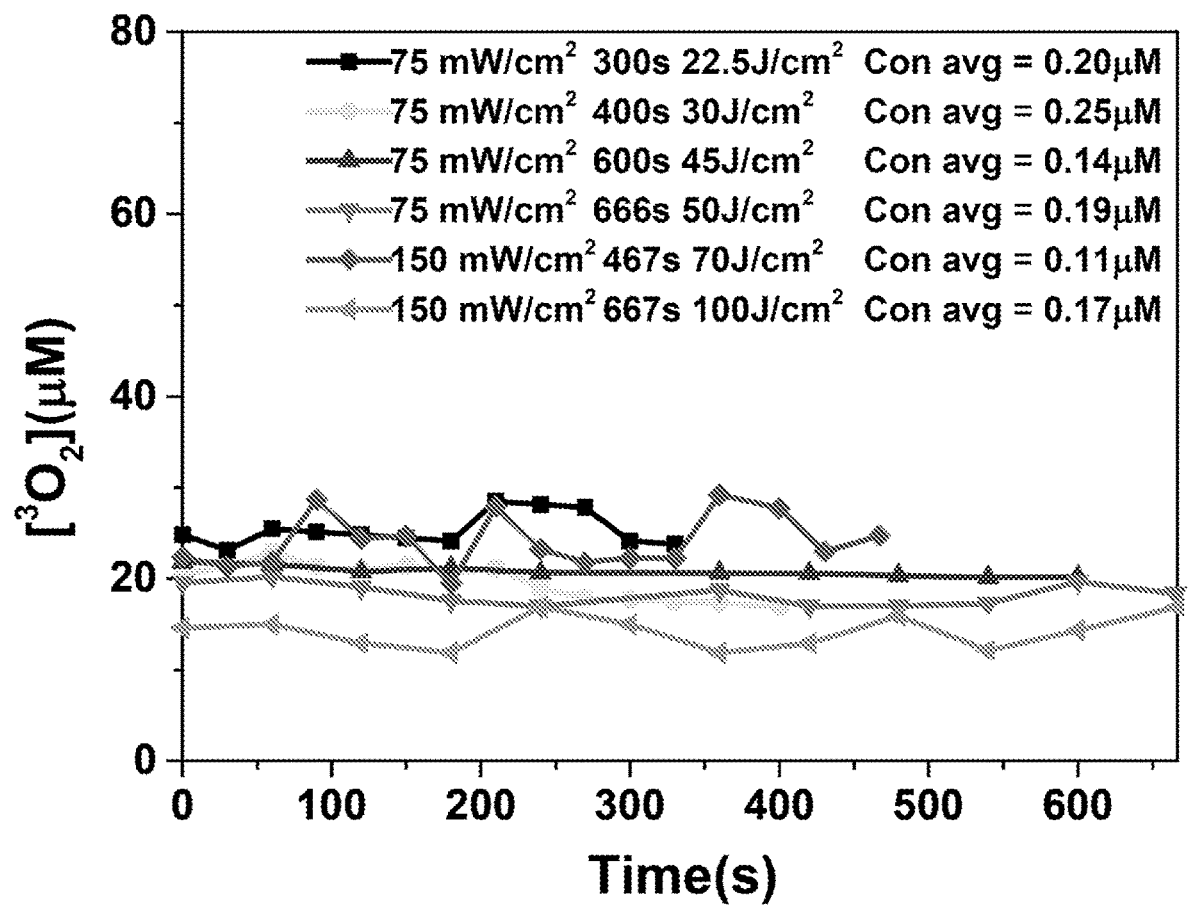
FIG. 19 shows temporal changes in ROS concentration during light for PDT with various treatment conditions.

FIG. 19 shows temporal changes in ROS concentration during light for PDT with various treatment conditions. The lines represent the calculated changed in ROS concentration during treatment.

Measured $[^3O_2]$ was used to refine the photochemical parameters previously determined for the reactive oxygen species explicit dosimetry model used to calculate $[ROS]_{rx}$, Individually, measured $[^3O_2]_{(t)}$ for each mouse was used as shown FIG. 19. There are no significant changes during the treatment.

Figure 20C:
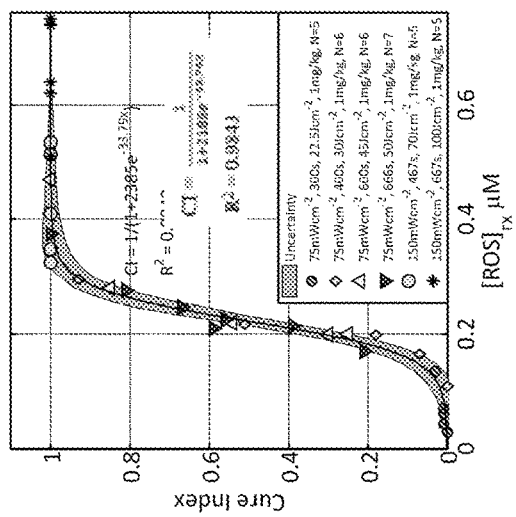
FIG. 20C shows cure index plotted as a function of mean reacted oxygen species at 3 mm depth ($[ROS]_{rx}$).
Figure 20B:
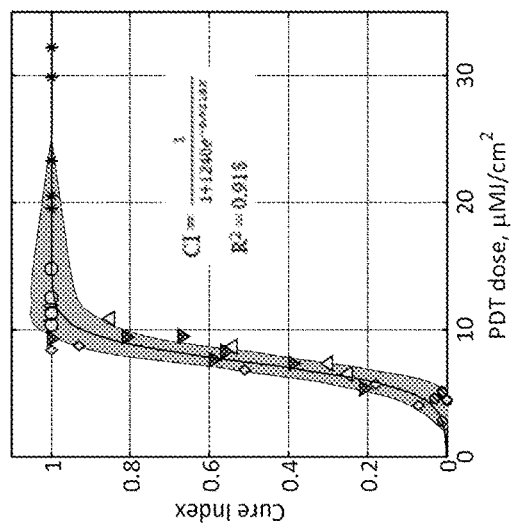
FIG. 20B shows cure index plotted as a function of calculated PDT dose at 3 mm depth.
Figure 20A:
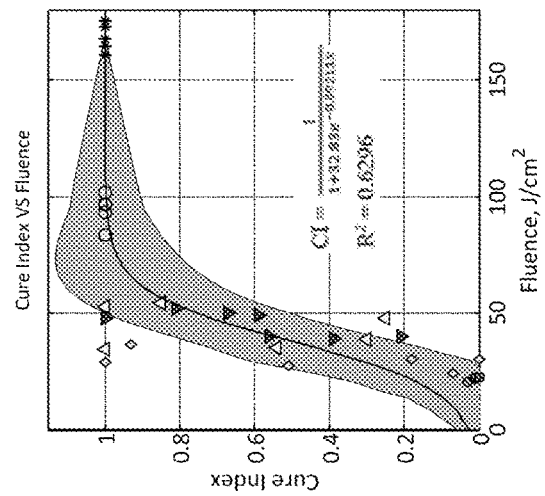
FIG. 20A shows cure index plotted as a function of fluence at a 3 mm tumor depth.

FIG. 20A shows cure index (CI) plotted as a function of fluence at a 3 mm tumor depth. FIG. 20B shows CI plotted as a function of calculated PDT dose at 3 mm depth. FIG. 20C shows CI plotted as a function of mean reacted oxygen species at 3 mm depth ($[ROS]_{rx}$) calculated using Eq. (B2) and the parameters summarized are $\xi=(55\pm15)\times10^{-3}$ cm$^2$ s$^{-1}$ mW$^{-1}$ and β=11.9 µM. The solid lines show the best-fit to the data with functional forms $$CI = \frac{1}{1+32.83e^{-0.09211x}},$$

$$CI = \frac{1}{1+1240e^{-0.9218x}}, \text{ and } \frac{1}{1+2188e^{-33.79x}}$$

with $R^2$=0.6296, 0.918 and 0.9843 for FIGS. 20A, 20B, and 20C, respectively. The gray region indicates the upper and lower bounds of the fit with 95% confidence level.

Fluence, PDT dose and calculated $[ROS]_{rx}$ at 3 mm were compared as dosimetric quantities to estimate the outcome of BPD-mediated PDT for RIF tumors. Outcome was quantified by the calculation of CI. If there is no tumor regrowth up to 14 days after treatment, then CI=1. PDT dose is calculated using the product of PS uptake and measured light fluence rate at 3 mm. The fluence rate at 3 mm is determined. We used Eq. (B2)[19] and photochemical parameters (ξ and β) obtained from literature[13] to calculate $[ROS]_{rx}$. The goodness of the fit and the corresponding upper and lower bounds of the fits (gray area) to the fluence, PDT dose and the calculated $[ROS]_{rx}$ are presented in FIGS. 20A-C. FIG. 20A shows that, while fluence correlates sigmoidal with the PDT outcome, it exhibits large uncertainties as defined by the large bounds of the gray area, as well as by the low value of $R^2$=0.6296. As shown in FIG. 20B, PDT dose allows for reduced subject variation and improved predictive efficacy as compared to fluence and measured $[ROS]_{rx}$. PDT dose showed a better correlation with CI with a higher value of $R^2$=0.918 and a narrower band of gray area as it accounts for both light dose and tissue [BPD] levels. However, PDT dose overestimates $[ROS]_{rx}$ in the presence of hypoxia as it does not account for the oxygen dependence of ROS quantum yield. The goodness of fit $R^2$=0.9843 and the narrowest gray area in FIG. 20C shows that the measured

[ROS]$_{rx}$ correlates the best with CI. [ROS]$_{rx}$ accounts for the key quantities of light fluence, photosensitizer concentration, and tissue oxygen level.

Conclusion

The response of mouse RIF tumors to PDT depends on tissue oxygenation, photosensitizer uptake, total energy delivered, and the @ at which treatment is delivered. An accurate dosimetry quantity for the evaluation of treatment outcome should account for all of these parameters. This study evaluated the efficacy and outcomes of different PDT treatments and how fluence, PDT dose, and [ROS]$_{rx}$ compare as dosimetric quantities. The correlation between CI and [ROS]$_{rx}$ suggests that [ROS]$_{rx}$ at 3 mm is the best quantity to predict the treatment outcome for a clinically relevant tumor regrowth endpoint. PDT dose is a better dosimetric quantity than fluence, but it is worse than [ROS]$_{rx}$ as it does not account for the consumption of [$^3O_2$] for different φ. For BPD in RIF tumors, the temporal dependence of in-vivo oxygen concentration during PDT can't be well modeled by our macroscopic model (for measurement [ROS], $R^2$=0.9843). This implies that it is important to make ROSED measurements during PDT to determine [ROS]$_{rx}$, in conjunction with the photochemical parameters required in Eq. B2. This study determines the [ROS]$_{rx}$ threshold dose for vascular BPD-mediated PDT for the first time.

REFERENCES FOR EXAMPLE 2

[1] Agostinis P., Berg K., Cengel K. A., et al., "Photodynamic therapy of cancer: an update," CA: *a cancer journal for clinicians* 61(4), 250-81 (2011).

[2] Castano A. P., Demidova T. N., Hamblin M. R., "Mechanisms in photodynamic therapy: part one-photosensitizers, photochemistry and cellular localization," *Photodiagnosis and photodynamic therapy* 1(4), 279-93 (2004).

[3] Penjweini R., Kim M. M., Liu B., Zhu T. C., "Evaluation of the 2-(1-Hexyloxyethyl)-2-devinyl pyropheophorbide (HPPH) mediated photodynamic therapy by macroscopic singlet oxygen modeling," *Journal of Biophotonics* 9(11-12), 1344-1354 (2016).

[4] Qiu H., Kim M. M., Penjweini R., Zhu T. C., "Macroscopic singlet oxygen modeling for dosimetry of Photofrin-mediated photodynamic therapy: an in-vivo study," *Journal of biomedical optics* 21(8), 88002 (2016).

[5] Wang, K. K. H., Finay, J. C., Busch, T. M. et al., "Explicit dosimetry for photodynamic therapy: macroscopic singlet oxygen modeling," Journal of Biophotonics, 3(5-6), 304-318 (2010).

[6] Liang, X., Wang, K. K. H., Zhu, T. C., "Singlet oxygen dosimetry modeling for photodynamic therapy," Proc. SPIE, 8210, 8210T-1-8210T-7 (2012).

[7] Mcillan, D. D., Chen, D., Kim, M. M., Liang, X., Zhu, T. C., "Parameter determination for singlet oxygen modeling of BPD-mediated PDT," Proc. SPIE, 8568, 856810-1-856810-8 (2013).

[8] Zhu, T. C., Finlay, J. C., Zhou, X., Li, J., "Macroscopic modeling of the singlet oxygen production during PDT," Proc. SPIE, 6427, 642708-1-642708-12 (2007).

[9] Chen, B., Pogue, B. W., Luna, J. M., Hardman, R. L., Hoopes, P. J., Hasan, T., "Tumor Vascular Permeabilization by Vascular-Targeting Photosensitization: Effects, Mechanism, and Therapeutic Implications," Clin. Cancer Res, 12(1), 917-23 (2006).

[10] K. K. Wang et al., "Explicit dosimetry for photodynamic therapy: macroscopic singlet oxygen modeling," J. Biophoton. 3(5-6), 304-318 (2010).

[11] T. C. Zhu et al., "In-vivo singlet oxygen threshold doses for PDT," Photon. Lasers Med. 4(1), 59-71 (2015).

[12] B. Liu et al., "Comparison of PDT parameters for RIF and H460 tumor models during HPPH-mediated PDT," Proc. SPIE 8931 89311C (2014).

[13] M. M. Kim. A A Ghogare, A Greer and T. C. Zhu, "On the in vivo photochemical rate parameters for PDT reactive oxygen species modeling". Phys. Med. Biol. 00(2016) 1-48.

[14] Qiu, H., Kim, M. M., Penjweini, R., Zhu, T. C., "Dosimetry study of PHOTOFRIN-mediated photodynamic therapy in a mouse tumor model," Proc. SPIE 9694, 96940T (2016).

[15] Penjweini, R., Liu, B., Kim, M. M., Zhu, T. C., "Explicit dosimetry for 2-(1-hexyloxyethyl)-2-devinyl pyropheophorbide-a-mediated photodynamic therapy: macroscopic singlet oxygen modeling," Journal of biomedical optics 20(12), 128003 (2015).

[16] R. C. Mesquita et al., "Tumor blood flow differs between mouse strains: consequences for vasoresponse to photodynamic therapy," PLOS One 7(5), e37322 (2012).

[17] R. Penjweini, M. M. Kim, B. Liu, and T. C. Zhu, "Evaluation of the 2-(1-Hexyloxyethyl)-2-devinylpyropheophorbide (HPPH) mediated photodynamic therapy by macroscopic singlet oxygen modeling," *J. Biophotonics* 9(11-12): 1344-1354 (2016).

[18] H. Qiu, M. M. Kim, R. Penjweini, and T. C. Zhu, "Macroscopic singlet oxygen modeling for dosimetry of Photofrin-mediated photodynamic therapy: an in vivo study," *J. Biomed. Opt.* 21(8): 088002 (2016).

[19] M. M. Kim, R. Penjweini, and T. C. Zhu, "Evaluation of singlet oxygen explicit dosimetry (SOED) for predicting treatment outcomes of benzoporphyrin derivative monoacid ring A (BPD-MA)-mediated photodynamic therapy," *J. Biomed. Opt.* 22(2): 028002 (2017).

[20] T. M. Busch et al., "Fluence rate-dependent intratumor heterogeneity in physiologic and cytotoxic responses to photofrin photodynamic therapy," Photochem. Photobiol. Sci. 8(12), 1683-1693 (2009).

[21] M. M. Kim, R. Penjweini, Y. H. Ong and T. C. Zhu, "Singlet oxygen explicit dosimetry to predict long-term local tumor control for BPD-mediated photodynamic therapy," Proc. SPIE 10047, 100470X (2018).

[22] Hu X. H., Feng Y., Lu J. Q., et al., "Modeling of a type II photofrin-mediated photodynamic therapy process in a heterogeneous tissue phantom," *Photochemistry and photobiology* 81(6), 1460-8 (2005).

Example 3—Reactive Oxygen Species Explicit Dosimetry to Predict Local Tumor Control for Photofrin-Mediated Photodynamic Therapy Although photodynamic therapy (PDT) is an established modality for cancer treatment, current dosimetric quantities, such as light fluence and PDT dose, do not account for the differences in PDT oxygen consumption for different fluence rates (φ). A macroscopic model was adopted to calculate reactive oxygen species concentration ([ROS]$_{rx}$) to predict Photofrin-PDT outcome in mice bearing radiation-induced fibrosarcoma (RIF) tumors. Singlet oxygen is the primary cytotoxic species for ROS, which is responsible for cell death in type II PDT, although other type I ROS is included in the parameters used in our model. Using a combination of fluences (50-250 J/cm$^2$) and φ (50-150 mW/cm$^2$), tumor regrowth rate, k, was determined for each condition by fitting the tumor volume vs. time to $V_0$*exp (k*t). Treatment was delivered with a collimated laser beam of 1 cm diameter at 630 nm. Explicit dosimetry of initial tissue oxygen concentration, tissue optical properties, and Photofrin concentration was used to calculate $[ROS]_{rx,cal}$. $\phi$ was determined for the treatment volume based on Monte-Carlo simulations and measured tissue optical properties. Tissue oxygenation is measured using an oxylite oxygen probe to throughout the treatment to calculate the measured $[ROS]_{rx,mea}$. Cure index, $CI=1-k/k_{ctr}$, for tumor growth up to 14 days were determined as an endpoint using five dose metrics: light fluence, PDT dose, and $[ROS]_{rx,cal}$, and $[ROS]_{rx,mea}$. PDT dose was defined as the product of the time-integral of photosensitizer concentration and ø at a 3 mm tumor depth. Preliminary studies show that $[ROS]_{rx,mea}$ best correlates with CI and is an effective dosimetric quantity that can predict treatment outcome.

Photodynamic therapy (PDT) is currently undergoing intensive clinical investigations as an adjuvant treatment for proliferative disorders including cancer.[1-3] PDT involves the administration of a photosensitizer, which preferentially accumulates in diseased cells, followed by light excitation at a specific wavelength.[3,4] PDT is dynamic and multifaceted with the interactions between a treatment light at a particular wavelength, a photosensitizer, and tissue oxygenation $([^3O_2])$.[2] At Photofrin-PDT, the photosensitizer undergoes mostly type II processes upon photoexcitation in which the triplet state transfers energy to $^3O_2$ to produce singlet oxygen (ROS).[5,6] Generation of reactive $^1O_2$ $([ROS]_{rx})$ causes cytotoxicity and eventually cell death and/or therapeutic effects[6].

The results of our study using additional real-time measurements of Photofrin concentration and $[^3O_2]$ result in reduced uncertainties for correlations between cure index at 14 days and the measured reactive oxygen species, $[ROS]_{rx,mea}$.

Materials and Methods

Tumor Model and PDT Treatment Conditions

Radiation-induced fibrosarcomas (RIF) cells were cultured and injected in the right shoulder regions of 6-8 weeks old female $C_3H$ mice (NCI-Frederick, Frederick, MD). 30 μl were injected at a concentration of $1\times10^7$ cells/ml, as described previously.[8-11] Animals were under the care of the University of Pennsylvania Laboratory Animal Resources. All studies were approved by the University of Pennsylvania Institutional Animal Care and Use Committee. The fur of the treatment region was clipped prior to cell inoculation, and the treatment area was depilated with Nair (Church & Dwight Co., Inc., Ewing, NJ) at least 24 hours prior to measurements and treatment. Tumors were treated when they were 3~5 mm in diameter. Mice were given a chlorophyll-free (alfalfa-free) rodent diet (Harlan laboratories Inc., Indianapolis, IN) at least 10 days prior to treatment to eliminate the fluorescence signal from chlorophyll-breakdown products, which have a similar range to the photosensitizer spectra obtained in this study. The photosensitizer fluorescence was used to determine the in vivo concentrations in this study, using methods described previously.[7-9]

Treatment delivery was done using an optical fiber with a microlens attachment coupled to a diode laser with the appropriate wavelength for each photosensitizer. A 630 nm laser (Biolitec, Inc., East Longmeadow, MA, USA) was used for Photofrin after a 18~24 hours drug-light interval. The in-air fluence rate ($\phi_{air}$) is defined as the calculated irradiance determined by the laser power divided by the treatment area (1 cm diameter spot size). The in-air fluence was calculated by multiplying the in-air fluence rate by the treatment time. RIF tumor-bearing mice with no photosensitizer and no light excitation were used as controls (n=5). Treatment conditions are summarized in Table 7.

TABLE 7

| Index | Mice # | $\Phi(mW/cm^2)$ | Time(s) | Photofrin pre (μM) | Photofrin post(μM) | Fluence (Mw/cm²) | PDT Dose (μMj/cm²) | $[ROS]_{rxcal}$ (mM) | $[ROS]_{rx,mea}$ (mM) | CI |
|---|---|---|---|---|---|---|---|---|---|---|
| 1 | #10-1 | 150.00 | 333.00 | 6.80 | 3.07 | 28.99 | 136.00 | 0.29 | 0.27 | 0.03 |
| 2 | #10-2 | 150.00 | 333.00 | 3.07 | 1.19 | 43.36 | 87.00 | 0.235 | 0.27 | 0.00 |
| 3 | #11-5 | 150.00 | 333.00 | 5.84 | 2.80 | 42.42 | 175.00 | 0.39 | 0.21 | 0.01 |
| 4 | #12-5 | 150.00 | 333.00 | 5.10 | 2.30 | 38.18 | 134.00 | 0.32 | 0.38 | 0.06 |
| 5 | #11-1 | 75.00 | 3333.00 | 4.50 | 2.20 | 212.52 | 527.00 | 1.87 | 1.20 | 1.00 |
| 6 | #11-2 | 75.00 | 3333.00 | 6.47 | 3.02 | 195.78 | 673.00 | 2.33 | 1.40 | 1.00 |
| 7 | #11-3 | 75.00 | 3333.00 | 4.20 | 2.44 | 197.43 | 524.00 | 1.73 | 1.41 | 1.00 |
| 8 | #11-4 | 75.00 | 3333.00 | 4.54 | 2.48 | 205.21 | 560.00 | 1.89 | 1.39 | 1.00 |
| 9 | #12-1 | 75.00 | 1800.00 | 6.90 | 4.90 | 103.44 | 551.00 | 1.39 | 1.13 | 1.00 |
| 10 | #12-2 | 75.00 | 1800.00 | 6.80 | 3.35 | 116.56 | 476.00 | 1.24 | 0.96 | 0.56 |
| 11 | #12-3 | 75.00 | 1800.00 | 5.20 | 3.00 | 114.90 | 399.00 | 1.07 | 1.00 | 0.64 |
| 12 | #12-4 | 75.00 | 1800.00 | 5.67 | 3.50 | 104.00 | 414.00 | 1.09 | 1.10 | 0.82 |
| 13 | #13-1 | 75.00 | 1500.00 | 6.50 | 2.80 | 103.25 | 413.00 | 0.89 | 0.82 | 0.20 |
| 14 | #13-2 | 75.00 | 1500.00 | 6.70 | 3.70 | 88.36 | 387.00 | 0.93 | 0.73 | 0.22 |
| 15 | #13-3 | 75.00 | 1500.00 | 6.00 | 3.01 | 97.94 | 354.00 | 0.87 | 0.65 | 0.13 |
| 16 | #13-4 | 150.00 | 666.00 | 6.40 | 2.50 | 82.95 | 327.00 | 0.69 | 0.77 | 0.15 |
| 17 | #13-5 | 150.00 | 666.00 | 7.20 | 3.54 | 83.57 | 409.00 | 0.81 | 0.79 | 0.25 |
| 18 | #14-1 | 150.00 | 666.00 | 7.84 | 4.88 | 72.14 | 431.00 | 0.8 | 0.88 | 0.42 |
| 19 | #14-2 | 150.00 | 666.00 | 6.79 | 3.49 | 85.31 | 402.00 | 0.81 | 0.78 | 0.27 |

Table 7. In-air light fluence, in-air light fluence rate, photofrin concentration in tumors, initial tissue oxygenation, PDT dose, as well as calculated reactive oxygen species concentration. Methods to determine the calculated and measured $[ROS]_{rx,mea}$ and $[ROS]_{rx,calc}$ will be discussed in Section entitled "Reactive Oxygen Species Explicit Dosimetry" below.

Photodynamic Therapy Protocol

Photofrin (Pinnacle Biologics, Chicago, Illinois) at a dosage of 5 mg/kg was injected through the mouse tail vein as described previously.[12,13] At a 24-h drug-light interval, superficial irradiation of the tumor was performed with a 630-nm laser (Biolitec AG., A-1030, Vienna). A microlens fiber was coupled to the laser to irradiate the tumor uniformly. Animals were assigned to four light dose groups, and each group was comprised of 2 to 3 subgroups with different $\phi$. There were a total of 5 treatment groups: 50 J/cm² at 150 mW/cm², 250 J/cm² at 75 mW/cm², 135 J/cm² at 75 mW/cm², 75 J/cm² at 75 mW/cm², and 100 J/cm² at 150 mW/cm$^2$. Tumor-bearing mice that received neither light irradiation nor Photofrin were used as controls.

Photofrin Concentration

Following the drug-light interval of 18~24 hours, measurements of light fluence rate, photosensitizer concentration and [O$_2$] were performed. Photofrin fluorescence spectra was obtained using a custom-made multi-fiber contact probe before and after PDT.[14] The probe is connected to a 405 nm laser (Power Technology Inc., Little Rock, AR, USA) for the fluorescence excitation of Photofrin and a multichannel CCD spectrograph (InSpectrum, Princeton Instruments, Trenton, NJ, USA) for the collection of the spectra. The in vivo photosensitizer concentration was obtained by comparing the in vivo Photofrin spectra with those of phantoms with known photosensitizer concentrations. The attenuation of the fluorescence signal due to the light absorption and scattering by tissues was corrected by applying an empirical correction factor described elsewhere. The accuracy of in vivo measurements was validated by ex vivo measurements in separate mice.[15,16]

Oxygen Measurements

The in vivo tissue oxygen partial pressure $_pO_2$ was measured during PDT treatment using a phosphorescence-based $^3O_2$ probe (OxyLite Pro, Oxford Optronix, Oxford, United Kingdom). A bare-fiber-type probe (NX-BF/O/E, Oxford Optronix, Oxford, United Kingdom) was placed inside the tumor at a 3 mm depth from the treatment surface. The oxygen concentration ([O$_2$]) was calculated by multiplying the measured pO$_2$ with the O$_2$ solubility in tissue, which is 1.295 µM/mmHg.[5] Measured [O$_2$]$_0$ and [O$_2$](t) was used to calculate reacted oxygen species using the macroscopic singlet oxygen model.[4,5]

Tumor Regrowth Rate Analysis

Tumor volumes were measured daily after PDT. Width (a) and length (b) were measured with slide calibers, and tumor volumes (V) was calculated using V=π×a$^2$×b/6.[17] Tumor volumes were tracked for 14 days, and the tumor regrowth factor (k) was calculated by the best exponential fit [with a form f(d)=Ae$^{kd}$] to the measured volumes over the days (d). CI was calculated for each treatment group as $$CI = 1 - \frac{k}{k_{ctr}} \quad (C1)$$

where k is the tumor regrowth factor for each group and $k_{ctr}$ is the regrowth factor for the control group, which consisted of tumors to neither Photofrin nor light illumination.

Reactive Oxygen Species Explicit Dosimetry

Type II PDT process can be described by a set of kinetic equations which can be simplified to describe the creation of [ROS]$_{rx}$.[18,19] These equations are dependent on the temporal and spatial distribution of ϕ, photosensitizer concentration ([S$_0$]), ground state oxygen concentration ([$^3O_2$]), oxygen supply rate (g), and the photosensitizer-specific reaction-rate parameters (δ, β, σ, and ξ). The relevant equations are:

$$\frac{d[S_0]}{dt} = -\frac{[^3O_2]}{[^3O_2]+\beta}\phi[S_0]([S_0]+\delta)\phi\xi\sigma \quad (C2)$$

$$\frac{d[^3O_2]}{dt} = -\left(\xi\frac{\phi[^3O_2]}{[^3O_2]+\beta}\right)[S_0] + g\left(1 - \frac{[^3O_2]}{[^3O_2](t=0)}\right) \quad (C3)$$

$$\frac{d[^1O_2]_{rx}}{dt} - \left(\xi\frac{\phi[S_0][^3O_2]}{[^3O_2]+\beta}\right) = 0 \quad (C4)$$

$$[ROS]_{rx} = \int_{t=0}^{T} \xi\frac{[^3O_2]}{[^3O_2]+\beta}\phi[S_0]dt \quad (C5)$$

where ϕ is the light fluence rate, S is the source term, µ$_a$ and µ$_s'$ are the absorption and reduced scattering coefficients, respectively. The five parameters involved in the kinetic equations are photosensitizer-specific and details of each can be found elsewhere.[18] ξ is the photochemical oxygen consumption rate per light fluence rate and photosensitizer concentration under ample $^3O_2$ supply. σ is the probability ratio of a $^1O_2$ molecule to react with ground state photosensitizer compared to the $^1O_2$ molecule reacting with a cellular target. β represents the ratio of the monomolecular decay rate of the triplet state photosensitizer to the bimolecular rate of the triplet photosensitizer quenching by $^3O_2$. δ is the low concentration correction factor, and g is the maximum macroscopic oxygen perfusion rate. The reacted oxygen species concentration ([ROS]$_{rx}$) used as a dosimetric measure in other studies was calculated and compared using an initial ground state oxygen concentration of ([$^3O_2$]$_0$) of 40 µM, the measured [$^3O_2$]$_{(t)}$ throughout treatment.

For each spatial location, [S$_0$]$_{(t)}$ and [$^3O_2$]$_{(t)}$ can be calculated by solving the coupled differential equations [Eqs. (C2) and (C4)] using the initial conditions for [S$_0$]$_0$ based on fluorescence measurement before PDT and its assumed spatial homogeneous, the initial [$^3O_2$]$_0$ value (from FIG. 22), and ϕ(d). The light fluence rate does not change with time. Finally, [$^1O_2$]$_{rx}$ is calculated using Eq. (C4).[15,22] We also measure the temporal value [$^3O_2$]$_{(t)}$. And then we use the calculated [$^3O_2$]$_{(t)}$ and measure [$^3O_2$]$_{(t)}$ in the Eq. (C5), and get the [ROS]$_{rx\_cal}$ and [ROS]$_{rx\_mea}$.

Results and Discussion

Photofrin-mediated PDT with various in-air fluences, ϕ$_{air}$, and exposure times were performed in mouse models bearing RIF tumors. Tissue optical properties, photosensitizer concentration, and tissue oxygenation were measured to PDT dose, and [ROS]$_{rx}$. Table 7 summarizes all of the treatment conditions, as well as the measured and calculated quantities using the photochemical parameters summarized in Table 8.

Figure 21:
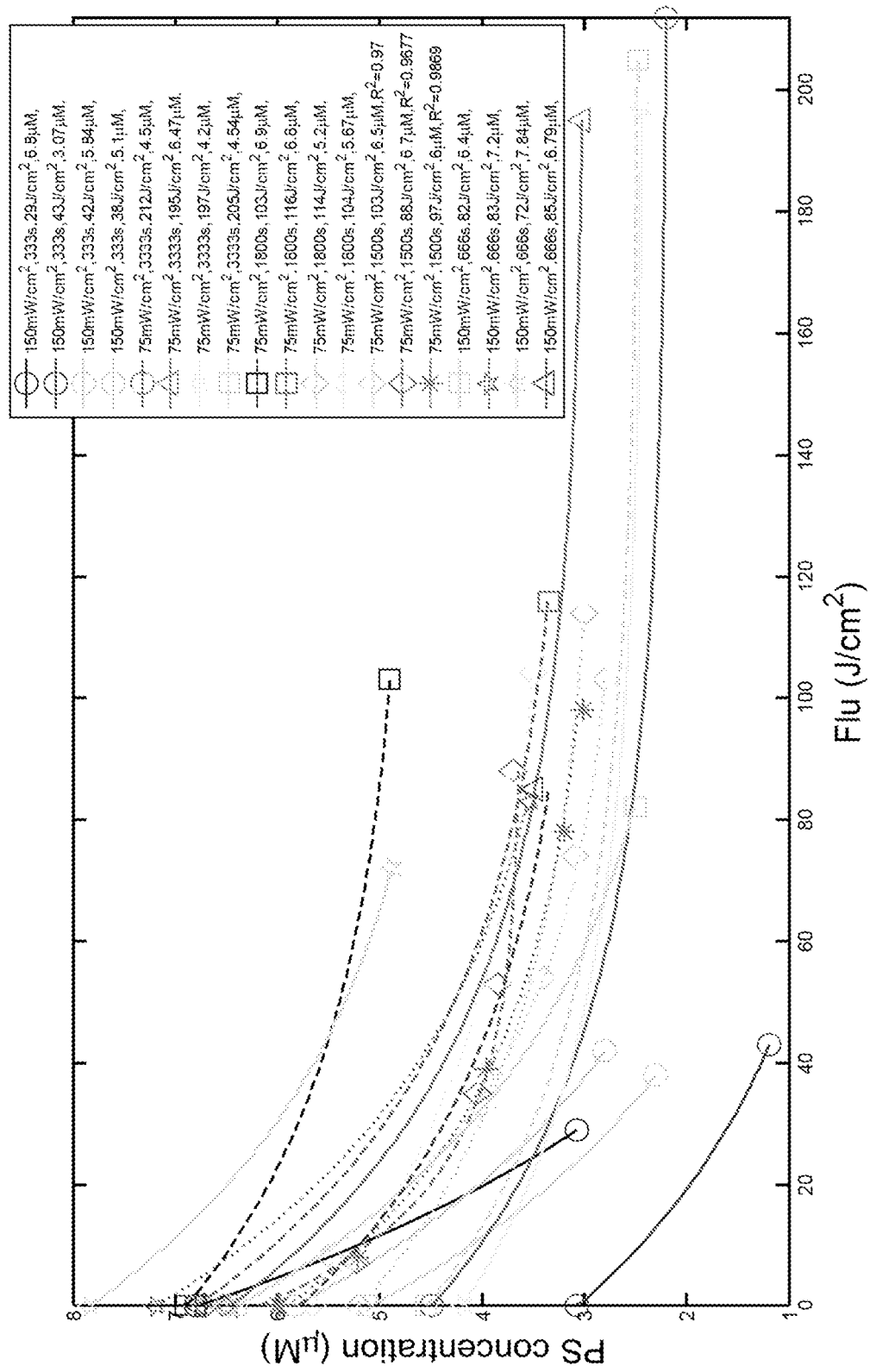
FIG. 21 shows Photofrin concentration versus fluence at 3 mm tumor depth for various treatment conditions.

Photofrin concentration ([Photofrin]) was measured both before and after PDT treatment. And some of them were measured in process PDT treatment. Measured [Photofrin] was compared to model calculated values for all of the treatment conditions and is shown in FIG. 21. The symbols represent the measured values, and the solid lines are model-calculated photosensitizer concentration during treatment.

FIG. 21 shows Photofrin concentration versus fluence at 3 mm tumor depth for various treatment conditions. The lines indicate the calculated change in photosensitizer concentration during light delivery for PDT.

TABLE 8

| Parameter | Definition | Value |
|---|---|---|
| ξ (cm$^2$s$^{-1}$mW$^{-1}$) | Specific oxygen consumption rate | 3.7 × 10$^{-3}$ |
| σ (µM$^{-1}$) | Specific photobleaching ratio | 7.6 × 10$^{-5}$ |

TABLE 8-continued

| Parameter | Definition | Value |
| --- | --- | --- |
| β (μM) | Oxygen quenching threshold concentration | 11.9 |
| δ (μM) | Low concentration correction | 33 |
| g (μM/s) | Macroscopic oxygen maximum perfusion rate | 0.76 |

Table 8: Preliminary photochemical parameters obtained from literature.[10]

Figure 22:
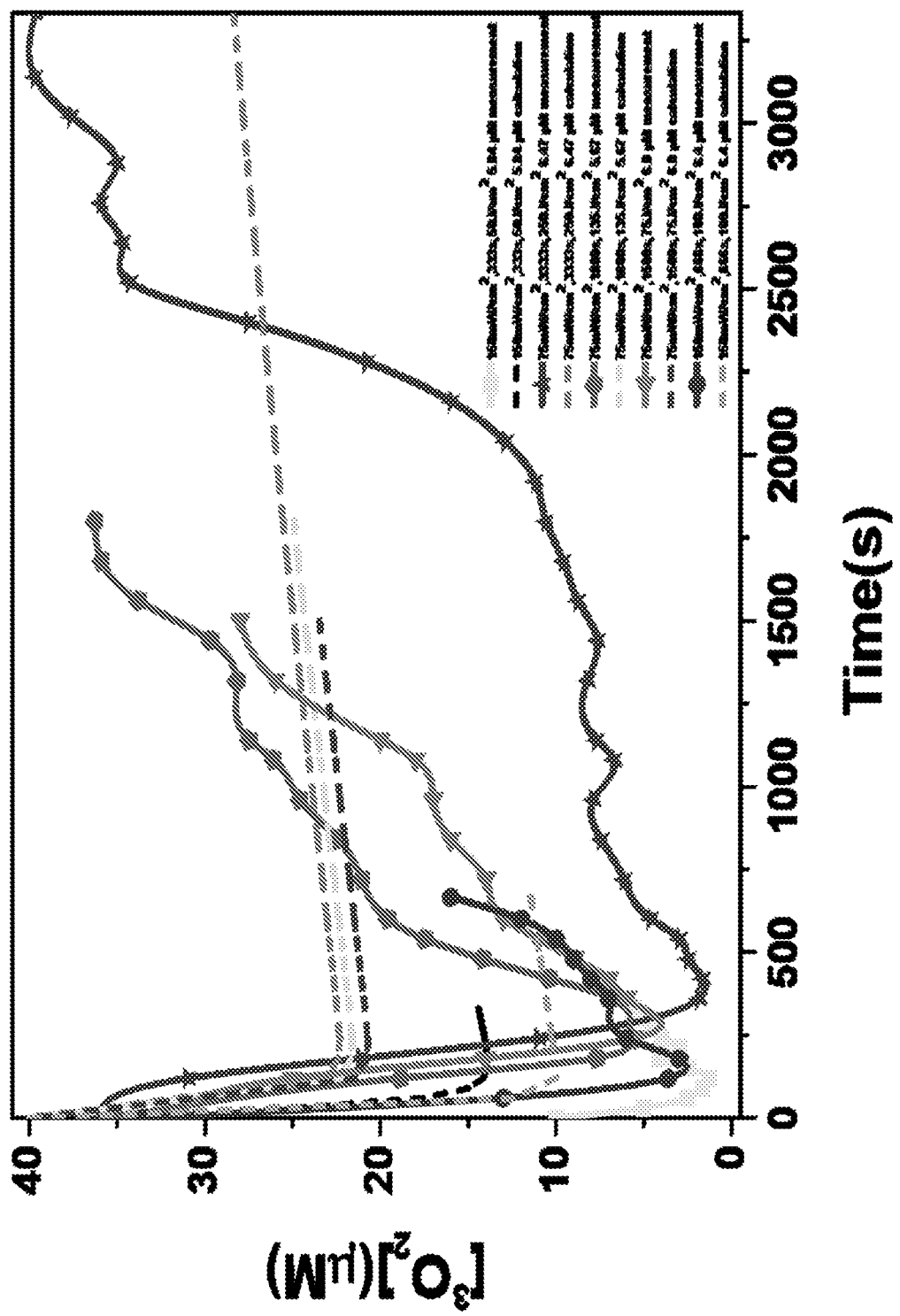
FIG. 22 shows temporal changes in $^3O_2$ concentration during light for PDT with various treatment conditions.

FIG. 22 shows Temporal changes in $^3O_2$ concentration during light for PDT with various treatment conditions. The lines represent the calculated changed in $^3O_2$ concentration during treatment.

Measured [$^3O_2$] was used to refine the photochemical parameters previously determined[20] for the reactive singlet explicit dosimetry model used to calculate $[ROS]_{rx}$. Individually measured $[^3O_2]_{(t)}$ for each mouse were fit with the model-calculated values. Measured data are shown with symbols and calculated [$^3O_2$] are shown as dashed lines in FIG. 22.

FIG. 23A shows cure index (CI) plotted as a function of fluence at a 3 mm tumor depth. FIG. 23B shows CI plotted as a function of calculated PDT dose at 3 mm tumor depth. FIG. 23C shows CI plotted as a function of calculation ROS at 3 mm tumor depth. FIG. 23D shows CI plotted as a function of mean reacted singlet oxygen at 3 mm depth ($[ROS]_{rx}$) calculated using Eqs. (C3)~ (C6) and the parameters summarized in Table 8. The solid lines show the best-fit to the data with functional forms $$CI = \frac{1}{1 + 223.4e^{-0.05269x}},$$

$$CI = \frac{1}{1 + 9971e^{-0.02098x}},$$

$$CI = \frac{1}{1 + 144.6e^{-5.221x}} \text{ and}$$

$$CI = \frac{1}{1 + 6480e^{-9.151x}}$$

with $R^2$=0.777, 0.8744, 0.93 and 0.972 for FIGS. 23A, 23B, 23C, and 23D, respectively. The gray region indicates the upper and lower bounds of the fit with 95% confidence level.

Fluence, PDT dose, calculated $[ROS]_{rx,cal}$ at 3 mm and measured $[ROS]_{rx,mea}$ at 3 mm were compared as dosimetric quantities to estimate the outcome of photofrin-mediated PDT for RIF tumors. Outcome was quantified by the calculation of CI. No tumor regrowth up to 14 days after treatment resulted in a CI of 1. PDT dose is calculated using the product of PS uptake and measured light fluence rate at 3 mm. The fluence rate at 3 mm is determined. We used the Eq. (C6)[22] and the preliminary photochemical parameters shown in Table 8[7] to calculated $[ROS]_{rx,cal}$ and measured $[ROS]_{rx,mea}$ using model calculated [$^3O_2$] and measured $[^3O_2]_{(t)}$, respectively. The goodness of the fit and the corresponding upper and lower bounds of the fits (gray area) to the fluence, PDT dose, calculated $[ROS]_{rx,cal}$ and the measured $[ROS]_{rx,mea}$ are presented in FIGS. 23A-D. FIG. 23A shows that, while fluence correlates sigmoidal with the PDT outcome, it exhibits large uncertainties as defined by the large bounds of the gray area, as well as by the low value of $R^2$=0.777. As shown in FIG. 23B, PDT dose allows for reduced subject variation and improved predictive efficacy as compared to fluence, calculated $[ROS]_{rx,cal}$ and measured $[ROS]_{rx,mea}$. PDT dose showed a better correlation with CI with a higher value of $R^2$=0.8744 and a narrower band of gray area as it accounts for both light dose and tissue [photofrin] levels. However, PDT dose overestimates $[ROS]_{rx}$ in the presence of hypoxia as it does not account for the oxygen dependence of ROS quantum yield. The goodness of fit $R^2$=0.93, $R^2$=0.972 and the narrowest gray area in FIGS. 23C and 23D shows that the calculated $[ROS]_{rx,cal}$ and the measured $[ROS]_{rx,mea}$ correlates the best with CI. $[ROS]_{rx}$ accounts for the key quantities of light fluence, photosensitizer concentration, and tissue oxygen level, respectively. The result that $R^2$ value of the measured $[ROS]_{rx,mea}$ is better than the calculated $[ROS]_{rx,cal}$.

The PDT dose threshold (439 mM J/cm$^2$) due obtain in this study is comparable to results published studies in literature 306 mM J/cm$^2$ in in-vitro condition[20,21]. But it is substantially smaller than that obtain from our previous study (1200 mM J/cm$^2$)[22]. The reason for this different is because the tumor size in the current study is substantially smaller and less variable them the previous study (100 cc vs. 400 cc). This also explain why the relationship between CI. vs. Ø or CI. vs. PDT dose a sigmoid shape in the current study while no threshold dose behave was observed in the previous.

Conclusion

The response of mouse RIF tumors to PDT depends on tissue oxygenation, photosensitizer uptake, total energy delivered, and the ø at which treatment is delivered. An accurate dosimetry quantity for the evaluation of treatment outcome should account for all of these parameters. This study evaluated the efficacy and outcomes of different PDT treatments and how fluence, PDT dose, and $[ROS]_{rx}$ compare as dosimetric quantities. The correlation between CI and $[ROS]_{rx}$ suggests that $[ROS]_{rx}$ at 3 mm is the best quantity to predict the treatment outcome for a clinically relevant tumor regrowth endpoint. PDT dose is a better dosimetric quantity than fluence, but it is worse than $[ROS]_{rx}$ as it does not account for the consumption of [$^3O_2$] for different ϕ. For Photofrin in RIF tumors, the temporal dependence of in-vivo oxygen concentration during PDT can't be well modeled by our macroscopic model (for measurement [$^3O_2$], $R^2$=0.972). This implies that it is not necessary to make [$^3O_2$] measurements during PDT to obtain $[ROS]_{rx}$, and use these values in conjunction with our model. This study validated the model and photochemical parameters for Photofrin-mediated PDT for an endpoint that is clinically relevant. This is being reported for the first time.

REFERENCES FOR EXAMPLE 3

[1] Agostinis P., Berg K., Cengel K. A., et al., "Photodynamic therapy of cancer: an update," *CA: a cancer journal for clinicians* 61(4), 250-81 (2011).
[2] Castano A. P., Demidova T. N., Hamblin M. R., "Mechanisms in photodynamic therapy: part one-photosensitizers, photochemistry and cellular localization," *Photodiagnosis and photodynamic therapy* 1(4), 279-93 (2004).
[3] Agostinis, P., Berg, K., Cengel, K. A., et al., "Photodynamic therapy of cancer: an update," CA: a cancer journal for clinicians 61(4), 250-281 (2011).
[4] Penjweini, R., Loew, H-G., Breit, P., Kratky, K. W., "Optimizing the antitumor selectivity of PVP-Hypericin re A549 cancer cells and HLF normal cells through pulsed blue light," Photodiagnosis and photodynamic therapy 10(4), 591-599 (2013).
[5] Penjweini, R., Liu, B., Kim, M. M., Zhu, T. C., "Explicit dosimetry for 2-(1-hexyloxyethyl)-2-devinyl pyropheophorbide-a-mediated photodynamic therapy: macroscopic singlet oxygen modeling," Journal of biomedical optics 20(12), 128003 (2015).

[6] Qiu, H., Kim, M. M., Penjweini, R., Zhu, T. C., "Macroscopic singlet oxygen modeling for dosimetry of Photofrinmediated photodynamic therapy: an in-vivo study," Journal of biomedical optics 21(8), 88002 (2016).

[7] Penjweini, R., Kim, M. M., Liu, B., Zhu, T. C., "Evaluation of the 2-(1-Hexyloxyethyl)-2-devinyl pyropheophorbide (HPPH) mediated photodynamic therapy by macroscopic singlet oxygen modeling," Journal of Biophotonics 9(11-12), 1344-1354 (2016).

[8]. K. K. Wang et al., "Explicit dosimetry for photodynamic therapy: macroscopic singlet oxygen modeling," J. Biophoton. 3(5-6), 304-318 (2010).

[9]. T. C. Zhu et al., "Comparison of singlet oxygen threshold dose for PDT," Proc. SPIE 8931, 89310I (2014).

[10]. M. M. Kim. A A Ghogare, A Greer and T. C. Zhu, "On the in vivo photochemical rate parameters for PDT reactive oxygen species modeling". Phys. Med. Biol. 00(2016) 1-48.

[11]. B. Liu et al., "Comparison of PDT parameters for RIF and H460 tumor models during HPPH-mediated PDT," Proc. SPIE 8931 89311C (2014).

[12]. H. W. Wang et al., "Effect of photosensitizer dose on fluence rate responses to photodynamic therapy," Photochem. Photobiol. 83(5), 1040-1048 (2007).

[13]. R. C. Mesquita et al., "Tumor blood flow differs between mouse strains: consequences for vasoresponse to photodynamic therapy," PLOS One 7(5), e37322 (2012).

[14]. R. Penjweini, M. M. Kim, B. Liu, and T. C. Zhu, "Evaluation of the 2-(1-Hexyloxyethyl)-2-devinylpyropheophorbide (HPPH) mediated photodynamic therapy by macroscopic singlet oxygen modeling," *J. Biophotonics* 9(11-12): 1344-1354 (2016).

[15]. H. Qiu, M. M. Kim, R. Penjweini, and T. C. Zhu, "Macroscopic singlet oxygen modeling for dosimetry of Photofrin-mediated photodynamic therapy: an in vivo study," *J. Biomed. Opt.* 21(8): 088002 (2016).

[16]. M. M. Kim, R. Penjweini, and T. C. Zhu, "Evaluation of singlet oxygen explicit dosimetry (SOED) for predicting treatment outcomes of benzoporphyrin derivative monoacid ring A (BPD-MA)-mediated photodynamic therapy," *J. Biomed. Opt.* 22(2): 028002 (2017).

[17]. T. M. Busch et al., "Fluence rate-dependent intratumor heterogeneity in physiologic and cytotoxic responses to photofrin photodynamic therapy," Photochem. Photobiol. Sci. 8(12), 1683-1693 (2009).

[18]. Wang K. K., Finlay J. C., Busch T. M., Hahn S. M., Zhu T. C., "Explicit dosimetry for photodynamic therapy: macroscopic singlet oxygen modeling," *J Biophotonics* 3(5-6), 304-18 (2010).

[19]. Hu X. H., Feng Y., Lu J. Q., et al., "Modeling of a type II photofrin-mediated photodynamic therapy process in a heterogeneous tissue phantom," *Photochemistry and photobiology* 81(6), 1460-8 (2005).

[20]. Patterson, M. S., B. C. Wilson and R. Graff (1990) In vivo tests of the concept of photodynamic threshold dose in normal rat liver photosensitized by aluminum chlorosulphonated phthalocyanine. *Photochem. Photobiol.* 51, 343-349.

[21]. Kadish, K. M., K. M. Smith and R. Guilard (2003) The Porphyrin Handbook: Applications of Phthalocyanines, Vol 19, pp. 16-18. Academic Press, An Imprint of Elsevier, San Diego

[22]. H Qiu, M M Kim, R Penjweini, J C Finlay, T M Busch, T Wang, W Guo, K A. Cengel, C B. Simone I I, E Glatstein and T C. Zhu. "A Comparison of Dose Metrics to Predict Local Tumor Control for Photofrin-mediated Photodynamic Therapy". Photochemistry and Photobiology, 2017, 93:1115-1122

The disclosure herein may comprise one or more of the following aspects:

Aspect 1. A system, comprising: a plurality of optical probes configured to be disposed at one or more locations of a patient, the plurality of optical probes each comprising a first optical fiber that is bifurcated into a second optical fiber and a third optical fiber; one or more spectrometers optically coupled to the plurality of optical probes via corresponding second optical fibers, wherein each of the plurality of optical probes is coupled to a different channel of the one or more spectrometers, wherein the one or more spectrometers are configured to generate spectral data based on optical signals from the plurality of optical probes; and at least one processor configured to at least one of: determine, based on the spectral data, data indicative of a photodynamic therapy dosage associated with a corresponding location; determine, based on optical signals from one or more of the second optical fibers, data indicative of a fluence rate of a photodynamic therapy treatment light associated with a corresponding location; and output, during a photodynamic therapy treatment, one or more of the data indicative of the photodynamic therapy dosage or the data indicative of the fluence rate for a corresponding location.

Aspect 2. The system of Aspect 1, further comprising a plurality of long pass filters configured to filter signals below a threshold, wherein each long pass filter is coupled between a corresponding optical probe and a corresponding channel of the one or more spectrometers.

Aspect 3. The system of any one of Aspects 1-2, wherein one or more of the first optical fibers comprise an isotropic light sensor at an end of the first optical fiber.

Aspect 4. The system of any one of Aspects 1-3, wherein the data indicative of the photodynamic therapy dosage comprises one or more of a fluorescence associated with a photosensitizer at one or more corresponding location, a cumulative fluorescence associated with the photosensitizer at one or more corresponding location, or a product of a concentration of the photosensitizer and a light fluence at one or more corresponding location.

Aspect 5. The system of any one of Aspects 1-4, wherein the plurality of optical probes comprises at least 4 optical probes optically coupled to at least 4 corresponding channels of the one or more spectrometers.

Aspect 6. The system of any one of Aspects 1-5, wherein the plurality of optical probes comprises at least 8 optical probes optically coupled to at least 8 corresponding channels of the one or more spectrometers.

Aspect 7. The system of any one of Aspects 1-6, further comprising a dosimetry element comprising one or more channels optically coupled to the corresponding second optical fibers, wherein the dosimetry element is configured to receive the optical signals from one or more of the second optical fibers from corresponding optical probes of the plurality of optical probes.

Aspect 8. The system of any one of Aspects 1-7, further comprising an isotropic light emitter configured to be moved to supply a treatment at the one or more of the locations of the plurality of optical probes, wherein the at least one processor being configured to output, during the photodynamic therapy treatment, the one or more of the data indicative of the photodynamic therapy dosage or the data indicative of the photodynamic therapy dosage comprises the at least one processor being configured to update, during the photodynamic therapy treatment and based on changes in a location of the isotropic light emitter, the one or more of the data indicative of the photodynamic therapy dosage or the data indicative of the photodynamic therapy dosage.

Aspect 9. The system of any one of Aspects 1-8, wherein the corresponding locations of the plurality of optical probes are spatially distributed within the patient at a treatment site for comprehensive measurement of the photodynamic therapy treatment.

Aspect 10. The system of any one of Aspects 1-9, wherein the first optical fiber being bifurcated into the second optical fiber and the third optical fiber comprises an optical splitter bifurcating the first optical fiber into the second optical fiber and the third optical fiber.

Aspect 11. The system of any one of Aspects 1-10, wherein the at least one processor is configured to determine, in parallel, the data indicative of the photodynamic therapy dosage and the data indicative of the fluence rate.

Aspect 12. The system of any one of Aspects 1-11, wherein one or more of the plurality of optical probes comprise a blood flow sensor comprising: a fourth optical fiber configured to emit light at the corresponding location; one or more fifth optical fibers configured to receive a reflection of the emitted light, wherein the at least one processor is further configured to at least one of: determine, based on optical signals received via the one or more fifth optical fibers and for one or more corresponding locations, data indicative of one or more of an oxygen level or a blood flow rate associated with the corresponding location; determine, based on the data indicative of one or more of the oxygen level or the blood flow rate, a reactive oxygen species concentration associated with the corresponding location; and output the reactive oxygen species concentration associated with the corresponding location.

Aspect 13. The system of Aspect 12, wherein the fourth optical fiber, the one or more fifth optical fibers, and the first optical fiber are integrated as a single probe.

Aspect 14. The system of any one of Aspects 12-13, wherein the data indicative of a blood flow rate comprises a blood flow index.

Aspect 15. The system of any one of Aspects 1-14, wherein the first optical fiber, the second optical fiber, and the third optical fiber are integrated as a single probe.

Aspect 16. A method comprising: determining, during photodynamic therapy and using a plurality of optical probes spatially distributed within a patient, data indicative of one or more of a photodynamic therapy dosage, a fluence rate of a photodynamic therapy treatment light, or a reactive oxygen species concentration associated with corresponding locations of the plurality of optical probes; and changing, based on the data, one or more treatment parameters associated with providing a photodynamic therapy.

Aspect 17. The method of Aspect 16, wherein the one or more treatment parameters comprise one or more of an intensity of the photodynamic therapy treatment light, a location of the photodynamic therapy treatment light, or a duration of photodynamic therapy treatment light.

Aspect 18. The method of any one of Aspects 16-17, wherein one or more of data indicative of the photodynamic therapy dosage, data indicative of the fluence rate of the photodynamic therapy treatment light, or data indicative of a reactive oxygen species concentration are determined in parallel.

Aspect 19. An integrated probe comprising: a photodynamic therapy dosage sensor comprising a first optical fiber that is bifurcated into a second optical fiber and a third optical fiber; and a blood flow sensor comprising a fourth optical fiber configured to emit a light and one or more fifth optical fibers configured to receive a reflection of the emitted light.

Aspect 20. The integrated probe of Aspect 19, wherein the integrated probe is configured to be coupled to a device configured to one or more of: determine, based on optical signals from the second optical fiber, data indicative of photodynamic therapy dosage associated with a location of the integrated probe, determine, based on optical signals from the third optical fiber, data indicative of a fluence rate of a photodynamic therapy treatment light associated with location, or determine, based on optical signals from one or more fifth optical fibers, a reactive oxygen species concentration associated with the location.

Aspect 21. A method, comprising, consisting of, or consisting essentially of: determining, during photodynamic therapy and using a plurality of optical probes spatially distributed within a patient, data indicative of a reactive oxygen species concentration associated with corresponding locations of the plurality of optical probes; and changing, based on the data, one or more treatment parameters associated with providing a photodynamic therapy.

Aspect 22. The method of Aspect 21, further comprises determining, during the photodynamic therapy and using the plurality of optical probes spatially distributed within the patient, one or more of data indicative of a photodynamic therapy dosage or data indicative of a fluence rate of a photodynamic therapy treatment light.

Aspect 23. The method of Aspect 22, wherein one or more of the data indicative of the photodynamic therapy dosage, the data indicative of the fluence rate of the photodynamic therapy treatment light, or the data indicative of a reactive oxygen species concentration are determined in parallel.

Aspect 24. The method of any one of Aspects 21-23, wherein the one or more treatment parameters comprise one or more of an intensity of the photodynamic therapy treatment light, a location of the photodynamic therapy treatment light, or a duration of photodynamic therapy treatment light.

Aspect 25. The method of any one of Aspects 21-24, further comprising: causing, during the photodynamic therapy and using the plurality of optical probes spatially distributed within a patient, emission of light; and determining, based on optical signals received via the plurality of optical probes and for one or more corresponding locations, data indicative of one or more of an oxygen level or a blood flow rate associated with the corresponding location, wherein the reactive oxygen species concentration is determined based on the data indicative of one or more of an oxygen level or a blood flow rate associated with the corresponding location.

Aspect 26. The method of any one of Aspects 21-25, wherein one of more of the plurality of optical probes comprises a blood flow sensor comprising a first optical fiber configured to emit a light and one or more second optical fibers configured to receive a reflection of the emitted light.

Aspect 27. The method of Aspect 26, wherein the one or more second optical fibers comprise a third optical fiber for receiving the reflection and a fourth optical fiber for receiving the reflection, wherein the third optical fiber has a different length than the fourth optical fiber.

Aspect 28. The method of Aspect 26, wherein the plurality of optical probes comprise a photodynamic therapy dosage sensor comprising a fifth optical fiber.

Aspect 29. A system, comprising, consisting of, or consisting essentially of: a plurality of optical probes configured to be disposed at one or more locations of a patient, the plurality of optical probes each comprising: a first optical fiber configured to emit light at a corresponding location of the one or more locations; one or more second optical fibers configured to receive a reflection of the emitted light; at least one processor configured to: determine, based on optical signals received via the one or more second optical fibers and for one or more corresponding locations, data indicative of one or more of an oxygen level or a blood flow rate associated with the corresponding location; determine, based on the data indicative of one or more of the oxygen level or the blood flow rate, a reactive oxygen species concentration associated with the corresponding location; and output the reactive oxygen species concentration associated with the corresponding location.

Aspect 30. The system of Aspect 29, wherein the plurality of optical probes comprise a third optical fiber that is bifurcated into a fourth optical fiber and a fifth optical fiber.

Aspect 31. The system of Aspect 30, further comprising: one or more spectrometers optically coupled to the plurality of optical probes via corresponding fourth optical fibers, wherein each of the plurality of optical probes is coupled to a different channel of the one or more spectrometers, wherein the one or more spectrometers are configured to generate spectral data based on optical signals from the plurality of optical probes.

Aspect 32. The system of Aspect 31, wherein the at least one processor is further configured to: determine, based on the spectral data, data indicative of a photodynamic therapy dosage associated with a corresponding location; determine, based on optical signals from one or more of the second optical fibers, data indicative of a fluence rate of a photodynamic therapy treatment light associated with a corresponding location; and output, during a photodynamic therapy treatment, one or more of the data indicative of the photodynamic therapy dosage or the data indicative of the fluence rate for a corresponding location.

Aspect 33. The system of any one of Aspects 30-32, wherein the first optical fiber, the one or more second optical fibers, and the third optical fiber are integrated as a single probe.

Aspect 34. The system of any one of Aspects 29-33, wherein the data indicative of the blood flow rate comprises a blood flow index.

Aspect 35. A method, comprising, consisting of, or consisting essentially of: causing, during photodynamic therapy and using a plurality of optical probes spatially distributed within a patient, emission of light; determining, based on optical signals received via the plurality of optical probes and for one or more corresponding locations, data indicative of one or more of an oxygen level or a blood flow rate associated with the corresponding location; determining, based on the data indicative of one or more of the oxygen level or the blood flow rate, a reactive oxygen species concentration associated with the corresponding location; and outputting the reactive oxygen species concentration associated with the corresponding location.

Aspect 36. The method of claim 35, further comprising determining, during the photodynamic therapy and using the plurality of optical probes spatially distributed within a patient, data indicative of one or more of a photodynamic therapy dosage or a fluence rate of a photodynamic therapy treatment light associated with corresponding locations of the plurality of optical probes.

Aspect 37. The method of claim 36, further comprising outputting, during the photodynamic therapy, the data indicative of one or more of the photodynamic therapy dosage or the fluence rate of the photodynamic therapy treatment light.

Aspect 38. The method of any one of claims 35-37, further comprising changing, based on the data, one or more treatment parameters associated with providing a photodynamic therapy.

Aspect 39. The method of any one of claims 35-38, further comprising determining the data indicative of one or more of an oxygen level or a blood flow rate associated with the corresponding location comprise determining data indicative of a blood flow index.

Aspect 40. The method of any one of claims 35-39, wherein determining the data indicative of one or more of an oxygen level or a blood flow rate associated with the corresponding location comprises determining data indicative of the blood flow using a one or more of a diffuse correlation spectroscopy system or a diffuse optical spectroscopy system.

Aspect 41. A non-transitory computer-readable medium storing instructions that, when executed by one or more processors, cause a one or more devices to perform the methods of any one of Aspects 16-18, 21-28, or 35-40.

Aspect 42. A device comprising: one or more processors; and a memory storing instructions that, when executed by the one or more processors, cause the device to perform the methods of any one of Aspects 16-18, 21-28, or 35-40.

It is to be understood that the methods and systems are not limited to specific methods, specific components, or to particular implementations. It is also to be understood that the terminology used herein is for the purpose of describing particular embodiments only and is not intended to be limiting.

As used in the specification and the appended claims, the singular forms "a," "an," and "the" include plural referents unless the context clearly dictates otherwise. Ranges may be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint.

"Optional" or "optionally" means that the subsequently described event or circumstance may or may not occur, and that the description includes instances where said event or circumstance occurs and instances where it does not.

Throughout the description and claims of this specification, the word "comprise" and variations of the word, such as "comprising" and "comprises," means "including but not limited to," and is not intended to exclude, for example, other components, integers or steps. "Exemplary" means "an example of" and is not intended to convey an indication of a preferred or ideal embodiment. "Such as" is not used in a restrictive sense, but for explanatory purposes.

Components are described that may be used to perform the described methods and systems. When combinations, subsets, interactions, groups, etc., of these components are described, it is understood that while specific references to each of the various individual and collective combinations and permutations of these may not be explicitly described, each is specifically contemplated and described herein, for all methods and systems. This applies to all aspects of this application including, but not limited to, operations in described methods. Thus, if there are a variety of additional operations that may be performed it is understood that each of these additional operations may be performed with any specific embodiment or combination of embodiments of the described methods.

As will be appreciated by one skilled in the art, the methods and systems may take the form of an entirely hardware embodiment, an entirely software embodiment, or an embodiment combining software and hardware aspects. Furthermore, the methods and systems may take the form of a computer program product on a computer-readable storage medium having computer-readable program instructions (e.g., computer software) embodied in the storage medium. More particularly, the present methods and systems may take the form of web-implemented computer software. Any suitable computer-readable storage medium may be utilized including hard disks, CD-ROMs, optical storage devices, or magnetic storage devices.

Embodiments of the methods and systems are described below with reference to block diagrams and flowchart illustrations of methods, systems, apparatuses and computer program products. It will be understood that each block of the block diagrams and flowchart illustrations, and combinations of blocks in the block diagrams and flowchart illustrations, respectively, may be implemented by computer program instructions. These computer program instructions may be loaded on a general-purpose computer, special-purpose computer, or other programmable data processing apparatus to produce a machine, such that the instructions which execute on the computer or other programmable data processing apparatus create a means for implementing the functions specified in the flowchart block or blocks.

These computer program instructions may also be stored in a computer-readable memory that may direct a computer or other programmable data processing apparatus to function in a particular manner, such that the instructions stored in the computer-readable memory produce an article of manufacture including computer-readable instructions for implementing the function specified in the flowchart block or blocks. The computer program instructions may also be loaded onto a computer or other programmable data processing apparatus to cause a series of operational steps to be performed on the computer or other programmable apparatus to produce a computer-implemented process such that the instructions that execute on the computer or other programmable apparatus provide steps for implementing the functions specified in the flowchart block or blocks.

The various features and processes described above may be used independently of one another, or may be combined in various ways. All possible combinations and sub-combinations are intended to fall within the scope of this disclosure. In addition, certain methods or process blocks may be omitted in some implementations. The methods and processes described herein are also not limited to any particular sequence, and the blocks or states relating thereto may be performed in other sequences that are appropriate. For example, described blocks or states may be performed in an order other than that specifically described, or multiple blocks or states may be combined in a single block or state. The example blocks or states may be performed in serial, in parallel, or in some other manner. Blocks or states may be added to or removed from the described example embodiments. The example systems and components described herein may be configured differently than described. For example, elements may be added to, removed from, or rearranged compared to the described example embodiments.

It will also be appreciated that various items are illustrated as being stored in memory or on storage while being used, and that these items or portions thereof may be transferred between memory and other storage devices for purposes of memory management and data integrity. Alternatively, in other embodiments, some or all of the software modules and/or systems may execute in memory on another device and communicate with the illustrated computing systems via inter-computer communication. Furthermore, in some embodiments, some or all of the systems and/or modules may be implemented or provided in other ways, such as at least partially in firmware and/or hardware, including, but not limited to, one or more application-specific integrated circuits ("ASICs"), standard integrated circuits, controllers (e.g., by executing appropriate instructions, and including microcontrollers and/or embedded controllers), field-programmable gate arrays ("FPGAs"), complex programmable logic devices ("CPLDs"), etc. Some or all of the modules, systems, and data structures may also be stored (e.g., as software instructions or structured data) on a computer-readable medium, such as a hard disk, a memory, a network, or a portable media article to be read by an appropriate device or via an appropriate connection. The systems, modules, and data structures may also be transmitted as generated data signals (e.g., as part of a carrier wave or other analog or digital propagated signal) on a variety of computer-readable transmission media, including wireless-based and wired/cable-based media, and may take a variety of forms (e.g., as part of a single or multiplexed analog signal, or as multiple discrete digital packets or frames). Such computer program products may also take other forms in other embodiments. Accordingly, the present invention may be practiced with other computer system configurations.

While the methods and systems have been described in connection with preferred embodiments and specific examples, it is not intended that the scope be limited to the particular embodiments set forth, as the embodiments herein are intended in all respects to be illustrative rather than restrictive.

Unless otherwise expressly stated, it is in no way intended that any method set forth herein be construed as requiring that its operations be performed in a specific order. Accordingly, where a method claim does not actually recite an order to be followed by its operations or it is not otherwise specifically stated in the claims or descriptions that the operations are to be limited to a specific order, it is no way intended that an order be inferred, in any respect. This holds for any possible non-express basis for interpretation, including: matters of logic with respect to arrangement of steps or operational flow; plain meaning derived from grammatical organization or punctuation; and the number or type of embodiments described in the specification.

It will be apparent to those skilled in the art that various modifications and variations may be made without departing from the scope or spirit of the present disclosure. Other embodiments will be apparent to those skilled in the art from consideration of the specification and practices described herein. It is intended that the specification and example figures be considered as exemplary only, with a true scope and spirit being indicated by the following claims.

What is claimed:
1. A method, comprising:
determining, during photodynamic therapy and using a plurality of optical probes spatially distributed within a patient, data indicative of a reactive oxygen species concentration associated with corresponding locations of the plurality of optical probes; and changing, based on the data, one or more treatment parameters associated with providing a photodynamic therapy.

2. The method of claim 1, further comprises determining, during the photodynamic therapy and using the plurality of optical probes spatially distributed within the patient, one or more of data indicative of a photodynamic therapy dosage or data indicative of a fluence rate of a photodynamic therapy treatment light.

3. The method of claim 2, wherein one or more of the data indicative of the photodynamic therapy dosage, the data indicative of the fluence rate of the photodynamic therapy treatment light, or the data indicative of the reactive oxygen species concentration are determined in parallel.

4. The method of claim 1, wherein the one or more treatment parameters comprise one or more of an intensity of the photodynamic therapy treatment light, a location of the photodynamic therapy treatment light, or a duration of photodynamic therapy treatment light.

5. The method of claim 1, further comprising:
causing, during the photodynamic therapy and using the plurality of optical probes spatially distributed within the patient, emission of light; and
determining, based on optical signals received via the plurality of optical probes and for one or more corresponding locations, data indicative of one or more of an oxygen level or a blood flow rate associated with the corresponding location,
wherein the reactive oxygen species concentration is determined based on the data indicative of one or more of the oxygen level or the blood flow rate associated with the corresponding location.

6. The method of claim 1, wherein one of more of the plurality of optical probes comprises a blood flow sensor comprising a first optical fiber configured to emit a light and one or more second optical fibers configured to receive a reflection of the emitted light.

7. The method of claim 6, wherein the one or more second optical fibers comprise a third optical fiber for receiving the reflection and a fourth optical fiber for receiving the reflection, wherein the third optical fiber has a different length than the fourth optical fiber.

8. The method of claim 1, wherein the plurality of optical probes comprise a photodynamic therapy dosage sensor comprising a fifth optical fiber.

9. A system, comprising:
a plurality of optical probes configured to be disposed at one or more locations of a patient, the plurality of optical probes each comprising:
a first optical fiber configured to emit light at a corresponding location of the one or more locations;
one or more second optical fibers configured to receive a reflection of the emitted light; and
at least one processor configured to:
determine, based on optical signals received via the one or more second optical fibers and for one or more corresponding locations, data indicative of one or more of an oxygen level or a blood flow rate associated with the corresponding location;
determine, based on the data indicative of one or more of the oxygen level or the blood flow rate, a reactive oxygen species concentration associated with the corresponding location; and
output the reactive oxygen species concentration associated with the corresponding location.

10. The system of claim 9, wherein the plurality of optical probes comprise a third optical fiber that is bifurcated into a fourth optical fiber and a fifth optical fiber.

11. The system of claim 10, further comprising:
one or more spectrometers optically coupled to the plurality of optical probes via corresponding fourth optical fibers, wherein each of the plurality of optical probes is coupled to a different channel of the one or more spectrometers, wherein the one or more spectrometers are configured to generate spectral data based on optical signals from the plurality of optical probes.

12. The system of claim 11, wherein the at least one processor is further configured to:
determine, based on the spectral data, data indicative of a photodynamic therapy dosage associated with a corresponding location;
determine, based on optical signals from one or more of the second optical fibers, data indicative of a fluence rate of a photodynamic therapy treatment light associated with a corresponding location; and
output, during a photodynamic therapy treatment, one or more of the data indicative of the photodynamic therapy dosage or the data indicative of the fluence rate for a corresponding location.

13. The system of claim 10, wherein the first optical fiber, the one or more second optical fibers, and the third optical fiber are integrated as a single probe.

14. The system of claim 9, wherein the data indicative of the blood flow rate comprises a blood flow index.

15. A method, comprising:
causing, during photodynamic therapy and using a plurality of optical probes spatially distributed within a patient, emission of light;
determining, based on optical signals received via the plurality of optical probes and for one or more corresponding locations, data indicative of one or more of an oxygen level or a blood flow rate associated with the corresponding location;
determining, based on the data indicative of one or more of the oxygen level or the blood flow rate, a reactive oxygen species concentration associated with the corresponding location; and
outputting the reactive oxygen species concentration associated with the corresponding location.

16. The method of claim 15, further comprising determining, during the photodynamic therapy and using the plurality of optical probes spatially distributed within the patient, data indicative of one or more of a photodynamic therapy dosage or a fluence rate of a photodynamic therapy treatment light associated with corresponding locations of the plurality of optical probes.

17. The method of claim 16, further comprising outputting, during the photodynamic therapy, the data indicative of one or more of the photodynamic therapy dosage or the fluence rate of the photodynamic therapy treatment light.

18. The method of claim 15, further comprising changing, based on the data, one or more treatment parameters associated with providing the photodynamic therapy.

19. The method of claim 15, further comprising determining the data indicative of one or more of the oxygen level or the blood flow rate associated with the corresponding location comprise determining data indicative of a blood flow index.

20. The method of claim 15, wherein determining the data indicative of one or more of the oxygen level or the blood flow rate associated with the corresponding location comprises determining data indicative of the blood flow using a one or more of a diffuse correlation spectroscopy system or a diffuse optical spectroscopy system.

21. A method comprising:
   determining, during photodynamic therapy and using a plurality of optical probes spatially distributed within a patient, data indicative of one or more of a photodynamic therapy dosage, a fluence rate of a photodynamic therapy treatment light, or a reactive oxygen species concentration associated with corresponding locations of the plurality of optical probes; and
   changing, based on the data, one or more treatment parameters associated with providing a photodynamic therapy.

22. The method of claim 21, wherein the one or more treatment parameters comprise one or more of an intensity of the photodynamic therapy treatment light, a location of the photodynamic therapy treatment light, or a duration of photodynamic therapy treatment light.

23. The method of claim 21, wherein one or more of the data indicative of the photodynamic therapy dosage, the data indicative of the fluence rate of the photodynamic therapy treatment light, or the data indicative of the reactive oxygen species concentration are determined in parallel.

24. An integrated probe comprising:
   a photodynamic therapy dosage sensor comprising a first optical fiber that is bifurcated into a second optical fiber and a third optical fiber; and
   a blood flow sensor comprising a fourth optical fiber configured to emit a light and one or more fifth optical fibers configured to receive a reflection of the emitted light.

25. The integrated probe of claim 24, wherein the integrated probe is configured to be coupled to a device configured to one or more of:
   determine, based on optical signals from the second optical fiber, data indicative of photodynamic therapy dosage associated with a location of the integrated probe,
   determine, based on optical signals from the third optical fiber, data indicative of a fluence rate of a photodynamic therapy treatment light associated with location, or
   determine, based on optical signals from one or more fifth optical fibers, a reactive oxygen species concentration associated with the location.

* * * * *